US011300572B2

(12) United States Patent
Coleman et al.

(10) Patent No.: US 11,300,572 B2
(45) Date of Patent: Apr. 12, 2022

(54) METHODS AND SYSTEMS FOR PRODUCING NANOLIPOPROTEIN PARTICLES

(71) Applicant: LAWRENCE LIVERMORE NATIONAL SECURITY, LLC, Livermore, CA (US)

(72) Inventors: Matthew A. Coleman, Oakland, CA (US); Paul D. Hoeprich, Pleasanton, CA (US); Brent W. Segelke, San Ramon, CA (US)

(73) Assignee: LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 596 days.

(21) Appl. No.: 16/159,189

(22) Filed: Oct. 12, 2018

(65) Prior Publication Data
US 2019/0094230 A1 Mar. 28, 2019

Related U.S. Application Data

(62) Division of application No. 12/118,396, filed on May 9, 2008, now abandoned.

(60) Provisional application No. 60/928,579, filed on May 9, 2007, provisional application No. 60/928,573, filed on May 9, 2007.

(51) Int. Cl.
*G01N 33/58* (2006.01)
*C07K 14/705* (2006.01)
*C12P 21/02* (2006.01)
*G01N 33/543* (2006.01)
*C07K 17/02* (2006.01)
*C07K 14/775* (2006.01)

(52) U.S. Cl.
CPC ......... *G01N 33/587* (2013.01); *C07K 14/705* (2013.01); *C12P 21/02* (2013.01); *G01N 33/54346* (2013.01); *G01N 33/582* (2013.01); *C07K 14/775* (2013.01); *C07K 17/02* (2013.01)

(58) Field of Classification Search
None
See application file for complete search history.

(56) References Cited

U.S. PATENT DOCUMENTS

| 5,374,715 | A | 12/1994 | Kanno et al. |
|---|---|---|---|
| 6,365,191 | B1 | 4/2002 | Burman et al. |
| 6,599,527 | B1 | 7/2003 | Leigh et al. |
| 7,575,763 | B2 | 8/2009 | Sligar et al. |
| 7,592,008 | B2 | 9/2009 | Sligar et al. |
| 7,622,437 | B2 | 11/2009 | Morrissey et al. |
| 7,662,410 | B2 | 2/2010 | Sligar et al. |
| 7,691,414 | B2 | 4/2010 | Sligar et al. |
| 7,824,709 | B2 | 11/2010 | Ryan et al. |
| 8,268,796 | B2 | 9/2012 | Ryan |
| 8,895,055 | B2 | 11/2014 | Lam et al. |
| 9,644,038 | B2 | 5/2017 | Luo et al. |
| 10,151,037 | B2 | 12/2018 | Hoeprich et al. |
| 11,053,322 | B2 | 7/2021 | Luo et al. |
| 2001/0051131 | A1 | 12/2001 | Unger |
| 2002/0041898 | A1 | 4/2002 | Unger et al. |
| 2003/0008014 | A1 | 1/2003 | Shelness |
| 2006/0013885 | A1 | 1/2006 | Nah et al. |
| 2006/0088524 | A1 | 4/2006 | Morrissey et al. |
| 2006/0127310 | A1 | 6/2006 | Russell-Jones et al. |
| 2006/0127467 | A1 | 6/2006 | Watkin |
| 2008/0188399 | A1 | 8/2008 | Sinko et al. |
| 2008/0248565 | A1 | 10/2008 | Katzen et al. |
| 2009/0203706 | A1 | 8/2009 | Zhao et al. |
| 2009/0324706 | A1 | 12/2009 | Mirkin et al. |
| 2010/0092567 | A1 | 4/2010 | Hoeprich et al. |
| 2010/0158994 | A1 | 6/2010 | Watkin |
| 2011/0178164 | A1 | 7/2011 | Cunha et al. |
| 2011/0286915 | A1 | 11/2011 | Lam et al. |
| 2012/0148642 | A1 | 6/2012 | Remaley et al. |
| 2012/0178029 | A1 | 7/2012 | Huang et al. |
| 2013/0164369 | A1 | 6/2013 | Lam et al. |
| 2013/0165636 | A1 | 6/2013 | Luo et al. |
| 2014/0273142 | A1 | 9/2014 | Hoeprich |
| 2014/0308341 | A1 | 10/2014 | Fujii et al. |
| 2015/0140108 | A1 | 5/2015 | Peer et al. |

(Continued)

FOREIGN PATENT DOCUMENTS

| EP | 3426304 A1 | 1/2019 |
|---|---|---|
| WO | 99/59550 A1 | 11/1999 |

(Continued)

OTHER PUBLICATIONS

Cappuccio, J.A. et al., "Cell-free Co-expression of Functional Membrane Proteins and Apolipoprotein, Forming Soluble Nanolipoprotein Particles", Molcular & Cellular Proteomics 7.11, pp. 2246-2253. Published, MCP Papers in Press, Jul. 4, 2008, DOI: 10.1074/mcp.M800191-MCP200. http://www.mcponline.org.

(Continued)

*Primary Examiner* — Kagnew H Gebreyesus

(74) *Attorney, Agent, or Firm* — Steinfl + Bruno LLP

(57) ABSTRACT

Provided herein are methods and systems for the production of a nanolipoprotein particle (NLP) that includes a scaffold protein a membrane forming lipid and optionally a target protein. At least one of the scaffold protein and target protein can be provided through an IVT system. The membrane forming lipid, scaffold protein and optionally the target protein can be assembled for a time and under conditions that allow obtaining high yield NLPs, NPLs with an increased solubility, an NLP of a controlled size, and/or an NLP having a size predetermined to include a pre-selected target protein.

23 Claims, 30 Drawing Sheets

Specification includes a Sequence Listing.

(56) References Cited

U.S. PATENT DOCUMENTS

| | | | |
|---|---|---|---|
| 2016/0083858 | A1 | 3/2016 | Hoeprich et al. |
| 2016/0235671 | A1 | 8/2016 | Li et al. |
| 2016/0324923 | A1 | 11/2016 | Dasseux et al. |
| 2018/0079829 | A1 | 3/2018 | Luo et al. |
| 2018/0186860 | A1 | 7/2018 | Hoeprich, Jr. et al. |
| 2018/0318218 | A1 | 11/2018 | Kamrud et al. |
| 2019/0055658 | A1 | 2/2019 | Hoeprich et al. |
| 2019/0094230 | A1 | 3/2019 | Coleman et al. |
| 2019/0142752 | A1 | 5/2019 | Blanchette et al. |
| 2019/0307692 | A1 | 10/2019 | Blanchette et al. |
| 2020/0046848 | A1 | 2/2020 | Coleman et al. |

FOREIGN PATENT DOCUMENTS

| | | | |
|---|---|---|---|
| WO | 02/40501 | A2 | 5/2002 |
| WO | 2007/050501 | A2 | 5/2007 |
| WO | 2010/039496 | A2 | 4/2010 |
| WO | 2014/063097 | A1 | 4/2014 |
| WO | 2017/035326 | A1 | 3/2017 |
| WO | 2017/044899 | A1 | 3/2017 |
| WO | 2017/155837 | A1 | 9/2017 |
| WO | 2018/204421 | A2 | 11/2018 |

OTHER PUBLICATIONS

Cleveland, T.E. IV, et al., "Small-angle X-ray and neutron scattering demonstrates that cell-free expression produces properly formed disc-shaped nanolipoprotein particles", Protein Science 2018, vol. 27, pp. 780-789.

Akkaladevi, N., et al., "Assembly of anthrax toxin pore: Lethal-factor complexes into lipid nanodiscs." Protein Science, 2013. 22(4): p. 492-501.

Allen, T.M. et al., "Drug delivery systems: entering the mainstream." Science, 2004. 303(5665): p. 1818-1822.

Baughman, R.H. "Solid-state polymerization of diacetylenes." Journal of Applied Physics 43(11), 4362-4370, (Nov. 1972). 10 pages.

Baylon, J.L., et al., "Characterizing the membrane-bound state of cytochrome P450 3A4: structure, depth of insertion, and orientation." Journal of the American Chemical Society, 2013. 135(23):p. 8542-8551.

Bhattacharya, P., et al., "Nanodisc-Incorporated Hemagglutinin Provides Protective Immunity against Influenza Virus Infection." Journal of Virology, 2010. 84(1): p. 361-371.

Bolikal, D. et al., "Degree of Polymerization of a Vesicle Membrane." Macromolecules, 1984. 17(6): p. 1287-1289.

Cappuccio, J.A., et al., "Cell-free expression for nanolipoprotein particles: building a high-throughput membrane protein solubility platform, in High throughput protein expression and purification." 2009, Springer. p. 273-295.

Cho, K., et al., "Therapeutic nanoparticles for drug delivery in cancer." Clinical cancer research, 2008. 14(5): p. 1310-1316.

Cuenca, Ag et al, "Emerging implications of nanotechnology on cancer diagnostics and therapeutics." Cancer, 2006. 107: pp. 459-466. pp. 8.

Das A. et al., "Screening of Type I and II Drug Binding to Human Cytochrome P450-3A4 in Nanodiscs by Localized Surface Plasmon Resonance Spectroscopy." Analytical Chemistry, 2009. 81(10): p. 3754-3759.

Ding, Y., et al., "A biomimetic nanovector-mediated targeted cholesterol-conjugated siRNA delivery for tumor gene therapy." Biomaterials, 2012. 33(34): p. 8893-8905.

Fischer, N.O., et al. "Colocalized Delivery of Adjuvant and Antigen Using Nanolipoprotein Particles Enhances the Immune Response to Recombinant Antigens." Journal of the American Chemical Society 135(6), 2044-2047, (Jan. 2013). 4 pages.

Fischer N.O. et al., "Isolation, characterization, and stability of discretely-sized nanolipoprotein particles assembled with Apolipophorin-III" PLoS One, 2010, vol. 5, No. 7, e11643.

Frias, J.C., et al. "Properties of a Versatile Nanoparticle Platform Contrast Agent To Image and Characterize Atherosclerotic Plaques by Magnetic Resonance Imaging." Nano Letters 6(10), 2220-2224, (Jul. 2006). 5 pages.

Georger, J.H., et al. "Helical and Tubular Microstructures Formed by Polymerizable Phosphatidylcholines." Journal of American Chemical Society 109(20), 6169-6175, (Sep. 1987). 7 pages.

Hayward, J.A., et al. "Biomembrane surfaces as models for polymer design: the potential for haemocompatibility." Biomaterials 5(3), 135-142, (May 1984). 8 pages.

International Preliminary Report on Patentability (Chapter 1) for International Application No. PCT/US2016/048632 filed on Aug. 25, 2016 on behalf of Lawrence Livermore National Laboratory dated Feb. 27, 2018 11 pages.

International Search Report for International Application No. PCT/US2016/048632 filed on Aug. 25, 2016 on behalf of Lawrence Livermore National Laboratory dated Feb. 6, 2017 5 pages.

International Search Report for International Application No. PCT/US2018/030648 filed on May 2, 2018 on behalf of Synthetic Genomics dated Aug. 30, 2018 4 pages.

Jia, J., et al. "Preparation, Characterizations, and In Vitro Metabolic Processes of Paclitaxel-Loaded Discoidal Recombinant High-Density Lipoproteins." Journal of Pharmaceutical Sciences 101(8), 2900-2908, (Aug. 2012). 9 pages.

Johnston, D.S., et al. "Phospholipid Polymers—Synthesis and Spectral Characteristics." Biochimica et Biophysica Acta 602 (1), 57-69, (Oct. 1980). 13 pages.

Jonsson, M.P., et al. "Supported Lipid Bilayer Formation and Lipid-Membrane-Mediated Biorecognition Reactions Studied with a New Nanoplasmonic Sensor Template." Nano Letters 7(11), 3462-3468, (Sep. 2007). 7 pages.

Justesen, B.H., et al., "Isolation of monodisperse nanodisc-reconstituted membrane proteins using free flow electrophoresis." Analytical chemistry, 2013. 85(7): p. 3497-3500.

Kim, J-M., et al. "Immobilized Polydiacetylene Vesicles on Solid Substrates for Use as Chemosensors." Advanced Materials 15(13), 1118-1121, (Jul. 2003). 4 pages.

Lamparski, H., et al. "Two-Dimensional Polymerization of Lipid Bilayers Degree of Polymerization of Sorbyl Lipids." Macromolecules 28(6), 1786-1794, (Mar. 1995). 9 pages.

Lei, J., et al. "Two-Dimensional Polymerization of Lipid Bilayers: Rate of Polymerization of Acryloyl and Methacryloyl Lipids." Macromolecules 27(6), 1381-1388, (Mar. 1994). 8 pages.

Lieser, G., et al. "Structure, Phase Transitions and Polymerizability of Multilayers of some Diacetylene Monocarboxylic Acids." Thin Solid Films 68(1), 77-90, (May 1980). 14 pages.

Madani Sy, et al., "A concise review of carbon nanotube's toxicology." Nano Rev., 2013. vol. 4, Issue 1.

Mao H.B. et al., "Design and characterization of immobilized enzymes in microfluidic systems." Analytical Chemistry, 2002. 74(2): p. 379-385.

Miyazaki, M., et al., "Effect of phospholipid composition on discoidal HDL formation." Biochimica et Biophysica Acta (BBA)-Biomembranes, 2013. 1828(5): p. 1340-1346.

Morigaki, K., et al. "Surface Functionalization of a Polymeric Lipid Bilayer for Coupling a Model Biological Membrane with Molecules, Cells, and Microstructures." Langmuir 29(8), 2722-2730, (Jan. 2013). 9 pages.

Ohno, H., et al. "Polymerization of Liposomes Composed of Diene-Containing Lipids by UV and Radical Initiators: Evidence for the Different Chemical Environment of Diene Groups on 1- and 2-Acyl Chains." Macromolecules 20(5), 929-933, (May 1987). 5 pages.

Okahata Y. et al., "Polymerizable lipid-corked capsule membranes. Polymerization at different positions of corking lipid bilayers on the capsule and effect of polymerization on permeation behavior." Journal of the American Chemical Society, 1988, vol. 110, No. 8, pp. 2495-2500.

Okazaki, T., et al. "Phase Separation of Lipid Microdomains Controlled by Polymerized Lipid Bilayer Matrices." Langmuir 26(6), 4126-4129, (Dec. 2009). 4 pages.

(56) References Cited

OTHER PUBLICATIONS

Okazaki T. et al., "Polymerized lipid bilayers on a solid substrate: Morphologies and obstruction of lateral diffusion." Langmuir, 2009. 25(1): p. 345-351.
Pavlidou M. et al., "Nanodiscs Allow Phage Display Selection for Ligands to Non-Linear Epitopes on Membrane Proteins." PLoS One, 2013. 8(9).
Portet T. et al., "A new method for measuring edge tensions and stability of lipid bilayers: effect of membrane composition." Biophysical Journal, 2010. 99(10): p. 3264-3273.
Rabinovich, A.L., et al. "On the conformational, physical properties and functions of polyunsaturated acyl chains." *Biochimica et Biophysica Acta* 1085(1), 53-62, (Aug. 1991). 10 pages.
Rawicz W. et al., "Effect of Chain Length and Unsaturation on Elasticity of Lipid Bilayers." Biophysical Journal. 2000, 79(1): p. 328-339.
Regen, S.L., et al. "Polymerized Phophatidyl Choline Vesicles. Stabilized and Controllable Time-Release Carriers." *Biochemical and Biophysical Research Communications* 101(1), 131-136, (Jul. 1981). 6 pages.
Restriction Requirement for U.S. Appl. No. 15/755,018, filed Feb. 23, 2018 on behalf of Lawrence Livermore National Laboratory, dated Oct. 2, 2019. 10 Pages.
Sadownik, A., et al. "Polymerized Liposomes Formed under Extremely Mild Conditions." *Journal of American Chemical Society* 108(24), 7789-7791, (Nov. 1986). 3 pages.
Sells, T.D., et al. "Two-Dimensional Polymerization of Lipid Bilayers: Degree of Polymerization of Acryloyl Lipids." *Macromolecules* 27(1), 226-233, (Jan. 1994). 8 pages.
Serrano, J., et al. "Polymerized Surfactant Vesicles. Determinations of Rates and Degrees of Polymerization in Vesicles Prepared from Styrene-Containing Surfactants." *Macromolecules* 18(10), 1999-2005, (Oct. 1985). 7 pages.
Sparks D.L. et al., "Effect of cholesterol on the charge and structure of apolipoprotein A-I in recombinant high density lipoprotein particles." Journal of Biological Chemistry, 1993. 268(31): p. 23250-23257.
Sparreboom, A., et al., "Comparative preclinical and clinical pharmacokinetics of a cremophor-free, nanoparticle albumin-bound paclitaxel (ABI-007) and paclitaxel formulated in Cremophor (Taxol)." *Clin Cancer Res*, 2005. 11(11): p. 4136-4143.
Tark S.H. et al., "Nanomechanical detection of cholera toxin using microcantilevers functionalized with ganglioside nanodiscs." Nanotechnology, 2010. 21(43).
Tieke, B. et al., "Polymerization of diacetylenes in multilayers." *Journal of Polymer Science: Polymer Chemistry Edition*, 1979. 17(6): p. 1631-1644.
Tsuchida, E., et al. "Polymerization of Unsaturated Phospholipids as Large Unilamellar Liposomes at Low Temperature." *Macromolecules* 25(1) 207-212, (Jan. 1992). 6 pages.
Tufteland, M. et al., "Nanodisks derived from amphotericin B lipid complex." *Journal of Pharmaceutical Sciences*, 2008. 97(10): p. 4425-4432.
Vickers, K.C., et al., "MicroRNAs are transported in plasma and delivered to recipient cells by high-density lipoproteins." *Nat Cell Biol*, 2011. 13(4): p. 423-433.
Wadsater, M., et al., "Monitoring shifts in the conformation equilibrium of the membrane protein cytochrome P450 reductase (FOR) in nanodiscs." *Journal of Biological Chemistry*,2012. 287(41): p. 34596-34603.
Wang, J., et al., "Tumor targeting effects of a novel modified paclitaxel-loaded discoidal mimic high-density lipoproteins." *Drug delivery*, 2013. 20(8): p. 356-363.
Wang, S. et al., "The unsolved mystery of apoA-1 recycling in adipocyte." *Lipids Health Dis*, 2016. 15: p. 35.
Weilhammer, D.R., et al., "The use of nanolipoprotein particles to enhance the immunostimulatory properties of innate immune agonists against lethal influenza challenge." *Biomaterials*, 2013. 34(38): p. 10305-10318.

Written Opinion for International Application No. PCT/US2018/030648 filed on May 2, 2018 on behalf of Synthetic Genomics dated Aug. 30, 2018 6 pages.
Written Opinion for International Application No. PCT/US2016/048632 filed on Aug. 25, 2016 on behalf of Lawrence Livermore National Laboratory dated Feb. 6, 2017 10 pages.
Yang T. et al., "Identification and cellular localization of human PFTAIRE1" Gene, 2001. 267(2): p. 165-172.
Yang T.L. et al., "Investigations of bivalent antibody binding on fluid-support phospholipid membranes: The effect of hapten density." Journal of the American Chemical Society, 2003. 125(16): p. 4779-4784.
Yavlovich, A., et al., "A novel class of photo-triggerable liposomes containing DPPC:DC8,9PC as vehicles for delivery of doxorubcin to cells." *Biochimica Et Biophysica Acta-Biomembranes*, 2011. 1808(1): p. 117-126.
Yuan, Y., et al., "Delivery of hydrophilic drug doxorubicin hydrochloride-targeted liver using apoAI as carrier." *J Drug Target*, 2013. 21(4): p. 367-374.
Zidovska A. et al., "Block Liposome and Nanotube Formation is a General Phenomenon of Two-Component Membranes Containing Multivalent Lipids", Jan. 1, 2011, Soft Matter, vol. 7, No. 18, pp. 8363-8369.
Abdulreda M.H., et al., "Atomic Force Microscope Spectroscopy Reveals a Hemifusion Intermediate during Soluble N-Ethylmaleimide-Sensitive Factor-Attachment Protein Receptors-Mediated Membrane Fusion," Biophysical Journal, Jan. 2008, vol. 94 (2), 648-655. 8 pages.
Advisory Action for U.S. Appl. No. 12/118,396, filed May 9, 2008, dated Jul. 7, 2015, 8 pages.
Bayburt T.H., et al., "Single-Molecule Height Measurements on Microsomal Cytochrome P450 in Nanometer-Scale Phospholipid Bilayer Disks," Proceedings of the National Academy of Sciences of the United States of America, May 2002, vol. 99 (10), 6725-6730. 6 pages.
Blanchette C.D., et al., "Atomic Force Microscopy Differentiates Discrete Size Distributions Between Membrane Protein Containing and Empty Nanolipoprotein Particles," Biochimica et Biophysica Acta, 2009, vol. 1788 (3), 724-731. 8 pages.
Boschker H.T.S., et al., "The Contribution of Macrophyte-derived Organic Matter to Microbial Biomass in Salt-marsh Sediments: Stable Carbon Isotope Analysis of Microbial Biomarkers," Limnology and Oceanography, 1999, vol. 44(2), 309-319. 11 pages.
Brodie et al., "Profiling Microbial Identity and Activity: Novel Applications of NanoSIMS and High Density Microarrays", Systems Biology Strategies and Technologies for Understanding Microbes and Microbial Communities: Genomic and Proteomic Strategies, 2008, 137. 1 page.
Carrell T., et al., "A Novel Procedure for the Synthesis of Libraries Containing Small Organic Molecules," Angewandte Chemie International Edition in English, Nov. 1994, vol. 33 (20), 2059-2061. 3 pages.
Das D., et al., "Role of Fe-hydrogenase in Biological Hydrogen Production," Current Science, Jun. 2006, vol. 90 (12), 1627-1637. 11 pages.
Definition of "homogeneous", Oxford Dictionaries, retrieved from htttps://en.oxforddictionaries.com/definition/homogeneous on Apr. 4, 2018. 4 pages.
Denisov I.G., et al., "Nanodiscs in Membrane Biochemistry and Biophysics", Chemical Reviews, Mar. 2017, vol. 117 (6), 4669-4713. 92 pages.
International Search Report and Written Opinion for Application No. PCT/US2015/051516 filed on Sep. 22, 2015, dated Jan. 25, 2016, 12 pages.
International Search Report for Application No. PCT/US2015/051172 filed on Sep. 21, 2015, dated Jan. 7, 2016, 6 pages.
"Ion channel", Wikipedia, accessed Dec. 22, 2014, pp. 1-8, 8 pages.
Loll, Pj, "Membrane protein structural biology: the high throughput challenge", J. of Structural Biology, 142:144-153; 2003.
Ly, S., et al., (Jan. 2014) "Quantifying interactions of a membrane protein embedded in lipid nanodisc using fluorescence correlation spectroscopy," Biophysical Journal. 106: L05-L08.

(56) References Cited

OTHER PUBLICATIONS

"Newpoint O2 Removal Services", https://www.newpointgas.com/services/oxygen-o2-removal/, 2017, 4 pages.
Plumere, et al., "Enzyme-catalyzed O2 removal system for electrochemical analysis under ambient air: application in an amperometric nitrate biosensor (Abstract only)", Anal Chem. Mar. 6, 2012;84(5):2141-2146, Epub Feb. 10, 2012. 2 pages.
Ly, S., et al., "Quantifying membrane protein interactions in solution using fluorescence correlation spectroscopy," Biophysical Journal, (Aug. 15, 2013), LLNL-JRNL-642412. Lawrence Livermore National Laboratory. 11 pages.
Restriction Requirement for U.S. Appl. No. 12/118,530, filed May 9, 2008, dated Sep. 24, 2010, 14 pages.
Sligar S., "The Self-assembly of Integral Membrane Proteins Into Nanodiscs" Sligar Lab, University of Illinois at Urbana-champaign. Printout website dated Jun. 13, 2010, http://sligarlab.life.uiuc.edu/members.html, 2 pages.
Adams, M.W.W., et al., "Hydrogenase," 1981, Biochimica et Biophysica Acta 594, 105-176.
Anantharamaiah, G.M., et al., "Studies of Synthetic Peptide Analogs of the Amphipathic Helix," 1985, The Journal of Biological Chemistry, vol. 260, No. 18, 10248-10255.
Bay et al., "Small multidrug resistance proteins: A multidrug transporter family that continues to grow," Biochimica et Biophysica Acta 1778 (2008) 1814-1838.
"Catalytic oxygen removal from coal mine methane," http://www.digitalrefining.com/article/1000623,Catalytic_oxygen_removal_from_coal_mine_methane.html#. . . , accessed Nov. 27, 2017, 4 pages.
Chung, B.H., et al., "Studies of Synthetic Peptide Analogs of the Amphipathic Helix," 1985, The Journal of Biological Chemistry, vol. 260, No. 18, 10256-10262.
Gao, T., et al., "Characterization of de novo synthesized GPCRs supported in nanolipoprotein discs," (2012) E.Pub, PloS One. 7(9):44911. 8 pages.
Gao, T., et al., (2011) "Characterizing diffusion dynamics of a membrane protein associated with nanolipoproteins using fluorescence correlation spectroscopy," Protein Science. 20:437-447.
He, W., "Controlling the Diameter, Monodispersity and Solubility of ApoA1 Nanolipoprotein Particles using Telodendrimer Chemistry," (2013) Protein Science 22, 1078-1086.
Imura, T., et al., "Minimum Amino Acid Residues of an a-Helical Peptide Leading to Lipid Nanodisc Formation," 2014, J. Oleo Sci. 63, (11) 1203-1208.
Imura, T., et al., "Surfactant-like Properties of an Amphilic a-Helical Peptide Leading to Lipid Nanodisc Formation," 2014, Langmuir, 20, 4752-4759.
"Individual" from Merriam-Webster, Jan. 13, 2015, accessed via WayBackMachine.com (2 pages).
International Preliminary Report on Patentability for Application No. PCT/US2015/051172 filed on Sep. 9, 2016 on behalf of Lawrence Livermore National Security, LLC, dated Mar. 13, 2018. 8 pages. (English Only).
International Preliminary Report on Patentability for Application No. PCT/US2015/051516 filed on Sep. 22, 2015 on behalf of Lawrence Livermore National Security, LLC, dated Mar. 28, 2017, 10 pages. (English Only).
Langworthy, T.A., "Lipids of Thermoplasma," 1982, Methods in Enzymology, vol. 88, 396-406.
Ma, K., et al., "Characterization of Hydrogenase II from the Hyperthermophilic Archaeon Pyrococcus furiosus and Assessment of Its Role in Sulfur Reduction," Apr. 2000, Journal of Bacteriology, vol. 182, No. 7, 1864-1871.
Marshall, G.R., et al., "Conformational effects of chiral a,a-dialkyl amino acids," 1988, Int. J. Peptide Protein Res., 32, 544-555.
"Microsome" from Wikipedia, Mar. 3, 2008, accessed via WayBackMachine.com (1 pg).
Midtgaard, S.R., et al., "Self-assembling peptides form nanodiscs that stabilize membrane proteins," 2014, Soft Matter, 10, 738-752.
Notice of Allowance for U.S. Appl. No. 14/861,750, filed Sep. 22, 2015 on behalf of Lawrence Livermore National Security, LLC, dated Jul. 24, 2018. 15 pages.
Sabatini, D.D., et al., "Mechanisms for the Incorporation of Proteins in Membranes and Organelles," Jan. 1, 1982, The Journal of Cell Biology, vol. 92, 1-22.
Singer, S.J., et al., "The Fluid Mosaic Model of the Structure of Cell Membranes," Feb. 1972, Science, vol. 175, 720-731.
Sligar webpage http://sligarlab.life.uiuc.edu/nanodisc.html, accessed Feb. 28, 2018. "Nanodisc Technology: Soluble Lipid Bilayer Systems for Structural and Functional Studies of Membrane Proteins" (3 pages).
Grinkova, Y.V., et al., "Engineering extended membrane scaffold proteins for self-assembly of soluble nanoscale lipid bilayers," Protein Engineering, Design and Selection, 2010, vol. 23, No. 11, pp. 843-848.
"Vesicle" from Wikipedia, Dec. 16, 2008, accessed via WayBackMachine.com (5 pages).
Wu, L., et al., "Membrane targeting and translocation of bacterial hydrogenases," 2000, Arch Microbiology, 173:319-324.
Zhou, H., et al., Noncovalent Attachment of NAD+ Cofactor onto Carbon Nanotubes for Preparation of Integrated Dehydrogenase-Based Electrochemical Biosensors,: 2010, Langmuir Article, 26(8) 6028-6032.
Stryer., "Lipid Vesicles (Liposomes) and Planar Bilayer Membranes are Valuable Model Systems," Biochemistry, 1995, 1 page.
Tercier-Waeber, et al., "Submersible Online Oxygen Removal System Coupled to an in Situ Voltammetric Probe for Trace Element Monitoring in Freshwater (Abstract only)", Environ. Sci. Technol., 2000, 34 (18), pp. 4018-4024, Publication Date (Web): Aug. 11, 2000. 4 pages.
VICI (Valco Instruments Co. Inc.) "Oxygen Removal System", https://www.vici.com/instr/deox.php, pp. 1-2, 2 pages, 2018.
White S.H., et al., "How Translocons Select Transmembrane Helices," Annual Review of Biophysics, 2008, vol. 37, 23-42. 20 pages.
Aina O.H., et al., "From combinatorial chemistry to cancer-targeting peptides" Mol Pharm, vol. 4, No. 5, pp. 631-651 (2007).
Blanchette C.D., et al., "Kinetic analysis of his-tagged protein binding to nickel-chelating nanolipoprotein particles." Bioconjug Chem, 21, pp. 1321-1330 (Jul. 2010).
Chen et al., "Fluorescence Study of Inclusion Complexes between Star-Shaped Cholic Acid Derivatives and Polycyclic Aromatic Fluorescent Probes and the Size Effects of Host and Guest Molecules" Journal of Physical Chemistry vol. 112, No. 11, p. 3402-3409 (2008).
Corrected Notice of Allowance for U.S. Appl. No. 13/719,785, filed Dec. 19, 2012 on behalf of Lawrence Livermore National Laboratory dated May 23, 2016 5 pages.
Dalkara et al., "Intracytoplasmic Delivery of Anionic Proteins" Molecular Therapy, Jun. 2004, vol. 9, No. 6, pp. 964-969.
Duncan R., "Dawning Era of Polymer Therapeutics" Nature Review Drug Discovery vol. 2, No. 5 p. 347-360 (2003).
Final Office Action for U.S. Appl. No. 15/499,855, filed Apr. 27, 2017 on behalf of Lawrence Livermore National Laboratory dated Aug. 8, 2019 11 pages.
Ghosh M, et al., "Cationic lipid Nanodisks as an siRNA delivery vehicle" Biochem Cell Biol (2014), 92(3): 200-205. 14 pages.
Gref et al., "Biodegradable Long-Circulating Polymeric Nanospheres" Science American Association for the Advancement of Science vol. 263 No. 5153, p. 1600-1603 (1994).
International Search Report and Written Opinion for PCT/US2009/057852, 19 pages, dated May 6, 2010.
International Search Report and Written Opinion for PCT/US2012/070508, 9 pages, dated Feb. 27, 2013.
Keppetipola S, et al., From gene to HSQC in under five hours: high-throughput NMR proteomics: J Am Chem Soc, 128, pp. 4508-4509 (Apr. 2006).
Kigawa T, et al., "Cell-free production and stable-isotope labeling of milligram quantities of proteins" FEBS Lett, 442, pp. 15-19 (Jan. 1999).
Klussman S, et al., "The Aptamer Handbook: Functional Oligonucleotides and Their Applications" *Wiley-VCH*(2006) 509 pages.

(56) References Cited

OTHER PUBLICATIONS

Lam K, et al., "A new type of synthetic peptide library for identifying ligand-binding activity" Nature, vol. 354, pp. 82-84 (1991).

Levy-Nissenbaum E. et al., "Nanotechnology and aptamers: applications in drug delivery" Trends in Biotechnology 26(8):442-449(2008).

Li et al., "Antimicrobial Activities of Amine-and Guanidine-Functionalized Cholic Acid Derivatives" Antimicrobial Agents and Chemotherapy vol. 43 (6) p. 1347-1349 (Jun. 1999).

Luo et al., "Asymmetric Poly(ethylene glycol) Star Polymers with a Cholic Acid Core and Their Aggregation Properties" Biomacromolecules vol. 10 No. 4 p. 900-906 (2009).

Luo J, et al., "Well-defined, size-tunable, multifunctional micelles for efficient paclitaxel delivery for cancer treatment." Bioconjug Chem, 21, pp. 1216-1224 (Jul. 2010).

Mori M, et al., "Cell-free synthesis and processing of a putative precursor for mitochondrial carbamyl phosphate synthetase I of rat liver" Proc Natl Acad Sci USA, vol. 76, No. 10, pp. 5071-5075 (Oct. 1979).

Non-Final Office Action for U.S. Appl. No. 13/719,785, filed Dec. 19, 2012 on behalf of Lawrence Livermore National Laboratory dated Jun. 4, 2015 8 pages.

Non-Final Office Action for U.S. Appl. No. 15/499,855, filed Apr. 27, 2017, on behalf of Lawrence Livermore National Security LLC, dated Jan. 11, 2019. 7 pages.

Notice of Allowance for U.S. Appl. No. 13/719,785, filed Dec. 19, 2012 on behalf of Lawrence Livermore National Laboratory dated Feb. 17, 2016 7 pages.

Rensen Pc, et al., "Human recombinant apolipoprotein E-enriched liposomes can mimic low-density lipoproteins as carriers for the site-specific delivery of antitumor agents." Mol Pharmacol, 52, pp. 445-455 (Sep. 1997).

Ryan Ro, "Nanobiotechnology applications of reconstituted high density lipoprotein" J Nanobiotechnology, 8:28 (Dec. 2010) 10 pages.

Ryan Ro, "Nanodisks: hydrophobic drug delivery vehicles" Expert Opin Drug Deliv., 5(3), pp. 343-351 (Mar. 2008).

Semple et al., "Rational design of cationic lipids for siRNA delivery" Nature Biotechnology Feb. 2010, vol. 28, No. 2, pp. 172-176 + 2 additional pages.

Sunahara H, et al., "Design and synthesis of a library of BODIPY-based environmental polarity sensors utilizing photoinduced electron-transfer-controlled fluorescence ON/OFF switching" J Am Chem Soc., 129, pp. 5597-5604 (May 2007).

Vijayalakshmi et al., "A Simple Construction of a Bile Acid Based Dendritic Light Harvesting System" Organic Letters vol. 7 No. 13 p. 2727-2730 (2005).

Xiao et al., "PEG oligocholic acid Telodendrimer micelles for the targeted delivery of doxorubicin to B cell lymphoma" Journal of Controlled Release vol. 155 p. 272-281 (2011).

Xiao K, et al., "A self-assembling nanoparticle for paclitaxel delivery in ovarian cancer." Biomaterials, 30 (30) pp. 6006-6016 (2009) 24 pages.

Yang Jp, et al., "Cell-free synthesis of a functional G protein-coupled receptor complexed with nanometer scale bilayer discs." BMC Biotechnol, 11:57, (May 2011) 8 pages.

Zuris J, et al., "Cationic lipid-mediated delivery of proteins enables efficient protein-based genome editing in vitro and in vivo" Nature Biotechnology, vol. 33, No. 1, p. 73-80 (2015) 8 pages.

Final Office Action for U.S. Appl. No. 15/744,754, filed Jan. 12, 2018, on behalf of Lawrence Livermore National Laboratory, dated Oct. 14, 2020. 21 Pages.

Gilmore S. F. et al., "Lipid composition dictates serum stability of reconstituted high-density lipoproteins: implications for in vivo applications" Royal Society of Chemistry, Nanoscale, Mar. 2018, 10, 7420-7430. 12 pages.

Gilmore S. F. et al., "Lipid cross-linking of nanolipoprotein particles substantially enhances serum stability and cellular uptake" Applied Materials and Interfaces, Jul. 2016, 8, 20549-20557. 9 pages.

Hafner, et al, "Development status and future prospects for a vaccine against Chlamydia trachomatis infection," Vaccine, 32, (2014), pp. 1563-1571. Published online: Aug. 22, 2013. 9 Pages.

Kuai R. et al., "Designer vaccine nanodiscs for personalized cancer immunotherapy" Nature Materials, Dec. 2016 10 pages. DOI:10.1038/NMAT4822.

Kuai R. et al., "Designer vaccine nanodiscs for personalized cancer immunotherapy (Supplementary Information)" Nature Materials, Dec. 2016 18 pages. DOI:10.1038/NMAT4822.

Liposome—Wikipedia, the free encyclopedia. Dated: Jul. 5, 2016, 7 pages, https://en.wikipedia.org/wiki/Liposome.

Micelle—Wikipedia, the free encyclopedia, Dated: Dec. 1, 2020, 7 pages https://en.wikipedia.org/wiki/Micelle.

Nanodisc—Wikipedia, the free encyclopedia. Dated: Jul. 5, 2016, 3 pages, https://en.wikipedia.org/wiki/Nanodisc.

Nanodisc Inc. Company Profile—ZoomInfo.com, Dated: May 25, 2015, 2 pages, https://www.zoominfo.com/c/nanodisc/65701329.

Non-Final Office Action for U.S. Appl. No. 16/609,420, filed Oct. 29, 2019 on behalf of Lawrence Livermore National Laboratory, dated Dec. 28, 2020. 53 Pages.

Notice of Allowance for U.S. Appl. No. 15/499,855, filed Apr. 27, 2017 on behalf of Lawrence Livermore National Security, LLC, dated Oct. 15, 2020. 9 pages.

Plotkin, et al., Vaccines, WB Saunders Company, p. 571. Year: 1988. 2 Pages.

Advisory Action for U.S. Appl. No. 15/744,754, filed Jan. 12, 2018 on behalf of Lawrence Livermore National Security, LLC, dated Mar. 16, 2021. 13 pages.

Bloedon L.T. et al., "Safety, pharmacokinetics, and pharmacodynamics of oral apoA-I mimetic peptide D-4F in high-risk cardiovascular patients" Journal of Lipid Research, vol. 49, Mar. 2008, pp. 1344-1352.

Borhani D. W. et al., "Crystal structure of truncated human apolipoprotein A-I suggests a lipid-bound conformation" Proc. Natl. Acad. Sci. USA, vol. 94, Nov. 1997, pp. 12291-12296.

Elson E. L. "Fluorescence Correlation Spectroscopy: Past, Present, Future" Biophysical Journal, vol. 101, Dec. 2011, pp. 2855-2870.

Extended European Search Report for EP Application No. 17763807.9 filed on Oct. 4, 2018 on behalf of Lawrence Livermore National Security LLC, dated Oct. 30, 2019. 8 pages.

Leman L.J. et al., "Molecules that Mimic Apolipoprotein A-I: Potential Agents for Treating Atherosclerosis" J Med Chem, 57(6), Mar. 2014, 2169-2196. 56 pages.

Li L. et al., "Double Belt Structure of Discoidal High Density Lipoproteins: Molecular Basis for Size Heterogeneity" J. Mol. Biol, vol. 343, 2004, pp. 1293-1311.

Mendez A.J. "Synthetic Amphipathic Helical Peptides That Mimic Apolipoprotein A-I in Clearing Cellular Cholesterol" J Clin. Invest, vol. 94, Oct. 1994, pp. 1698-1705.

Notice of Allowance for U.S. Appl. No. 15/499,855, filed Apr. 27, 2017 on behalf of Lawrence Livermore National Security LLC, dated Jan. 25, 2021. 9 pages.

Popot J.L. "Alternatives to Detergents for Handling Membrane Proteins in Aqueous Solutions" Membrane Proteins in Aqueous Solutions, Jun. 2018, pp. 97-149. 134 pages.

Popovic K. et al., "Structure of saposin A lipoprotein discs" PNAS, vol. 109, No. 8, Feb. 2012, pp. 2908-2912.

Segrest J. P. "Amphipathic Helix Motif: Classes and Properties" Proteins: Structure, Function, and Genetics, vol. 8, 1990, pp. 103-117.

Segrest J.P. et al., "Pathogenesis of atherosclerosis" Current Opinion in Cardiology, vol. 9, 1994, pp. 404-410.

Spuhler P. et al., "Binding of Apolipoprotein A-I Model Peptides to Lipid Bilayers" The Journal of Biological Chemistry, vol. 269, No. 39, Sep. 1994, pp. 23904-23910.

Swainsbury D.J.K. et al., "The effectiveness of styrene-maleic acid (SMA) copolymers for solubilisation of integral membrane proteins from SMA-accessible and SMA-resistant membranes" BBA-Biomembranes, 1859, Jul. 2017, pp. 2133-2143.

Troutt J.S. et al., "An apolipoprotein A-I mimetic dose-dependently increases the formation of preB1 HDL in human plasma" Journal of Lipid Research, vol. 49, Mar. 2008, pp. 581-587.

(56) References Cited

OTHER PUBLICATIONS

Watson C.E. et al., "Treatment of patients with cardiovascular disease with L-4F, an apo-A1 mimetic, did not improve select biomarkers of HDL function" Journal of Lipid Research, vol. 52, Feb. 2011, pp. 361-373.

Wool G.D. "Apolipoprotein A-I mimetic peptide helix number and helix linker influence potentially anti-atherogenic properties" Journal of Lipid Research, vol. 49, 2008, pp. 1268-1283.

Zhao Y. et al., "Self-Assembling Cyclic D,L-a-Peptides as Modulators of Plasma HDL Function. A Supramolecular Approach toward Antiatherosclerotic Agents" ACS Central Science, vol. 3, Jun. 2017, pp. 639-646.

Badamchi-Zadeh A, et al., "A multi-component prime-boost vaccination regimen with a consensus MOMP antigen enhances chlamydia trachomatis clearance." Frontiers In Immunology, vol. 7, Article 162, pp. 1-11 (Apr. 2016).

Baehr W, et al., "Mapping antigenic domains expressed by Chlamydia trachomatis major outer membrane protein genes." Proceeding of the National Academy of Sciences, vol. 85, pp. 4000-4004 (1988).

Carmichael J.R. et al., "Induction of protection against vaginal shedding and infertility by recombinant Chlamydia vaccine" *Vaccine*, 29,pp. 5276-5283(2011).

Claypool et al., An ethanol/ether soluble apoprotein from rat lung surfactant augments liposome uptake by isolated granular pneumocytes. J Clin Invest. Sep. 1984; 74(3): 677-84. (Year: 1984). 8 pages.

Coleman M.A, et al., "Expression and Association of the Yersinia pestis Translocon Proteins, YopB and YopD, Are Facilitated by Nanolipoprotein Particles." *PLoS One* p. e0150166 (2016). 16 pages.

Conlan J, et al., "Isolation of recombinant fragments of the major outer-membrane protein of Chlamydia trachomatis: their potential as subunit vaccines" Microbiology, 136, pp. 2013-2020 (1992).

Davidson E, et al., "A high-throughput shotgun mutagenesis approach to mapping B-cell antibody epitopes" Immunology, 143, pp. 13-20 (2014).

Farris C.M. et al., "CD4+ T cells and antibody are required for optimal major outer membrane protein vaccine-induced immunity to Chlamydia muridarum genital infection" Infection and Immunity, vol. 78, No. 10, pp. 4374-4383 (2010).

Feher V.A. et al., "A 3-dimensional trimeric B-barrel model for Chlamydia MOMP contains conserved and novel elements of Gram-negative bacterial porins." PloS one p. e68934, vol. 8, Issue 7 (2013). 11 pages.

Ferrara L.G.M. et al., "MOMP from Campylobacter jejuni Is a Trimer of 18-Stranded beta-Barrel Monomers with a Ca(2+) Ion Bound at the Constriction Zone." J Mol Biol(2016), 428(22), pp. 4528-4543. 16 pages.

Findlay H.E, et al., "Surface expression, single-channel analysis and membrane topology of recombinant Chlamydia trachomatis Major Outer Membrane Protein" *BMC Microbiol*, 5:5 (2005). 15 pages.

Friedrich T. et al., "The respiratory complex I of bacteria, archaea and eukarya and its module common with membrane-bound multisubunit hydrogenases." FEBS Lett. Aug. 2000 11;479(1-2):1-5.

Haque F, et al., "Incorporation of a viral DNA-packaging motor channel in lipid bilayers for real-time, single-molecule sensing of chemicals and double-stranded DNA." Nat Protoc, vol. 8, No. 2, pp. 373-392 (2013).

He W, et al., "Cell-free expression of functional receptor tyrosine kinases" *Sci Rep*, 5:12896(2015). 8 pages.

He W, et al., "Producing Membrane Bound Proteins as Countermeasures to infectious Diseases" Synthetic Genomics Vaccines (2016).

Howland M.C. et al., "Model Studies of Membrane Disruption by Photogenerated Oxidative Assault." The Journal of Physical Chemistry, 2010. 114(19); p. 6377-6385.

Inic-Kanada A, et al., "A Probiotic Adjuvant Lactobacillus rhamnosus Enhances Specific Immune Responses after Ocular Mucosal Immunization with Chlamydial Polymorphic Membrane Protein C." PLoS One p. e015785 (2016) 14 pages.

International Preliminary Report on Patentability (Chapter 1) for International Application No. PCT/US2017/020827 filed on Mar. 3, 2017 on behalf of Lawrence Livermore National Laboratory dated Sep. 11, 2018 9 pages.

International Preliminary Report on Patentability for International Application No. PCT/US2018/030537 filed on May 1, 2018 on behalf of Lawrence Livermore National Security, dated Nov. 14, 2019. 11 pages.

International Search Report for International Application No. PCT/US2017/020827 filed on Mar. 3, 2017 on behalf of Lawrence Livermore National Laboratory dated Jun. 20, 2017 4 pages.

International Search Report for International Application No. PCT/US2018/030537 filed on May 1, 2018 on behalf of Lawrence Livermore National Security dated Jan. 17, 2019 5 pages.

Johnson R.M. et al., "PmpG 303-311, a protective vaccine epitope that elicits persistent cellular immune responses in Chlamydia muridarum-immune mice." Infect Immun, vol. 80, No. 6, p. 2204-2211 (2012).

Karunakaran K.P. et al., "Immunoproteomic discovery of novel T cell antigens from the obligate intracellular pathogen Chlamydia" J Immunol p. 2459-2465 (2008).

Karunakaran K.P. et al., "Outer membrane proteins preferentially load MHC class II peptides: implications for a Chlamydia trachomatis T cell vaccine." Vaccine, 33, p. 2159-2166 (2015).

Koren E, et al., "Clinical validation of the "in silico" prediction of immunogenicity of a human recombinant therapeutic protein" Clinical Immunology, 124, pp. 26-32 (2007).

Kreshech G.C. "Surfactants in Water—A Comprehensive Treatise." 1975: Plenum, New York.

Manning D.S. et al., "Expression of the major outer membrane protein of Chlamydia trachomatis in *Escherichia coli*." Infection and Immunity, vol. 61, No. 10, pp. 4093-4098 (1993).

Pal S, et al., "Comparison of the nine polymorphic membrane proteins of Chlamydia trachomatis for their ability to induce protective immune responses in mice against a C. muridarum challenge." Vaccine, 35, p. 2543-2549 (2017).

Pal S, et al., "Immunization with an acellular vaccine consisting of the outer membrane complex of Chlamydia trachomatis induces protection against a genital challenge" Infection and Immunity, vol. 65, No. 8, pp. 3361-3369 (1997).

Pal S, et al., "Immunization with the Chlamydia trachomatis mouse pneumonitis major outer membrane protein can elicit a protective immune response against a genital challenge" Infection and immunity, vol. 65, No. 10, pp. 6240-6247 (2001).

Pal S, et al., "Vaccination with the Chlamydia trachomatis major outer membrane protein can elicit an immune response as protective as that resulting from inoculation with live bacteria" Infection and Immunity, vol. 73, No. 12, pp. 8153-8160 (2005).

Ralli-Jain P, et al., "Enhancement of the protective efficacy of a Chlamydia trachomatis recombinant vaccine by combining systemic and mucosal routes for immunization." Vaccine, 28, pp. 7659-7666 (2010).

Rapp V. et al., "Predicting Fuel Performance for Future HCCI Engines" Combust. Sci. Technol., 185: 735-748, Apr. 20, 2013. 15 pages.

Restriction Requirement for U.S. Appl. No. 15/744,754, filed Jan. 12, 2018 on behalf of Lawrence Livermore National Laboratory dated Aug. 7, 2019 9 pages.

Restriction Requirement for U.S. Appl. No. 16/082,924, filed Sep. 6, 2018 on behalf of Lawrence Livermore National Laboratory dated Oct. 24, 2019 9 pages.

Rodriguez-Maranon M.J. et al., "Prediction of the membrane-spanning Beta-strands of the major outer membrane protein of Chlamydia" Protein Science, 11, pp. 1854-1861 (2006).

Saito H. et al., "Contributions of domain structure and lipid interaction to the functionality of exchangeable human apolipoproteins" Elsevier, 2004. pp. 350-380.

Smith D. et al., "Solubilisation of methane monooxygenase from Methylococcus capsulatus (Bath)" Eur. J. Biochem, 182, pp. 667-671, Jan. 17, 1989, 6 pages.

(56) References Cited

OTHER PUBLICATIONS

Su H, et al., "Immunogenicity of a chimeric peptide corresponding to T helper and B cell epitopes of the Chlamydia trachomatis major outer membrane protein" Journal of Experimental Medicine, vol. 175, pp. 227-235 (1992).
Sun G, et al., "Protection against an intranasal challenge by vaccines formulated with native and recombinant preparations of the Chlamydia trachomatis major outer membrane protein" Vaccine, 27, pp. 5020-5025 (2009).
Sun G, et al., "Structural and functional analyses of the major outer membrane protein of Chlamydia trachomatis" J Bacteriol, vol. 189, No. 17, pp. 6222-6235 (2007).
Tang G, et al., "EMAN2: an extensible image processing suite for electron microscopy" J Struct Biol, 157, pp. 38-46 (2007).
Tifrea D.F. et al., "Amphipols stabilize the Chlamydia major outer membrane protein and enhance its protective ability as a vaccine" Vaccine, 29, pp. 4623-4631 (2011).
Tifrea D.F. et al., "Increased immunoaccessibility of MOMP epitopes in a vaccine formulated with amphipols may account for the very robust protection elicited against a vaginal challenge with Chlamydia muridarum" The Journal of Immunology, 192, pp. 5201-5213 (2014).
Toniolo C. et al., "Lipopeptaibols, a novel family of membrane active, antimicrobial peptides" *Cellular and Molecular Life Sciences*, vol. 58, 2001, pp. 1179-1188, 10 pages.
Tu J, et al., "A multi-epitope vaccine based on Chlamydia trachomatis major outer membrane protein induces specific immunity in mice." Acta biochimica et biophysica Sinica, vol. 46, Issue 5, pp. 401-408 (2014).
Wang Y, et al., "Identification of surface-exposed components of MOMP of Chlamydia trachomatis serovar F." Protein Science, 15, pp. 122-134 (2006).
Written Opinion for International Application No. PCT/US2017/020827 filed on Mar. 3, 2017 on behalf of Lawrence Livermore National Laboratory dated Jun. 20, 2017 8 pages.
Written Opinion for International Application No. PCT/US2018/030537 filed on May 1, 2018 on behalf of Lawrence Livermore National Security dated Jan. 17, 2019 9 pages.
Xiao K, et al., "Telodendrimer-based nanocarriers for the treatment of ovarian cancer." Ther Deliv, 4(10), pp. 1279-1292 (2013) 24 pages.
Alpha Helix—Wikipedia, the free encyclopedia, Nov. 7, 2014, 15 pages. https://web.archive.org/web/20141107095336/https://en.wikipedia.org/wiki/Alpha_helix.
Amar M. et al., "A Novel Apolipoprotein C-II Mimetic Peptide That Activates Lipoprotein Lipase and Decreases Serum Triglycerides in Apolipoprotein E-Knockout Mice" *The Journal of Pharmacology And Experimental Therapeutics*, 352, pp. 227-235, Feb. 2015.
Cysteine—Wikipedia, the free encyclopedia, Sep. 20, 2015, 8 pages. https://web.archive.org/web/20150920101331/https://en.wikipedia.org/wiki/Cysteine.
Donia M. et al., "Small Molecules from the Human Microbiota" *Science*, vol. 349, Jul. 24, 2015, pp. 1-25.
Final office Action for U.S. Appl. No. 15/755,018, filed Feb. 23, 2018 on behalf of Lawrence Livermore National Laboratory, dated Aug. 7, 2020. 14 Pages.
Final Office Action for U.S. Appl. No. 16/082,924, filed Sep. 6, 2018 on behalf of Lawrence Livermore National Security, LLC, dated May 21, 2020. 50 Pages.
He Y. et al., "Apolipoprotein A1 Forms 5/5 and 5/4 Antiparallel Dimers in Human High-density Lipoprotein" *Molecular & Cellular Proteomics*, 18, pp. 854-864, Jul. 2019.
Li J. et al., "Synthesis of many different types of organic small molecules using one automated process" *Science Mag*, vol. 347 isssue 6227, Mar. 13, 2015, pp. 1221-1226.
Non-Final Office Action for U.S. Appl. No. 15/755,018, filed Feb. 23, 2018 on behalf of Lawrence Livermore National Laboratory, dated Apr. 22, 2020. 57 Pages.

Notice of Allowance for U.S. Appl. No. 15/499,855, filed Apr. 27, 2017 on behalf of Lawrence Livermore National Security, LLC, dated Jun. 25, 2020. 9 pages.
Small molecule—Wikipedia, the free encyclopedia, May 12, 2015, 4 pages. https://web.archive.org/web/20150512235530/https://en.wikipedia.org/wiki/Small_molecule.
Small Molecules in Metabolomics: An Introduction. Retrieved from the web on Aug. 4, 2020.<https://www.ebi.ac.uk/training-beta/online/courses/metabolomics-introduction/what-is/small-molecules/> 2 Pages.
Barros, F., et al., "Modulation of Human erg K+ Channel Gating by Activation of a G Protein-Coupled Receptor and Protein Kinase C," The Journal of Physiology, Sep. 1998, vol. 511 (Pt 2), 333-346. 14 pages.
Bezrukov, S. M. "Functional consequences of lipid packing stress" Current Opinion in Colloid & Interface Science, 5, (2000), pp. 237-243.
Cappucchio, J., et al., "Cell-free Co-expression of Functional Membrane Proteins and Apolipoprotein, Forming Soluble Nanolipoprotein Particles," Molecular and Cellular Proteomics, Nov. 2008, vol. 7 (11), pp. 2246-2253. 8 pages.
Cleveland, T.E. IV, et al., "Small-angle X-ray and neutron scattering demonstrates that cell-free expression produces properly formed disc-shaped nanolipoprotein particles," Protein Science, Dec. 2017, vol. 27, pp. 780-789.
Denisov, I.G. et al. "Thermotropic phase transition in soluble nanoscale lipid bilayers" J Phys Chem B., (Aug. 18, 2005), 109 (32), pp. 15580-15588. 23 pages.
Dong, F., et al., "Endothelin-1 Enhances Oxidative Stress, Cell Proliferation and Reduces Apoptosis in Human Umbilical Vein Endothelial Cells: Role of ETB Receptor, NADPH oxidase and caveolin-1" British Journal of Pharmacology, Jun. 2005, vol. 145 (3), 323-333. 11 pages.
"Drug" Wikipedia, the free encyclopedia. Downloaded through the Wayback Machine for Dec. 8, 2011. 5 pages.
Dumartin, B., et al., "Dopamine Tone Regulates D1 Receptor Trafficking and Delivery in Striatal Neurons in Dopamine Transporter-Deficient Mice," Proceedings of the National Academy of Sciences of the United States of America, Feb. 2000, vol. 97 (4), 1879-1884. 6 pages.
G Protein-coupled Receptor[online], Retrieved from the Internet: URL: Wikipedia 2008, internet: web.archive.org/web/20080224232212/://en.wikipedia.org/wiki/G.protein-coupled.receptor, 2008, 7 pages.
Gantz, I., et al., "Molecular Cloning of a Gene Encoding the Histamine H2 Receptor," Proceedings of the National Academy of Sciences of the United States of America, Jan. 1991, vol. 88 (2), 429-433. 6 pages.
Hauger, R.L., et al., "Corticotropin Releasing Factor (CRF) Receptor Signaling in the Central Nervous System: New Molecular Targets," *CNS & Neurological Disorders Drug Targets*, Aug. 2006, vol. 5 (4), 49 pages.
Hong, Y., et al., "G-protein-coupled Receptor Microarrays for Multiplexed Compound Screening," *Journal of Biomolecular Screening*, Jun. 2006, vol. 11 (4), 4 pages.
Klevens, H.B. "Structure and Aggregation in Dilute Solutions of Surface Active Agents", The Journal of the American Oil Chemists' Society, (Feb. 1953), pp. 74-80.
Marsh, D. "Equation of State for Phospholipid Self-Assembly" *Biophysical Journal*, vol. 110, Jan. 2016, pp. 188-196.
Martinez, D. et al. "Lipid Internal Dynamics Probed in Nanodiscs" Chem Phys Chem, (2017) 18, pp. 2651-2657. Doi: 10.1002/cphc.201700450.
Metz, J., et al., "ACTH, α-MSH, and Control of Cortisol Release: Cloning, Sequencing, and Functional Expression of the Melanocortin-2 and Melanocortin-5 Receptor in Cyprinus Carpio," *American Journal of Physiology Regulatory Integrative and Comparative Physiology*, May 2005, vol. 289, 13 pages.
Muscarinic Acetylcholine Receptor, Retrieved from the Internet: URL://web.archive.org/web/20071020193657//https://en.wikipedia.org/wiki/Muscarinic_acetylcholine_receptor, Wikipedia 2007, 6 pages.
Non-Final Office Action for U.S. Appl. No. 15/755,018, filed Feb. 23, 2018, on behalf of Lawrence Livermore National Laboratory, dated Jul. 16, 2021. 22 Pages.

(56) References Cited

OTHER PUBLICATIONS

Non-Final Office Action for U.S. Appl. No. 16/082,924, filed Sep. 6, 2018 on behalf of Lawrence Livermore National Security, LLC dated May 25, 2021. 25 pages.
Notice of Allowance for U.S. Appl. No. 15/499,855, filed Apr. 27, 2017 on behalf of Lawrence Livermore National Security, LLC, dated May 14, 2021. 10 Pages.
Notice of Allowance for U.S. Appl. No. 15/744,754, filed Jan. 12, 2018, on behalf of Lawrence Livermore National Laboratory, dated Jul. 14, 2021. 11 pages.
Notice of Allowance for U.S. Appl. No. 16/609,420, filed Oct. 29, 2019 on behalf of Lawrence Livermore National Laboratory, dated Jul. 28, 2021. 7 Pages.
Notice of Allowance for U.S. Appl. No. 16/609,420, filed Oct. 29, 2019 on behalf of Lawrence Livermore National Laboratory, dated May 6, 2021. 10 Pages.
Pettibone, D.J., et al., "The Effects of Deleting the Mouse Neurotensin Receptor NTR1 on Central and Peripheral Responses to Neurotensin," *The Journal of Pharmacology and Experimental Therapeutics*, Jan. 2002, vol. 300 (1), 9 pages.
Pollock, N.L. et al., "Structure and function of membrane proteins encapsulated in a polymer-bound lipid bilayer", Biochimica et Biophysica Acta (BBA)—Biomembranes (Apr. 2018), vol. 1860, Issue 4, pp. 809-817. 9 pages; Internet: doi.org/10.1016/j.bbamem.2017.08.012.
Ren, X.R., et al., "Different G Protein-Coupled Receptor Kinases Govern G Protein and Beta-Arrestin-Mediated Signaling of V2 Vasopressin Receptor," *Proceedings of the National Academy of Sciences of the United States of America*, Feb. 1, 2005, vol. 102(5), 6 pages.
Schachter, I. et al. "Confinement in Nanodiscs Anisotropically Modifies Lipid Bilayer Elastic Properties", Journal of Physical Chemistry B, (Jul. 22, 2020), 1224, pp. 7166-7175.
Shaw, A.W. et al. "Phospholipid phase transitions in homogeneous nanometer scale bilayer discs", FEBS Letters 556 (2004), pp. 260-264.
Shelby M. et al., "Cell-Free Co-Translational Approaches for Producing Mammalian Receptors: Expanding the Cell-Free Expression Toolbox Using Nanolipoproteins" *Frontiers in Pharmacology*, vol. 10, No. 744, Jul. 2019, pp. 1-12.
Sligar, "Protocols for Preparation of Nanodiscs", (Mar. 4, 2008), 7 pages.
Stepien, P. et al. "Comparative EPR studies on lipid bilayer properties in nanodiscs and liposomes" Biochimica et Biophysica Acta, 1848 (2015), pp. 60-66.
Tanaka, M. et al. "Preparation and Characterization of Reconstituted Lipid-Synthetic Polymer Discoidal Particles" Langmuir, (2015), vol. 31, Issue 46, 12719-12726. 8 pages. Internet: doi.10.1021/acs.langmuir.5b03438.
Wikipedia, "5-HT Receptor," Wikipedia 2007, Retrieved from the Internet:[URL: web.archive.org/web/20071109235348/http://en.wikipedia.org/wiki/5-HT_receptor], 4 pages.
Wikipedia, Adrenergic Receptor, Internet: web.archive.org/web/20061230132111http//en.wikipedia.org/wiki/Adrenergic_Receptor, 2006, 4 pages.
Liposome—Wikipedia, the free encyclopedia. Downloaded through The Wayback Machine with a date of Dec. 31, 2015, 7 pages.
Micelle—Wikipedia, the free encyclopedia. Downloaded through The Wayback Machine with a date of Jan. 22, 2016, 5 pages.
Vesicle (biology and chemistry)—Wikipedia, the free encyclopedia. Downloaded through The Wayback Machine with a date of Jan. 23, 2016, 7 pages.
Advisory Action for U.S. Appl. No. 15/499,855, filed Apr. 27, 2017 on behalf of Lawrence Livermore National Security, LLC, dated Dec. 31, 2019. 3 pages.
De Filippis et al., "Enhanced Protein Thermostability by Ala → Aib Replacement," *Biochemistry* 1998, 37, 1686-1696. 11 Pages.
Non-Final Office Action for U.S. Appl. No. 15/744,754, filed Jan. 12, 2018 on behalf of Lawrence Livermore National Laboratory, dated Mar. 4, 2020. 53 pages.
Non-Final Office Action for U.S. Appl. No. 16/082,924, filed Sep. 6, 2018 on behalf of Lawrence Livermore National Security, LLC, dated Jan. 31, 2020. 25 pages.
Notice of Allowance for U.S. Appl. No. 15/499,855, filed Apr. 27, 2017 on behalf of Lawrence Livermore National Security, LLC, dated Mar. 5, 2020. 43 Pages.
PDB database search for oxysterol binding protein, retrieved from the Internet: <http://www.rcsb.org/pdb/results/results.do?tabtoshow=Current&qrid=37B93383>, retrieved on Feb. 20, 2020. 7 Pages.
Reinau M. et al. "The Diversity of FtsY-Lipid Interactions" *Biopolymers*, vol. 3, No. 7, Jan. 2010, pp. 595-606. 12 pages.
Ruchala et al., "Oxpholipin 11D: An Anti-Inflammatory Peptide That Binds Cholesterol and Oxidized Phospholipids," PLoS ONE, Apr. 2010, vol. 5, Issue 4, e10181. 13 pages.

METHODS AND SYSTEMS FOR PRODUCING NANOLIPOPROTEIN PARTICLES

CROSS REFERENCE TO RELATED APPLICATIONS

This application is a divisional application of U.S. application Ser. No. 12/118,396 filed on May 9, 2008, entitled "METHODS AND SYSTEMS FOR PRODUCING NANO-LIPOPROTEIN PARTICLES", which, in turn, claims priority to U.S. Provisional Application entitled "Cell-free Self Assembly of Nano-lipoprotein Particles as a Platform for Co-expressed Membrane Proteins" Ser. No. 60/928,579, filed on May 9, 2007, and to U.S. Provisional Application entitled "Monitoring IVT or Cell-free Membrane Protein Expressions, Folding and Functional Using In Situ Expression of Bacteriorhodopsin as an Internal Colorimetric" Ser. No. 60/928,573 filed on May 9, 2007, all of the disclosures of which are incorporated herein by reference in their entirety. This application may also be also related to U.S. application entitled "Methods and Systems for Monitoring Production of a Target Protein in a Nanolipoprotein Particle" filed on the same day of the presente application with No. 10/430,628, the disclosure of which is also incorporated herein by reference in its entirety.

STATEMENT OF GOVERNMENT GRANT

The United States Government has rights in this invention pursuant to Contract No. DE-AC52-06NA27344 between the United States Department of Energy and Lawrence Livermore National Security, LLC, for the operation of Lawrence Livermore National Laboratory.

TECHNICAL FIELD

The present disclosure relates to membranes and membrane associated proteins and to complexes mimicking said membranes and membrane associated proteins.

BACKGROUND

Membrane-associated proteins and protein complexes account for ~30% or more of the cellular proteins. Membrane proteins are held within a bilayer structure. The basic membrane bilayer construct consists of two opposing layers of amphiphilic molecules know as phospholipids; each molecule has a hydrophilic moiety, i.e., a polar phosphate group/derivative, and a hydrophobic moiety, i.e., a long hydrocarbon chain. These molecules self-assemble in a biological (largely aqueous) environment according to thermodynamics associated with water exclusion or hydrophobic association.

In order to facilitate the myriad functions of biological membranes including the passage of nutrients, signaling molecules and other molecules into and out of the cell, membrane proteins are arrayed in the bilayer structure as depicted below. Note that some proteins span the bilayer, others are anchored within the bilayer, and still others organize "peripheral" proteins into complexes. Many membrane bound protein complexes mediate essential cellular processes e.g. signal transduction, transport, recognition, and cell-cell communication. In general, this class of proteins is challenging to study because of their insolubility and tendency to aggregate when removed from their protein lipid bilayer environment.

Membrane proteins are optimally folded and functional when in a lipid bilayer, but standard protein purification methods often remove lipids, invariably altering protein conformation and function.

Furthermore, also non-membrane proteins (i.e. proteins that do not exercise a biological activity in connection with a location on a membrane) may still be desirably associated with a membrane for the purpose of solubilization and/or transporting and delivering to a cell.

To overcome these problems, fully functional integral membrane proteins and additional proteins can be assembled in lipid/protein-based particulate structures called nanolipoprotein particles (NLPs) usually comprising membrane forming lipids and apolipoproteins.

NLP assembly and function usually involves the association of specific apolipoprotein and lipid molecules leading to formation of proteolipid complexes; the latter are used to transport a diverse array of lipid molecules within organisms.

NLPs made in the presence of a solubilized membrane protein (target) result in a membrane protein NLP construct. Accordingly, NLP assembly can also be used for stabilization and characterization of membrane proteins.

SUMMARY

Provided herein, are methods and systems suitable for producing NLPs. In particular, in some methods and systems herein disclosed, expression of at least one of the scaffold protein and a target protein is provided for rapid assembly with a membrane forming molecule such as a lipid into an NLP nanostructure. More particular, some of the methods and systems herein disclosed allow the co-expression of the scaffold protein and target protein for assembly in a NLP, which can occur in a single reaction.

According to a first aspect a method for producing a nanolipoprotein particle is described. The nanolipoprotein particle comprises a scaffold protein and a membrane forming lipid. The method comprises: providing a polynucleotide encoding for the scaffold protein; and translating the polynucleotide in an in vitro cell-free translation system, in presence of the membrane forming lipid. In particular, the method can be performed in a single reaction ("one pot"), and the nanolipoprotein structure formed can have a discoidal structure and can form within minutes to hour after the addition of the reaction constituents. According to a second aspect, a method for producing a nanolipoprotein particle is described. The nanolipoprotein particle comprises a scaffold protein, a membrane forming lipid and a target protein. The method comprises: providing a polynucleotide encoding for the target protein; and translating the polynucleotide in an in vitro cell free translation system, in presence of the scaffold protein and the membrane forming lipid.

According to a third aspect, a method for producing a nanolipoprotein particle is described. The nanolipoprotein particle comprises a scaffold protein, a membrane forming lipid and a target protein. The method comprises: providing a first polynucleotide encoding for the scaffold protein; providing a second polynucleotide encoding for the target protein; and translating the first polynucleotide and the second polynucleotide in an in vitro cell free translation system, in presence of the membrane forming lipid.

According to a fourth aspect, a system for producing a nanolipoprotein particle is described. The nanolipoprotein particle comprises a scaffold protein and a membrane forming lipid. The system comprises: the membrane forming lipid; and a polynucleotide encoding for the scaffold protein.

The system is configured to be operated in connection with an in vitro cell free translation system for the translation of the polynucleotide in presence of the membrane forming lipid.

According to a fifth aspect a system for producing a nanoliprotein particle is described. The nanolipoprotein particle comprises a scaffold protein, a membrane forming lipid and a target protein. The system comprises: at least one of the membrane forming lipid and the scaffold protein; and a polynucleotide encoding for the target protein. The system is configured to be operated in connection with an in vitro cell free translation system for the translation of the polynucleotide in presence of the membrane forming lipid and of the scaffold protein.

According to a sixth aspect, a system for producing a nanoliprotein particle is described. The nanolipoprotein particle comprises a scaffold protein, a membrane forming lipid and a target protein. The system comprises: a first polynucleotide encoding for the scaffold protein; and a second polynucleotide encoding for the target protein. The system is configured to be operated in connection with an in vitro cell free translation system for the translation of the first and second polynucleotide in presence of the membrane forming lipid.

Provided herein are also methods and systems for producing NLPs with an increased solubility, with a controlled size and/or of a predetermined dimensions so to include a predetermined target protein.

According to one aspect, a method for producing a nanolipoprotein particle is described. The nanolipoprotein particle comprises a scaffold protein a membrane forming lipid and optionally a target protein. The method comprises: contacting the scaffold protein and the membrane lipid and optionally the target protein for a time and under conditions to allow self assembly of said protein component and said membrane lipid. The scaffold protein and the membrane lipid are contacted in a mass ratio of about 3:1 to about 6:1

According to a further aspect a method for producing a nanolipoprotein particle of a predefined size is described. In particular a method to produce a nanolipoprotein having a size from 10 to 60 mn is disclosed. The nanolipoprotein particle comprises a scaffold protein and a membrane forming lipid. The method comprises: mixing the scaffold protein and the membrane forming lipid at a mass ratio of scaffold protein to membrane forming lipid from about 3:1 to about 4:1.

According to a still an additional aspect, a method for producing a nanolipoprotein particle suitable to include a predetermined target protein is described. The nanolipoprotein particle comprises a scaffold protein and a membrane forming lipid, the method comprises mixing the scaffold protein, the membrane forming lipid and the target protein at a final mass ratio of scaffold protein:membrane forming lipid:target protein of about 4:1:6.

The methods and systems herein described can be used for the production of target proteins, and in particular membrane proteins for structural and functional characterization.

The methods and systems herein described can be also used for producing selected integral membrane proteins for biophysical characterization.

The methods and systems herein described can be further used as an additive to cell free expression methods and systems in applications that are independent from the organism/system used to generate the cell free extract.

The methods and systems herein described can additionally be used for the efficient production of membrane proteins, with particular reference to the membrane proteins difficult to produce from native systems.

The methods and systems herein described can also be used in processes for screening parameters for evaluation of production of any insoluble protein such as membrane proteins.

The methods and systems herein described can be applied in several fields including basic biology research, applied biology, bio-engineering, bio-energy, medical research, medical diagnostics, therapeutics, and bio-fuels.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description, serve to explain the principles and implementations of the disclosure.

FIG. 26A shows a schematic illustration of specific immobilization of proteins on a chemically modified solid support through the use of intein mediated protein transsplicing. Panel B FIG. 26B shows a schematic illustration of structures for the linkers 1 (comprising SEQ ID NO: 14) and 2 that are used for derivation of the surface on the glass slides.

FIG. 30 shows a SYPRO® RUBY-stained native PAGE indicating molecular size and relative homogeneity of NLPs prepared from four different apolipoproteins without cholate according to an embodiment herein disclosed.

FIG. 31 shows a diagram illustrating ion mobility traces of mean aerodynamic diameter size distributions for four NLP preparations obtained according to an embodiment herein disclosed.

DETAILED DESCRIPTION

Figure 1:
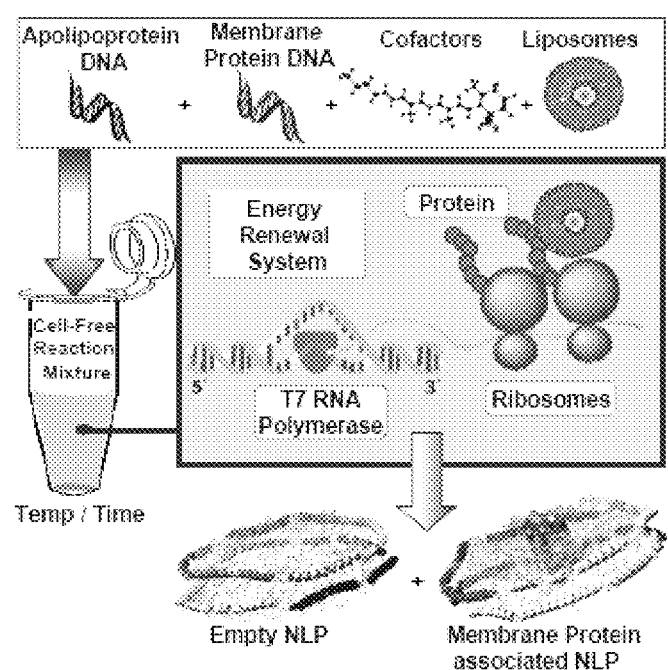
FIG. 1 shows a schematic illustration of single step cell-free co-expression and stabilization of integral membrane proteins using an apolipoprotein according to an embodiment herein described.

Methods and systems for production of NLPs are disclosed. In the methods and systems herein disclosed expression of at least one protein of the protein component of a NLP is performed in a cell-free method/system in presence of other NLPs components for a time and under conditions that allow assembly of the NLP.

The term "nanolipoprotein particle" 'nanodisc" "rHDL" or "NLP" as used herein indicates a supramolecular complex formed by a membrane forming lipid and a scaffold protein. In some embodiments the NLP can also include a target protein. In some embodiments, the nanolipoprotein particle can have a discoidal structure. The scaffold protein and, optionally, the target protein constitute protein components of the NLP. The membrane forming lipid constitutes a lipid component of the NLP.

The term "protein" as used herein indicates a polypeptide with a particular secondary and tertiary structure that can participate in, but not limited to, interactions with other biomolecules including other proteins, DNA, RNA, lipids, metabolites, hormones, chemokines, and small molecules.

The term "polypeptide" as used herein indicates an organic polymer composed of two or more amino acid monomers and/or analogs thereof. Accordingly, the term "polypeptide" includes amino acid polymers of any length including full length proteins and peptides, as well as analogs and fragments thereof. A polypeptide of three or more amino acids can be a protein oligomer or oligopeptide.

As used herein the term "amino acid", "amino acidic monomer", or "amino acid residue" refers to any of the twenty naturally occurring amino acids including synthetic amino acids with unnatural side chains and including both D and L optical isomers. The term "amino acid analog" refers to an amino acid in which one or more individual atoms have been replaced, either with a different atom, isotope, or with a different functional group but is otherwise identical to its natural amino acid analog The term "scaffold protein" as used herein indicates any protein that is capable of self assembly with an amphipatic lipid in an aqueous environment, organizing the amphipatic lipid into a bilayer, and include but are not limited to apolipoproteins, lipophorines, derivatives thereof (such as truncated and tandemly arrayed sequences) and fragments thereof (e.g. peptides), such as apolipoprotein E4, 22K fragment, liphorin III, apolipoprotein A-1 and the like. In particular, in some embodiments rationally designed amphipathic peptides can serve as a protein component of the NLP.

In some embodiment, the peptides are amphipatic helical peptides that mimic the alpha helices of a apolipoprotein component that are oriented with the long axis perpendicular to the fatty acyl chains of the amphipatic lipid and in particular of the phospholipid The term "target protein" as used herein indicates any protein having a structure that is suitable for attachment to or association with a biological membrane or biomembrane (i.e. an enclosing or separating amphipathic layer that acts as a barrier within or around a cell). In particular, target proteins include proteins that contain large regions or structural domains that are hydrophobic (the regions that are embedded in or bound to the membrane); those proteins can be extremely difficult to work with in aqueous systems, since when removed from their normal lipid bilayer environment those proteins tend to aggregate and become insoluble. In particular, target proteins include but are not limited to membrane proteins, i.e. proteins that can be attached to, or associated with the membrane of a cell or an organelle, such as integral membrane proteins (i.e. proteins (or assembly of proteins) that are permanently attached to the biological membrane), or peripheral membrane proteins (i.e. proteins that adhere only temporarily to the biological membrane with which they are associated). Integral membrane proteins can be separated from the biological membranes only using detergents, nonpolar solvents, or sometimes denaturing agents. Peripheral membrane proteins are proteins that attach to integral membrane proteins, or penetrate the peripheral regions of the lipid bilayer with an attachment that is reversible.

The term "membrane forming lipid" or "amphipatic lipid" as used herein indicates a lipid possessing both hydrophilic and hydrophobic properties that in an aqueous environment assemble in a lipid bilayer structure that consists of two opposing layers of amphipathic molecules know as polar lipids. Each polar lipid has a hydrophilic moiety, i.e., a polar group such as, a derivatized phosphate or a saccharide group, and a hydrophobic moiety, i.e., a long hydrocarbon chain. Exemplary polar lipids include phospholipids and alkylphosphocholins. Amphipatic lipids include but are not limited to membrane lipids, i.e. amphipatic lipids that are constituents of a biological membrane, such as phospholipids like dimyrisoylphosphatidylcholine (DMPC) or Dioleoylphosphoethanolamine (DOPE) or dioleoylphosphatidylcholine (DOPC).

The membrane forming lipid and the protein components of the NLP are generally able to self-assemble in a biological (largely aqueous) environment according to the thermodynamics associated with water exclusion (increasing entropy) during hydrophobic association. In the methods and systems herein provided, the amphipatic lipid and the protein components of the NLP are allowed to assembly in a cell free expression system.

As used herein, "the wording cell free expression", "cell free translation", "in vitro translation" or "IVT" refer to at least one compound or reagent that, when combined with a polynucleotide encoding a polypeptide of interest, allows in vitro translation of said polypeptide/protein of interest.

The term "polynucleotide" as used herein indicates an organic polymer composed of two or more monomers including nucleotides, nucleosides or analogs thereof. The term "nucleotide" refers to any of several compounds that consist of a ribose (ribonucleotide) or deoxyribose (deoxyribonucleotides) sugar joined to a purine or pyrimidine base and to a phosphate group, and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers respectively to a nucleotide or nucleoside in which one or more individual atoms have been replaced with a different atom or a with a different functional group. Accordingly, the term polynucleotide includes nucleic acids of any length DNA RNA analogs and fragments thereof. A polynucleotide of three or more nucleotides is also called nucleotidic oligomers or oligonucleotide.

In some embodiments, the polynucleotide is an engineered polynucleotide designed such that the resulting protein may be expressed as a full-length protein. In some embodiments the polynucleotide is an engineered polynucleotide designed to encode a protein fragment. Protein fragments include one or more portions of the protein, e.g. protein domains or subdomains. In some embodiments the polynucleotide is an engineered polynucleotide designed to encode a mutated proteins. In particular, in some embodiments the polynucleotide can also be designed such that the resulting protein, protein fragment or mutated protein is expressed as a fusion, or chimeric protein product (i.e. it is joined via a peptide bond to a heterologous protein sequence of a different protein), for example to facilitate purification or detection. A chimeric product can be made by ligating the appropriate nucleic acid sequences encoding the desired amino acid sequences to each other using standard methods and expressing the chimeric product. In particular, in some embodiments wherein the polynucleotide encodes for a target protein, the polynucleotide can be engineered so that target protein are labeled or tagged. Labeling or tagging can be performed with methods that include, for example, FRET pairs, NHS-labeling, fluorescent dyes, and biotin as well as coding for a "His-tag" to enable protein isolation and purification via established Ni-affinity chromatography.

In some embodiments herein disclosed, the polynucleotide is a DNA molecule that can be in a linear or circular form, and encodes the desired polypeptide under the control of a promoter specific to an enzyme such as an RNA polymerase, that is capable of transcribing the encoded portion of the DNA.

In embodiments where the polynucleotide is DNA, the DNA may be transcribed as part of the cell free reactions or system. In those embodiments the DNA contains appropriate regulatory elements, including but not limited to ribosome binding site, T7 promoter, and T7 terminator, and the reagents or compounds include appropriate elements for both transcription and translation reactions. In other embodiments, the polynucleotide can be prepared prior to addition to the cell free reactions/system, wherein the polypeptide of interest is produced, and the reagents or compounds include appropriate elements for and translation reactions only.

Accordingly, as used herein, the term "cell free expression", "cell free translation", "in vitro translation" or "IVT" refer to methods and systems wherein the transcription and translation reactions are carried out independently, and to systems in which the transcription and translation reactions are carried out simultaneously in a non-cellular compartment, e.g. glass vial.

In each of these methods and systems, the reagents or compounds typically include a cell extract capable of supporting in vitro transcription and/or translation as appropriate. In any case, the cell extracts must contain all the enzymes and factors to carry out the intended reactions, and in addition, be supplemented with amino acids, an energy regenerating component (e.g. ATP), and cofactors, including factors and additives that support the solubilization of the protein of interest.

These systems are known in the art and can be identified by the skilled person upon reading of the present disclosure, and exist for both eukaryotic and prokaryotic applications. Exemplary cell free expression systems that can be used in connection with the methods and systems of the present disclosure includes but are not limited to commercial kits for various species such as extracts available from Invitrogen Ambion, Qiagen and Roche Molecular Diagnostics, cellular extracts made from *E. coli* or wheat germ or rabbit reticulocytes, or prepared following protocols, such as published laboratory protocols, identifiable by a skilled person upon reading of the present disclosure.

In some embodiments, the cell free system can operate in batch mode or in a continuous mode. In the batch mode the reaction products remain in the system and the starting materials are not continuously introduced. Therefore, in batch mode, the system produces a limited quantity of protein. In a continuous mode instead, the reaction products are continuously removed from the system, and the starting materials are continuously restored to improve the yield of the protein products and therefore the system produces a significantly greater amount of product.

In some embodiments, the cell free expression system is a high-throughput expression system, where an array (i.e., at least two) of polynucleotides (coding for the same or different polypeptides) is processed simultaneously in multi-well reaction plates, where each polynucleotide is in a well of the plate. The reaction plate can typically have at least 2 wells, and typically has 12-, 24-, 96-, 384-, or 1536-wells; other sizes may also be used.

In some of those embodiments the array is carried out to explore the function and potential relationships of proteins encoded within any genome.

In some of those embodiments the array is carried out for parallel analysis of multiple binary interactions between proteins and other molecules. In addition, in some embodiments engineering and tagging techniques allows the orientation of proteins of interest and expands the capabilities and use of protein microarrays. Some of those embodiments wherein cell-free expression is combined with array-based proteomics are applicable in particular in protein biochemistry, molecular diagnostics and therapeutics.

In some embodiments array-based methods and systems provide a high-throughput format with which to investigate protein-protein, protein-DNA, and protein-small molecule interactions on the NLP.

In some embodiments, the scaffold protein is expressed in the cell free reaction system where the amphipatic lipid and, optionally, the target protein are also included. In those embodiments the cell free reaction is performed for a time and under conditions that allow the expression of scaffold protein and the assembly of the scaffold protein with the amphipatic lipid and optionally the target protein in an NLP structure.

In some embodiments, the target protein is expressed in the cell free reaction system where the amphipatic lipid and the scaffold protein are also included. In those embodiments the cell free reaction is performed for a time and under condition that allow the expression of target protein and the relevant assembly with the scaffold protein and the amphipatic lipid in an NLP structure.

In some embodiments, the target protein is expressed in the cell free reaction system where a preformed NLP is included. In those embodiments addition of pre-formed NLPs to an actively expressing cell-free protein synthesis reaction is performed for a time and under condition to allow direct insertion of membrane protein as it is synthesized in the cell-free system, into the NLP.

In some embodiments, the target protein and/or scaffold protein are expressed or co-expressed in a cell free system wherein both kinds of proteins can be expressed in a single reaction (one-pot) in a system that can include the appropriate additives directed to facilitate reactant solubilization. In those embodiments, the co-expressed target protein and scaffold protein are then allowed to assembly of membrane proteins into NLP nanostructures; possibly within the same reaction mixture. Some of those embodiments allow producing NLPs overcoming the requirement for the purification and reassembly of the NLP complex. Some of those embodiments also provides a single-step process for the production of soluble membrane proteins that eliminates the need for cell growth, cell lysis, and subsequent purification, refolding. Some of those embodiments allow avoiding use of detergents while allowing single-step addition of lipids and other molecules important to protein function.

In particular, co-expression of both scaffold protein and target membrane protein in presence of phospholipids and surfactant/detergent can be performed in a "one-pot" reaction that generates, in situ, both scaffold protein and target membrane protein; NLP self-assembly will ensue using phospholipids already in the reaction mixture. Some of those embodiments are exemplified by the co-expression of a truncated apolipoprotein (Ll-ApoAl) and the bacteriorhodopsin gene, which results in the functionally active seven transmembrane helix bacteriorhodopsin protein (bR) upon addition of retinal cofactor as illustrated in Examples 1-15 and in FIGS. 1-28.

In embodiments, wherein the methods and systems performed in a "one-pot" solution the nanolipoprotein structure can be formed in a rapidly e.g. within minutes to hour after the addition of the reaction constituents.

In some embodiments, each of the target protein and/or the scaffold protein expressed in the IVT system is comprised of more than one protein, thus resulting in NLP including two or more target proteins and/or two or more scaffold proteins. In particular, in some of those embodiments cell-free co-expression of membrane proteins in NLP complexes enable production in a same NLP of multiple classes of membrane associated proteins previously not conveniently obtainable.

In some embodiments the target proteins are membrane proteins such as protein coupled receptors (GPCRs), which include, for example acetylcholine receptors (AChRs) and rhodopsin. GPCRs conform to a shared common structure that is believed to traverse the cell surface membrane seven times forming a helical structure encompassing a ligand binding site. Of the three cytoplasmic dominions the C-loop has a C-terminal tail that recognized and activates specific hetero-trimeric GTP binding proteins (G proteins) in an agonist dependent manner.

Further exemplary target proteins include Ion channels (IC) and small multidrug resistance transporter (SMR), and additional membrane proteins that mediate essential cellular processes including signal transduction, transport, recognition, bioenergetics, and cell-cell communication. This would include G-coupled receptors, Toll receptors and various kinases that important for the aforementions processes For example possible target proteins include membrane proteins from *Thiobacillus denitrificans* such as unusual membrane associated [NiFe] hydrogenase complex, a group of highly expressed membrane bound c-type cytochromes and a group of highly unregulated membrane proteins of unknown functions.

Exemplary GPCRs suitable to be used as target proteins in the methods and systems herein disclosed are indicated in Table 1.

Table 1: Exemplary Target Proteins

TABLE 1

| | | | | Exemplary target proteins | | | |
|---|---|---|---|---|---|---|---|
| | CB | FL | CF | Target | Endogenous ligand | Family | Fluorescent ligand | Availability |
| 1 | X | X | X | V2R | Vasopressin | GPCR | FAM-Vasopressin | commercial |
| 2 | X | X | X | CFR | Corticotropin RFI (CRF) | GPCR | FAM/Rhod-CRF | commercial |

TABLE 1-continued

Exemplary target proteins

| | CB | FL | CF | Target | Endogenous ligand | Family | Fluorescent ligand | Availability |
|---|---|---|---|---|---|---|---|---|
| 3 | X | X | X | ETB | Endothelin | GPCR | FAM/Rhod-Endothelin | commercial |
| 4 | X | X | X | MC5R | Melanocortin | GPCR | BODIPY-TMR NDP-α-MSH | commercial |
| 5 | V | X | X | NTR1 | Neurotensin | GPCR | FAM-neurotensin | commercial |
| 6 | X | S | | 5HT1A | Serotonin | GPCR | | synthesize |
| 7 | X | S | | D1 | Dopamine | GPCR | | synthesize |
| 8 | X | S | | H2 | Histamine | GPCR | | synthesize |
| 9 | X | X | | M1 | Acetylcholine/Muscarine | GPCR | FITC-pirenzapine | commercial |
| 10 | X | X | | hERG | Voltage | IC | IVGN-0107 | synthesize |
| 11 | | X | | α1AR | Epinephrine | GPCR | BODIPY FL prazosin | commercial |
| 12 | | X | | β1AR | Epinephrine | GPCR | BT-CGP12177 | commercial |
| 13 | V | X | | OP1R | Opiods | GPCR | FL-naltrexone/naloxone | commercial |
| 14 | | | X | β2AP | Epinephrine | GPCR | | synthesize |
| 15 | V | | X | M2 | Acetylcholine/Muscarine | GPCR | | synthesize |

CB = Cell Based Assay available (X = CBA exists, V = vector exists for assay in development)
FL = Fluorescent Ligand available (X = Yes, S = requires synthesis)
CF = Expressed in Cell-Free system In particular, bacteriorhodopsin (bR) from *H. salinarium*, is further exemplary target protein having 7 transmembrane spanning regions that can be produced, purified and regenerated by exogenously adding all-trans retinal. bR was used in a series of experiments exemplified in the Examples section as a model target protein to be included in NLPs according to methods and systems herein disclosed. Additional target proteins that can be included in the NLPs according to the methods and systems herein disclosed can be identified by a skilled person upon reading of the present disclosure and will not be further discuss in details.

In general, target proteins that can advantageously be included in NLP using methods and systems herein disclosed, comprise all the proteins and in particular membrane protein, whose over-expression results in cell toxicity (in vivo), protein aggregation, mis-folding, and low yield and that are instead expressed in a cell free system that includes appropriate additives.

In some embodiments, the additives used in the cell free reaction systems include any substance that improves the solubilization of the protein of interest and/or of any other protein components that are present in the reaction mixtures, any substance that may augment protein production and any substance that improves protein functions. Those additives include but are not limited to cofactors (e.g. retinal, heme) other proteins that facilitate modification (e.g. glycosylases, phosphatases, chaperonins) lipids, redox factors, detergents and protease inhibitors, and in particular, phospholipids such as dimyristoylphosphatidyl choline (DMPC) and the like, and surfactants/detergents such as cholate, triton X-100 and the likes. Exemplary detergents that can be used for protein solubilization in the methods and systems herein disclosed, include Heptanoyl-N-methyl-glucamide, Octanoyl-N-methyl-glucamide, Nonanoyl-N-methyl-glucamide, n-Nonyl-b-D-gluco-pyranoside, N-Octyl-b-D-glucopyranoside, Octyl-b-D-thiogluco-pyranoside, NN-Dimethyldodecylamine-N-oxide and Glycerol. Additional additives that might be included in the reaction mixtures include labels and labelling molecule that can be used to label or tag the target protein and thus to enable the detection of the target protein through detection of a related labeling signal.

The terms "label" and "labeled molecule" as used herein refer to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence the wording and "labeling signal" as used herein indicates the signal emitted from the label that allows detection of the label, including but not limited to radioactivity, fluorescence, chemoluminescence, production of a compound in outcome of an enzymatic reaction and the likes.

In some embodiments, the methods and systems herein disclosed are used to produce proteins for structural studies, including for example NMR and X-ray crystallography. In particular, these cell free methods can be applied to integral membrane proteins in a high-throughput manner, as a variety of conditions can be rapidly tested to identify optimal expression parameters.

In some embodiments, the methods and systems herein disclosed are used to produce NLPs suitable as drug delivery vehicles, wherein the particles are formed by taking advantage of the ability of amphipathic apolipoproteins to solubilize certain phospholipids vesicle substrates, transforming them into a relatively homogeneous population of disk-shaped bilayers whose perimeter is circumscribed by apolipoprotein molecules.

In some embodiments, NLPs are provided by the methods and systems herein disclosed by using different scaffold proteins, which allows tailoring the average size of the particles, e.g. from 10 to 60 nm (+/−3%), and in particular 10 to 30 mn (+/−3%) at an average height of 5.0 nm. The nanoscale bilayers so obtained can be used to investigate and control assembly of oligomeric integral membrane proteins critical to macromolecular recognition and cellular signaling. Those embodiments can be performed using any apolipoprotein-like molecules as potential structure for solubilizing the membrane proteins via NLP formation. Examples include, but are not limited to ApoE4, ApoAI, MSPI (ApoAI truncations), synthetic peptides and insect lipophorins.

In some embodiments, methods and systems are herein disclosed that are performed at predefined lipid protein ratio, assembly conditions and/or with the use of preselected protein component and amphipatic lipid so to increase the yield, control the size of the resulting NLP and/or provide an NLP of pre-determined dimensions so to include a pre-determined target protein.

In some embodiments, for obtaining an increased solubility the scaffold protein and the membrane lipid are contacted in a mass ratio of about 3:1 to about 6:1 and in particular of about 4:1 to about 6:1, more particularly of about 4:1 to about 5:1 and of about 5:1 to about 6:1.

In some embodiments the scaffold protein is selected to define the size of NLPs. In particular, the scaffold protein and/or the membrane forming lipid can be selected so that the scaffold protein and the membrane forming lipid are contacted lipid at a mass ratio of scaffold protein to membrane forming lipid from about 3:1 to about 4:1 to provide a particle having a size from 10 to 60 mn. In some embodiments, Lipophorin III lipoproteins make assemble into larger NLPs with diameters 10-30 nm range, apolipoprotein A1 NLPs range in size from 10-25 nm, truncated Δ(1-49) Apolipoprotein A1 15-35 nm. Adjustment of protein to lipid ratios increasing lipid will also increase the size of the NLP. An exemplary, procedure is illustrated in the examples section.

In some embodiments the amphipatic lipid is tested to provide the most stable and native-like environment. For example a target protein that is naturally found in the inner mitochondrial membrane would contain lipids specific to that region of the cell. In particular the protein of the inner mitochondrial membrane requires a membrane compose of ~20% cardiolipin for proper function. A protein that requires more flexibility in it function may require lipids with a higher degree of unsaturation creating a bilayer with more fluidity. While incorporating a target protein the stability of the protein may be improve by using a detergent that has been proven to allow the protein to retain native activity as measured/monitored by our indicator protein.

In some embodiments, the target protein scaffold protein and membrane forming lipid are added in certain proportion to provide a nanolipoprotein particle configure to include a predetermined target protein. The method typically comprises contacting the reactant to obtain a particle with a controlled size (see e.g. Example 30) with the addition of membrane protein, e.g. bacteriorhodopsin as a crude "purple membrane" completing a final mass ratio apolipoprotein:phospholipid:membrane protein of about 4:1:6

In some embodiments the amphipatic lipid is selected to resemble the native lipid composition in which the membrane protein is known to function.

In some embodiments the lipid to scaffold protein ratio: is selected to optimize and maximize the yield leading to NLP formation.

In some embodiments the assembly parameters are selected to allow the constituents reach maximum NLP formation reflective of a thermodynamic endpoint.

The systems herein disclosed can be provided in the form of kits of parts. In some embodiments, the characteristic feature size can be micrometers. The target protein and/or the scaffold protein can be included in the kit as a protein alone or in the presence of lipids/detergents for transition in to nano-particles. The target protein and/or the scaffold protein can be included as a plasmid or PCR DNA product for transcription/translation. The indicator protein may be included as encoded RNA for translation In a kit of parts, a polynucleotide, amphipatic lipid, target protein and/or scaffold protein are comprised in the kit independently possibly included in a composition together with suitable vehicle carrier or auxiliary agents. For example a polynucleotide—can be included in one or more compositions alone and/or included in a suitable vector, and each polynucleotide—is in a composition together with a suitable vehicle carrier or auxiliary agent. Furthermore, the target protein can be included in various forms suitable for appropriate incorporation into the NPL. For example, in embodiments wherein the target protein is bR, the cofactor all-trans-retinal would be included in a kit that also contained the encoded genetic information for the production of bacteriorhodopsin as the target protein.

In some embodiments, a ligand suitable to bind a target protein of interest can be further provided as an additional component of the kit. Additional components can include labeled polynucleotides, labeled antibodies, labels, microfluidic chip, reference standards, and additional components identifiable by a skilled person upon reading of the present disclosure. In particular, the components of the kit can be provided, with suitable instructions and other necessary reagents, in order to perform the methods here disclosed. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like).

Further details concerning the identification of the suitable carrier agent or auxiliary agent of the compositions, and generally manufacturing and packaging of the kit, can be identified by the person skilled in the art upon reading of the present disclosure.

EXAMPLES

The methods and system herein disclosed are further illustrated in the following examples, which are provided by way of illustration and are not intended to be limiting.

Example 1: Cell-Free Production of NLPs

The experimental strategy for cell-free membrane protein-NLP self-assembly was based on the ability of membrane proteins to insert into lipid bilayers during cell-free synthesis, the apolipoprotein ability to sequester lipid bilayer patches, and the demonstrated ability of NLPs to than solubilize membrane proteins. Individual plasmid DNAs encoding the membrane protein and the apolipoprotein are added to the cell-free reaction with the addition of phospholipids and cofactors to produce membrane protein associated discoidal nanolipoprotein particles (NLPs) in a single reaction. In particular, as shown in FIG. 1 constituents (DNA, lipid vesicles, cofactors and cell-free lysates) are added together in a single reaction vial. The cell-free lysates take advantage of the T7 coupled transcription and translation system to produce a mixed population of self-assembled NLPs with and without associated integral membrane protein.

In a first series of experiments, two plasmids were used to generate the integral membrane protein and the lipoprotein NLP support, one encoding membrane protein bacterioOpsin (bOp) and the second encoding a Δ1-49 apolipoprotein A-1 fragment (Δ49A1). The plasmids were co-expressed, in the presence of all-trans-retinal and the phospholipid dimyristoyl-phosphatidylcholine (DMPC), resulting in functional bacteriorhodopsin (bR) protein solubilized in a discoidal bR-NLP.

In particular, the truncated form of Apo A1 (Δ1-49) or Δ49A1 was cloned using the following primers: forward, 5'-atgctaaagctccttgacaactgg-3' (SEQ ID NO: 1) and reverse, 5'-ttactgggtgttgagcttcttagtg-3' (SEQ ID NO: 2). This construct is six amino acids shorter than our truncated form of Apo A1 (Δ1-49) or Δ49A1, and was expected to perform similarly in NLP assembly and characterization.

The resulting PCR product was cloned into the vector pIVEX2.4d using NdeI and SmaI restriction sites. This vector also contains a His-tag for nickel affinity purification. The bacterioOpsin sequence (bOp), which encodes the bacteriorhodopsin protein, was amplified from a plasmid p72bop (Sonar et al., 1993; obtained from Kenneth Rothschild) using the following primers: 5'-ggggcatatgcaagctcaaat-3' (SEQ ID NO: 3) and 5'-ggggatccaaaaaaaacgggcc-3' (SEQ ID NO: 4). The gene represents a synthetic form of bOp that was designed for *E. coli*-based expression (1). The resulting PCR product was cloned directionally into the HIS-tagged pIVEX 2.4b vector using the NdeI and BamHI restriction enzyme sites. All constructs were verified by DNA sequencing.

Cell-free reactions were then performed. In particular, preparative reactions are carried out using the Invitrogen's Expressway Maxi kit or Roche's RTS 500 ProteoMaster Kit. Basically, lyophilized reaction components (Lysate, Reaction Mix, Amino Acid Mix, Methionine) are dissolved in Reconstitution Buffer and combined as specified by the manufacturer. For co-expression a total of 5 μg of each plasmid DNA (bOp and Δ49A1) was added to the lysate mixture with added DMPC vesicles and retinal cofactor (see below). The reactions were incubated at 30° C. or 37° C. for 4-24 h. For membrane protein survey studies co-expression of 0.2 ug Δ49A1 DNA and 1 ug of each membrane protein DNA was added to the cell-free mixture where [$^{35}$S]Met (135 mCi/mmol final) (Perkin Elmer, Waltham, Mass.) was added in place of methionine. The soluble fraction was obtained by centrifuging the reactions at 14000×g for 5 min. Autoradiograms were generated by overnight exposures to proteins separated by SDS-PAGE (data not shown). Percent solubility was determined using ImageJ software (U. S. National Institutes of Health) to quantize autoradiogram bands for the soluble fractions in the presence and absence of apolipoprotein Δ49A1.

In some reactions a retinal cofactor was added. To this purpose, an all trans-retinal (Sigma) solution was prepared with 100% ethanol at a stock concentration of 0.586 or 10 mM. The stock solution was diluted to achieve a final working concentration of 30-50 μM in cell-free reactions.

The lipid component of the NLPs was also prepared. Small unilamellar vesicles of DMPC (liposomes) were prepared by probe sonicating a 68 mg/mL aqueous solution of DMPC until optical clarity is achieved; typically 15 min on ice is sufficient. A 2 min. centrifugation step at 13700 RCF was used to remove any metal contamination from the probe tip. The individual lipid component was added to the cell-free reaction at a concentration of 2 mg/mL.

Soluble fractions were purified. In particular, NLP complexes were then purified through Affinity purification. In particular, immobilized metal affinity chromatography was used to isolate the proteins of interests (truncated 49A1 and bOp) from the cell-free reaction mixture based on affinity of the N-terminal poly-His tag. The soluble fraction was separated from precipitated protein by centrifugation for 5 min at 18K RCF at 4° C. The soluble fraction was mixed with Ni-NTA Superflow resin (Qiagen) according to the manufacturer's protocol using native purification conditions with the following modifications; 5 mM imidazole in PBS buffer was used for washing and 400 mM imidazole PBS buffer was used for elution of the His-tagged proteins. All elutions were combined, concentrated and buffer exchanged into TBS using a 100K MWCO molecular weight sieve filters (Vivascience) in a volume of 200 μL.

The samples were also characterized by SDS-PAGE, Native PAGE, UV-visible spectroscopy, and atomic force microscopy (AFM) as illustrated in the following examples. A survey study of other membrane proteins co-expressed with the truncated apolipoprotein also significantly increased solubility all of the membrane proteins surveyed Example 2: Characterization of NLPs Produced by Cell-Free System: Solubilization of the bR-NLP Complex The experimental design outlined in Example 1 of cell-free co-expression for refolding and incorporation into NLPs was also demonstrated using bR from *Halobacterium salinarium*, and truncated apolipoprotein A-1 (Δ1-49) or Δ49A1. The bR protein is a seven transmembrane (TM) helical protein and serves as a structural model protein for rhodopsin and other 7-TM proteins such as GPCR family members.

Figure 2:
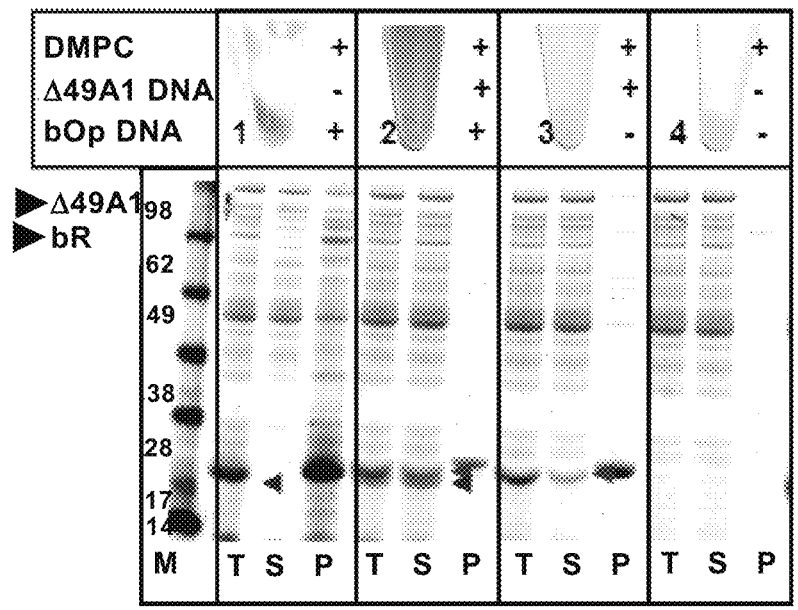
FIG. 2 shows single-step production, purification and characterization of MP-NLP complexes, according to an embodiment herein described. a. Coomassie stained SDS-PAGE gel image of Total (T), Soluble (S) and Pellet (P) fractions from cell-free produced bacteriorhodopsin (bR) in the presence and absence of co-expressed apolipoprotein (Δ49A1). A (+) indicates the addition of either DMPC, Δ49A1 DNA or bacteriOpsin DNA (bOp) to the cell-free reaction, (−) denotes absence of additive. Grey arrows indicate Δ49A1 (lane 2S upper arrow and lane 3S), and black arrows indicate bR (lane 1T and lane 2S lower arrow). Sample 1 indicates bOp & DMPC; Sample 2 indicates bOp, Δ49A1 co-expressed in the presence of DMPC; Sample 3 indicates Δ49A1 & DMPC; Sample 4 indicates the control cell-free reaction (No DNA) in the presence of DMPC only.
Figure 3:
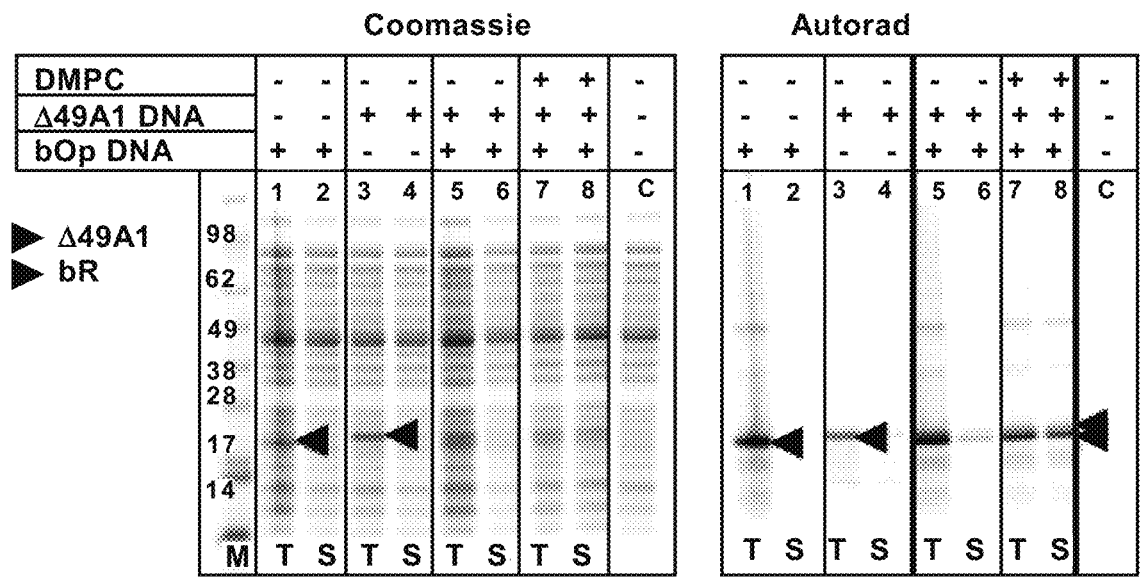
FIG. 3 shows solubility of cell-free produced bR-NLPs. The (+) indicates the addition of either DMPC, Δ49A1 DNA or bacteriOpsin DNA (bOp) to the cell-free reaction, (−) denotes absences of additive, all were expressed in the presence of 50 μM all-trans-retinal. a. Solubility of bR is increased in the presence of Δ49A1 DNA. Cell-free reactions were carried out in the presence of $^{35}$S-Methionine. Grey arrows indicate Δ49A1 (Coomassie: lane 3; Autorad: lanes 3 and 8 upper arrow), and black arrows indicate bR (Coomassie: lane 1; Autorad: lanes 1 and 8 lower—in Autorad). Left Panel, Coomassie stained SDS-PAGE gel image of total (T) and soluble (S) fractions from cell-free produced bR in the presence and absence of co-expressed apolipoprotein (Δ49A1) and DMPC. Right Panel, Autoradiogram of the gel shown in left panel, illustrating the benefit of adding the apolipoprotein for increasing the solubility of b.R

Simultaneous cell-free protein expression of both bR and Δ49A1 in the presence of DMPC in a single reaction produces a functional bR-NLP complex (FIG. 2 and FIG. 3).

In particular, as illustrated in FIG. 2, bOp & DMPC (sample 1) shows bR is insoluble in the absence of co-expression of Δ49A1; bOp, Δ49A1 co-expressed in the presence of DMPC (sample 2) shows bR remains in the soluble fraction with co-expressed Δ49A1; Δ49A1 & DMPC (sample 3) shows production of "empty"-NLPs; the control (sample 4) shows cell-free reaction (No DNA) in the presence of DMPC only. All were expressed in the presence of 30-50 μM all-trans-retinal and 2 mg/mL DMPC. Purple color development observed in sample 1 and 2 indicates incorporation of retinal into the bOp transcript representing proper folding of bR.

Figure 4:
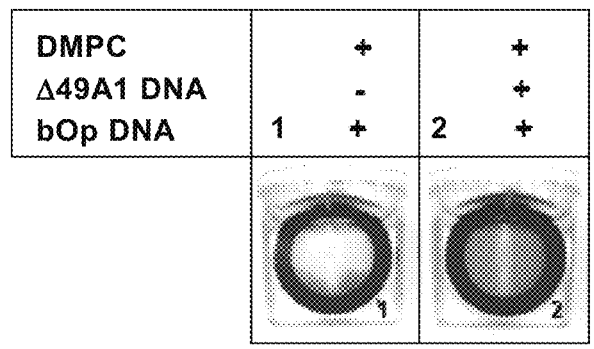
FIG. 4 shows solubility of bacteriorhodopsin observed directly in reaction vessel. The solubility of expressed bR is increased by Δ49A1 co-expression. A (+) indicates the addition of either DMPC, Δ49A1 DNA or bacterioOpsin DNA (bOp) to the cell-free reaction, (−) denotes absence of additive. All were expressed in the presence of −30-50 μM all-trans-retinal. Reaction 1, expression of bR in the presence of DMPC alone, purple color (shown in the figure as dark gray) has settle to bottom of vessel. Reaction 2, expression of bR in the presence of Δ49A1 co-expression, purple color remains dispersed through out vessel indicating the formation of soluble bR-NLPs.

Single-step co-expression, assembly and purification of the soluble bR-NLP complex was completed within 4 hours giving analogous yields and functions comparable to previous published findings (2). This extremely rapid approach was also applicable to a wide variety of other transmembrane proteins (FIG. 4).

Figure 5:
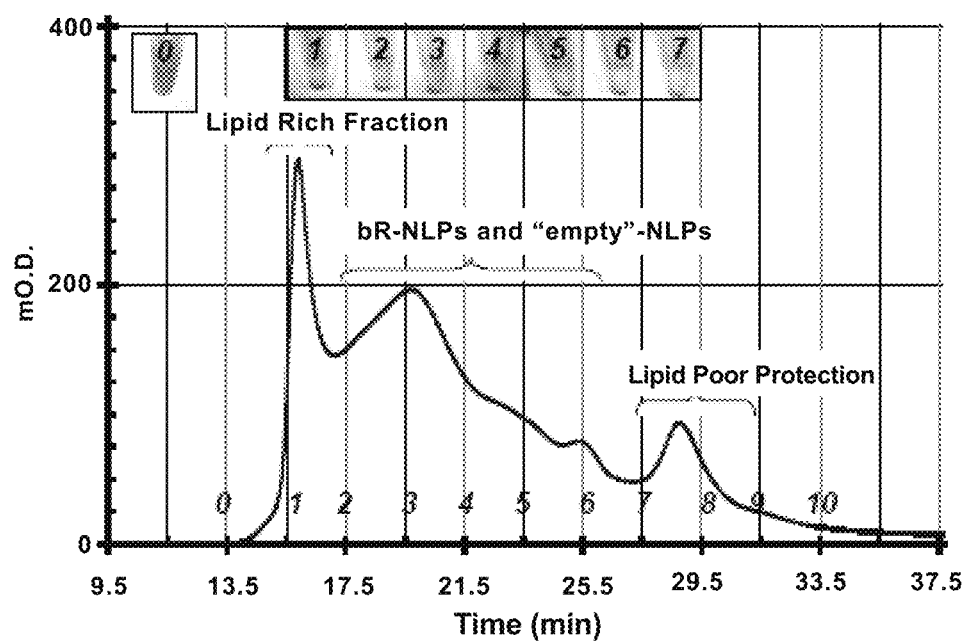
FIG. 5 shows co-expressed Ni-NTA purified bR-NLPs have several distinct sizes. Size exclusion chromatography of affinity purified co-expressed bR and Δ49A1. Tube 0, color of sample before SEC. Numbered fractions collected are indicated at the bottom of the trace. The color of corresponding concentrated fractions (top) is shown in the numbered tubes. Purple color (shown in the figure as various shades of gray) indicates the presence of properly folded bR. Fraction(s) determined to contain lipid rich constructs (vesicles or sheets), bR-NLPs, empty-NLPs and lipid poor protein are indicated on the trace. Samples were collected using a VP HPLC (Shimadzu) with a SUPERDEX™ 200 10/300 GL column (GE Healthcare) at a flow rate of 0.5 mL/min of 10 mM Tris pH 7.4; 0.15M NaCl; 0.25 mM EDTA, 0.005% $NaN_3$. Fractions were concentrated using a molecular sieve cut off filter (MWCO 50 k) VIVASPIN® 2 (Sartorius) or MWCO 10 k for the free protein fractions.

Although bR coloration was observed in the presence of DMPC without Δ49A1, very little of the material was soluble compared to when the Δ49A1 was co-expressed in the reaction mixture (FIG. 2 and FIG. 5), as indicated in the soluble (S) and pelleted (P) lanes with and without Δ49A1 co-expression). Two methods for refolding of cell-free expressed bR into lipid vesicles have been previously reported by Sonar et al., and Kalmbach et al (2, 3). However, these two approaches required multiple steps over a lengthy period of time and were further encumbered by limited membrane protein accessibility due to the nature of liposomes (2, 3). Similar results, cell-free synthesis of bR in the presence of liposomes and cofactor alone, produced functional membrane protein (purple color) that was insoluble (FIG. 2, and FIG. 5). In contrast the co-expressed bR-NLP complexes were functional, stable and soluble using our procedure.

Figure 9:
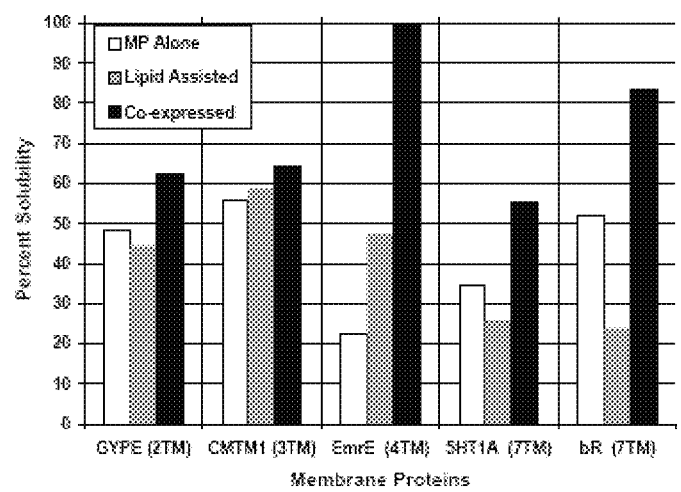
FIG. 9 shows diagram illustrating co-expression of membrane proteins with apolipoprotein Δ49A1 in the presence of lipid increases solubility of multiple membrane proteins according to an embodiment herein described. The membrane protein expressed alone is indicated in white blocks; the membrane protein expressed in presence of DMPC vesicles is indicated in gray blocks, and the membrane protein co-expressed with apolipoprotein (Δ49ApoA1) in the presence of DMPC vesicles are indicated with black blocks. Membrane proteins with the number of transmembrane domain in parentheses are (GYPE) glycophorin B (MNS blood group) (2TM), (CMTM1) CKLF-like MARVEL transmembrane domain (3TM), (EmrE) E. coli SMR efflux transporter (4TM) (5HT1A) 5-hydroxytryptamine (serotonin) receptor, (7 TM), (bR) bacteriorhodopsin (7TM).

Demonstration using bacteriorhodopsin (bR) and truncated apolipoprotein A1 (Δ49A1) produced bR-NLP complexes that were shown to be soluble, discoidal in shape and light active (FIG. 2). Distinct purple coloration, an indication of properly folded functional bR protein, was observed when all-trans retinal and phospholipid were included in the reaction mixtures (see FIGS. 2, 3, 4, and 21). Solubility survey results indicate this rapid approach may also be applicable to a wide variety of other transmembrane proteins (FIG. 9).

Example 3: Characterization of NLPs Produced by Cell-Free System: SDS Page, Native Page SEC and AFM bR-NLP complex heterogeneity was also observed by both native gel electrophoresis and SEC.

Figure 6:
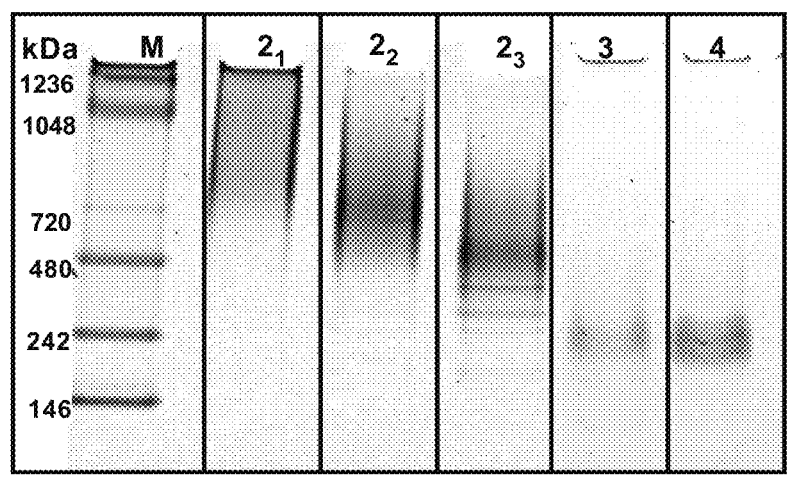
FIG. 6 shows the results of an experiments related to single-step production, purification and characterization of MP-NLP complexes according to an embodiment herein described. Native gel of size exclusion purified nanolipoprotein particles (NLPs) prepared with Δ49A1 with and without bR. Lane M, Molecular weight marker; Lane 2a-c, Fractions from SEC purified cell-free co-expressed bR-NLPs; Lane 2a, lipid rich first fraction; Lane 2b bR-NLPs second fraction; Lane 2c, bR-NLPs third fraction; Lane 3, Cell-free produced "empty"-NLPs. c. Light-Dark adaptation of bR-NLP complex. Blue, Dark adapted bR-NLPs with a $\lambda_{max}$=549 nm; Magenta, light adapted bR-NLP with a $\lambda_{max}$=554 nm. Arrows indicate the maximum peak heights which differ by a 5 nm shift between light and dark adapted.

In particular, NLPs produced as described in Example 2 were first analyzed by SEC, to detect the separation of NLPs from larger lipid-rich material. Size exclusion chromatography identified a size shift in the bR-NLP complex compared to empty NLPs or liposomes. The bR-NLP complexes eluted primarily before empty NLPs and after liposomes (FIG. 5). A size range of approximately 470-680 kDa was observed for bR-NLP complexes, which was 160-370 kDa larger than the empty self-assembled NLPs (FIG. 6).

The NLPs were also analyzed by SDS Page. In particular, a 1 μL aliquot of the total (T) cell-free reaction, soluble (S) fraction and resuspended pellet (P) were diluted with 1×LDS Sample buffer with reducing agents (Invitrogen), heat denatured and loaded on to a 4-12% gradient pre-made Bis-Tris gel (Invitrogen) along with the molecular weight standard SeeBlue plus2 (Invitrogen). The running buffer was 1×MES-SDS (Invitrogen). Samples were electrophoresed for 38 minutes at 200V. Gels were stained with coomassie brilliant blue.

The particles were also analyzed by native PAGE. Equal amounts of NLP samples (0.5-1.0 μg) were diluted with 2× native gel sample buffer (Invitrogen) and loaded onto 4-20% gradient pre-made Tris-glycine gels (Invitrogen). Samples were electrophoresed for 2 hrs. at a constant 125 V. After electrophoresis, gels were incubated with SYPRO® Ruby protein gel stain (Bio-Rad) for 2 hours and then de-stained using 10% MeOH, 7% Acetic acid. Following a brief wash with ddH$_2$O, gels were imaged using the green laser (532 nm) of a Typhoon 9410 (GE Healthcare) with a 610 nm bandpass 30 filter. Molecular weights were determined by comparing migration vs. log molecular weight of standard proteins found in the NativeMark standard (Invitrogen).

This heterogeneity may have been due to multiple factors such as number of lipids per NLP, bR oligomerization within the NLPs and/or generation of NLPs with varying diameters. Particle diameters measured by atomic force microscopy AFM (data not shown) supports the latter.

To this extent NLPs were imaged using and Asylum MFP-3D-CF atomic force microscope. Images were captured in tapping mode with minimal contact force and scan rates of 1 Hz. Asylum software was used for cross-sectional analysis to measure NLP height and diameter. For experimental analysis, the heights and diameters were measured on 182 NLPs produced by cell-free expression in the absence of bR and 430 total NLPs (empty-NLPs 185 and 255 bR-NLPs) produced by cell-free co-expression. Two-tailed student T-tests were run to compare both the height and diameter of the "empty"-NLP population in the sample co-expressed with bR compared to the sample with no bR expressed. A p-value of <0.01 was considered significant. A student T-test compares two populations of data and can determine if the difference between the two sets is statically significant or insignificant.

Figure 8:
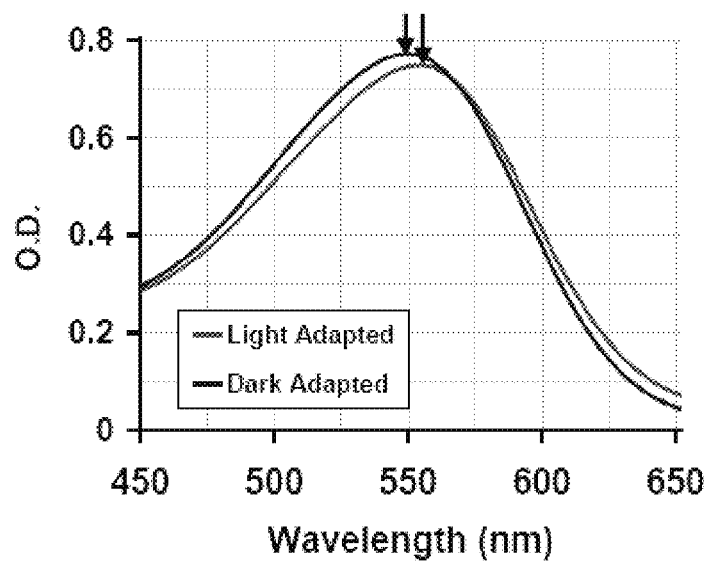
FIG. 8 shows Light/Dark adaptation of bR-NLPs. Top Dark adapted bR-NLPs with a $\lambda_{max}$=549 nm; Bottom, light adapted bR-NLP with a $\lambda_{max}$=554 nm. Arrows indicate the maximum peak heights which differ by a 5 nm shift between light and dark adapted.

Size and shape of the NLPs determined by AFM showed a height of the "empty"-NLP to be 5.0+/−0.3 while the height of bR-NLPs was 6.4+/−0.3. UV-visible spectroscopy identified a 5 nm shift upon light adaption indicating functionality Example 4: Characterization of NLPs Including Membrane Protein Indicator: Demonstration of Membrane Protein Activity Functional activity of the soluble, self-assembled, co-expressed bR-NLP complex was determined by light-dark adaptation (FIG. 8).

The light-dark adaptation yielded a 5 nm shift with a dark absorption maximum of 549 nm and light absorption maxima of 554 nm. These results indicated that the majority of active bR was in a monomeric form (4). This is in agreement with other studies that used pre-purified apolipoprotein to solubilize native forms of bR (5). The major advantage of our approach is that it allows to obtain folded light active bR-NLP assemblies in less than four hours that have been self-assembled in a single step, thereby eliminating the need for isolation of membrane protein, protein purification, dialysis and refolding protocols prior to the formation of NLP-membrane protein complexes.

Example 5: Characterization of NLPs: Co-Expression Survey of Membrane Proteins

In order to determine if the co-expression method increased solubility a series of membrane proteins with varying numbers of transmembrane domains were expressed using cell-free methods. Cell-free expression of the membrane protein alone and lipid-assisted expression of the membrane protein were used for comparison. The reactions included $^{35}$S-methionine in order to quantify the protein. Autoradiograms (not shown) were generated from total and soluble fractions separated by SDS-PAGE. Densitometry using ImageJ software (National Institutes of Health) was used to analyze the autoradiograms. The percent solubilized membrane protein compared to the total membrane protein was plotted in FIG. 9.

In particular in FIG. 9 a comparison was made between (MP alone—Grey) the membrane protein expressed alone, (Lipid Assited—striped) expression of the membrane protein in the presence of DMPC vesicles, and (Co-expressed—Black) membrane protein co-expressed with apolipoprotein (Δ49ApoA1) in the presence of DMPC vesicles. The data was generated from autoradiograms by the incorporation of $^{35}$S-Methionine in to the cell-free reaction (data not shown) that were quantified using ImageJ software (U. S. National Institutes of Health). of autoradiograms generated from SDS-PAGE.

In all cases co-expression with the truncated apolipoprotein Δ49A1 was greater that the expression of the membrane protein alone or lipid-assisted membrane protein expression (FIG. 9). Also in all cases the solubility of the membrane protein increased with co-expression of Δ49ApoA1 with added (FIG. 9).

Example 6: Compared Self-Assembly of Cell-Free Produced and Conventionally Produced NLPs NLPs produced by cell-free methods and NLPs assembled by conventional means (6) were both examined by AFM to assess NLP size and shape and to demonstrate the association between bR with NLPs. For comparison to cell-free produced bR-NLP complexes, both bR-NLPs and "empty"-NLPs were also prepared using previously described methods (6, 7).

Conventional assembly of NLPs is described herein in Examples 13 to 33. Briefly, the truncated form of Apo A1 (Δ1-55) called MSP1T2 or Δ55A1 was purchased from Nanodisc Inc. For "empty"-NLPs Δ55A1 was combined with DMPC liposomes in a ratio of 1:4 by mass in TBS buffer. The mixture was then incubated at room temp for 2 hours. The NLPs were then purified by size exclusion chromatography. Assembly of bR-NLPs: Δ55A1 was mixed with DMPC in a ratio of 1:4 by mass in TBS buffer. Sodium cholate solution was then added to a final concentration of 20 mM. Purple membrane bacteriorhodopsin was then added in a 0.67 mass ratio to the Δ55A1 apolipoprotein. Incubation proceeded as described above, followed by dialysis in TBS for detergent removal. The NLPs were then purified by size exclusion chromatography.

In particular, the size exclusion chromatography was performed as follows. The NLPs made with and without incorporated membrane protein were purified from 'free protein' and 'free lipid' by HPLC (Shimadzu) using a SUPERDEX™ 200 10/300 GL column (GE Healthcare), with TBS at a flow rate of 0.5 ml/min. The column was calibrated with four protein standards HMW Gel filtration calibration kit (GE Healthcare), of known molecular weight and Stokes diameter that span the separation range of the column and the NLP samples. The void volume was established with blue dextran. The NLP fraction is concentrated about 10-fold to approximately 1.0 mg/ml using molecular weight sieve filters (Vivascience) having molecular weight cutoffs of 50 kDa. Protein concentration was determined using the ADV01 protein concentration kit (Cytoskeleton), which is based on Coomassie dye binding.

Figure 10:
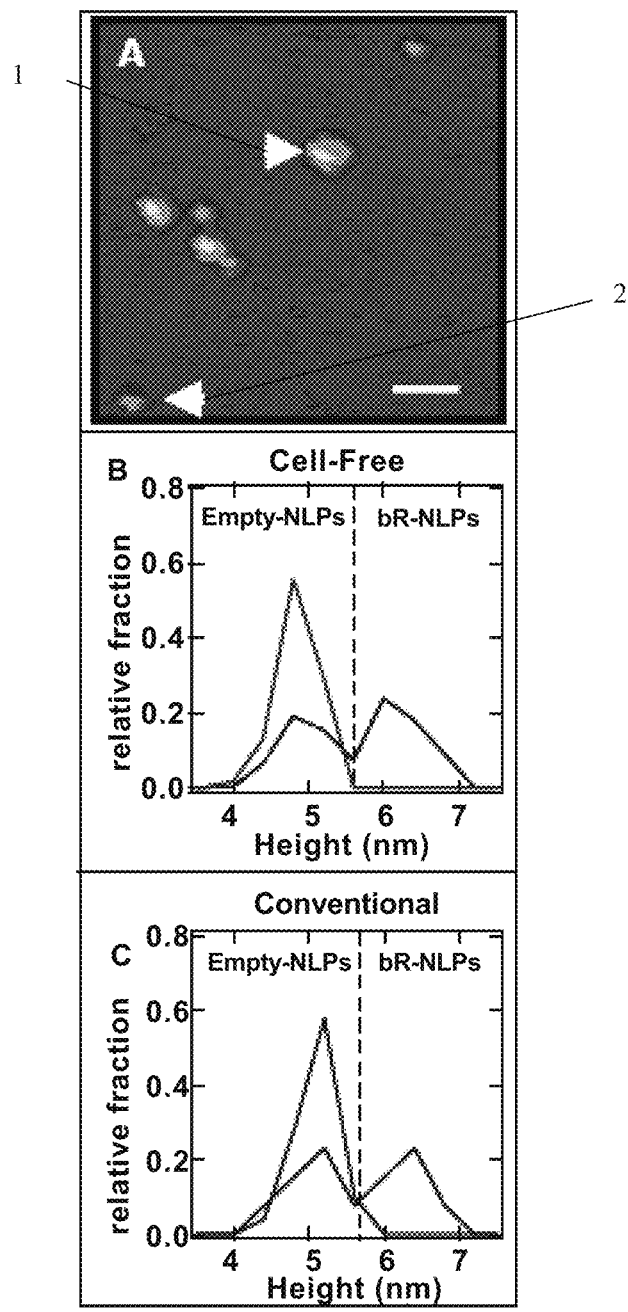
FIG. 10 shows the result of AFM analysis confirming the association between NLPs and bR according to an embodiment herein disclosed. Panel A shows the AFM image of NLPs produced through cell-free co-expression of Δ49A1 and bR in the presence of DMPC. The brighter green regions are NLPs with a higher height indicating the insertion and plausible location of bR in the lipid bilayer. Scale bars are 50 nm; Arrow 1, indicates expression of "empty"-NLP's, while arrow 2, indicates the bR-NLP complex. Panel B shows a height histogram of NLPs produced through conventional assembly of (top trace) Δ49A1 with DMPC alone or (bottom trace) in the presence of purple membrane bR and DMPC. The shaded areas indicate populations with an increased height. Panel C shows a eight histogram of NLPs produced through cell-free expression of (top trace) Δ49A1 with DMPC alone or (bottom trace) co-expression of bR and Δ49A1 in the presence of DMPC. The shaded areas indicate populations with an increased height. NLPs heights were analyzed through cross-sectional analysis.
Figure 11:
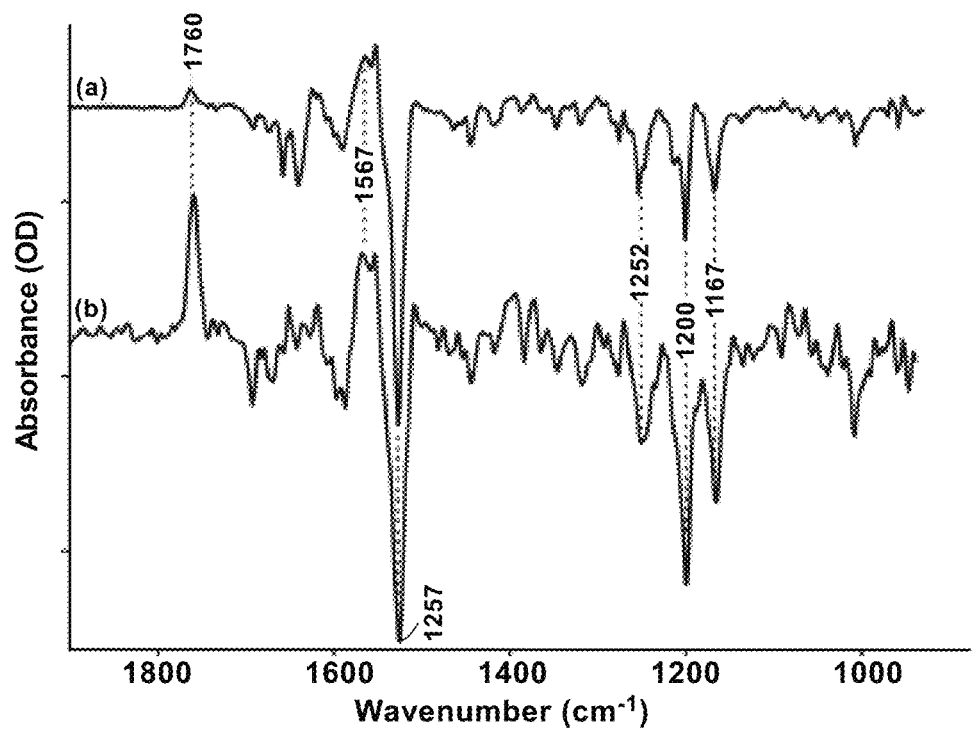
FIG. 11 shows the FTIR difference spectra for the bR→M transition FTIR difference spectra of (A) bR WT and (B) bR-NLP. The largest peaks are 9.4 and 0.34 mOD, respectively. The positive bands represent vibrations in the M state and negative bands represent the ground state. Despite the smaller signal, the spectrum of BR NLP clearly indicates functional protein that is stable over ~$10^4$ laser flashes.

These NLPs and bR-NLP complexes were made with a similarly truncated form of Apolipoprotein A1 (Δ1-55) or Δ55A1 (MSP1T2, Nanodisc Inc.), purple membrane bR and DMPC liposomes (6, 7). Both the co-expressed and conventionally assembled bR-NLPs showed similar increases in particle height relative to an "empty" NLP indicating likely association of bR protein within the NLPs (FIG. 10).

Empty NLPs produced either by conventional methods or cell-free displayed heights of approximately 5.0±0.3 nm (s.d.) as determined by AFM (FIGS. 10B and 10C respectively). The NLPs produced by either conventional assembly of Δ49A1 and bR (FIG. 10B) or co-expression of Δ49A1 and bR (FIG. 10C) appeared as two distinct discoidal populations when examined by AFM cross-sectional height analysis. The first population is approximately 5.1±0.3 nm (s.d.) in height, analogous to "empty"-NLPs (FIG. 10C). The second population, which was not observed in control experiments lacking bR, was approximately 6.4±0.3 nm (s.d.) in height (FIG. 10C). The increased height observed in the presence of bR is located in the center region of the NLP (bright green dot, pseudo color) is consistent with the bR being contained within the NLP lipid bilayer (FIG. 10A). Additionally, the increased height particles produced in the presence of bR also had an associated increase mean diameter (27.8±5.8 nm (s.d.)) relative to the "empty" Δ49A1-NLPs (22.0±5.1 nm) (Table 2).

Using solely the increase in height as a basis for distinguishing bR-NLPs from "empty" Δ49A1-NLPs, an overall yield of protein incorporation of 58% was determined (Table 2). Two-tailed student T-tests indicated that there was no statistically significant difference between the diameter and height of the "empty" Δ49A1-NLPs produced by cell-free methods in the presence (n=185; 2a) and absence (n=182; 1) of bR (Table 2) with p-values of 0.94 and 0.04 respectively. However, a statistically significant increase in diameter and height was observed between the bR-NLPs (n=255; 2b) and "empty" Δ49A1-NLPs (n=185, 2a) with p-values of $1.8 \, E^{-24}$ and $3.9 \, E^{-155}$ respectively (Table 2). Those results are illustrated in Table 2 that includes a summary of analysis of cell-free expressed NLPs with and without co-expressed bR

TABLE 2

| | Sample | Height (nm) +/− s.d. | Relative % Increase Diameter | % NLP |
|---|---|---|---|---|
| 1 | "empty" Δ49A1 NLPs | 5.0 +/− 0.3 | 1 | 100 |
| 2a | Co-expressed "empty"-Δ49A1 NLPs | 5.1 +/− 0.3 | 1 | 42 |
| 2b | Co-expressed Δ49A1/bR-NLPs | 6.4 +/− 0.3* | 1.3* | 58 |

*Statistically significant, see text for specific values.

Figure 7:
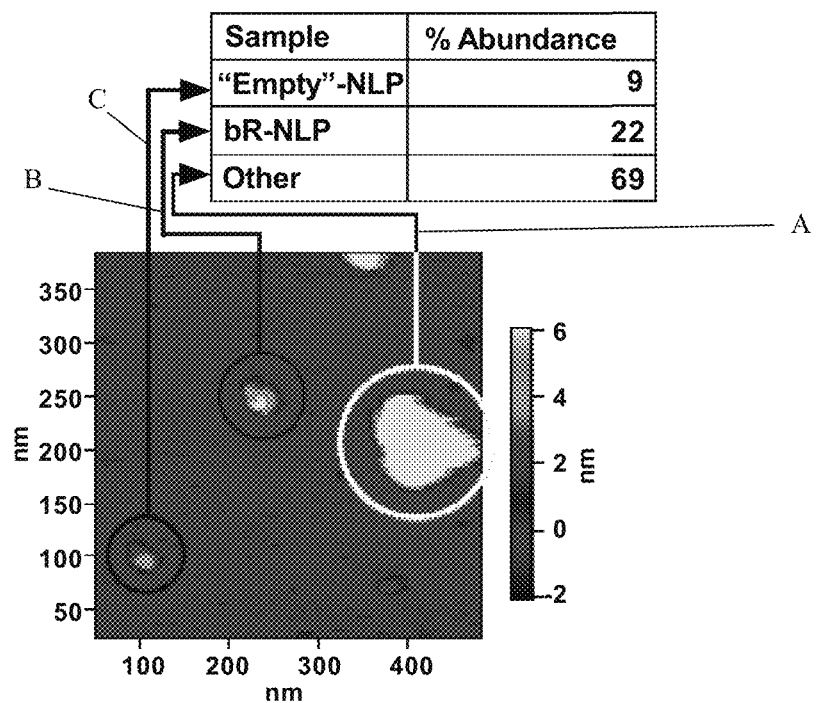
FIG. 7 shows AFM image of lipid rich SEC fraction. An AFM image representing the first fraction collected by size exclusion chromatography of the cell-free co-expression of Δ49A1 and bR in the presence of DMPC. AFM image of the lipid rich fraction displaying all three populations depicted in the top table. Observed diameter and height measurements for the lipid rich fraction displays three populations; Line A indicates large lipid complexes, liposomes or membrane sheets; Line B indicates bR-NLPs and Line C indicates "empty"-NLPs. This analysis clearly indicates the majority of structures in this fraction were lipid vesicles or membrane sheets with much larger diameters and heights.

AFM was also used to visualize the first SEC fraction, where high molecular weight lipid complexes were observed consistent with results reported in Chromy et al (6) in which was described lipid-based macro-molecular formations unable to enter a native-PAGE and had the appearance of liposom-like material (FIG. 7). The majority of this material was distinctly different in size, ranging 35-60 nm in diameter and 6.5-20 nm in height indicating the majority of the material was large lipid complexes such as liposomes or membrane patches.

Example 7: Cell-Free Expression and Purification of Apolipoproteins

The methods described below outline cell-free expression and purification of apolipoproteins. In particular, it is described the cell-free production of a selected N-terminal truncation of human apolipoprotein E4 which does not require post-translational modification.

The following materials and instruments were used: Apolipoprotein (ApoA1, MSP, Apo E4, lipophorin III, or truncations Δ49ApoA1 and ApoE4 22 k) clones of interest from the LLNL-IMAGE Consortium cDNA collection or as a gift from collaborating labs, subcloned in to an expression vector such as, pET32a thioredoxin (Novagen) (33, 34), pIVEX-2.4b (Roche), or pEXP4 (Invitrogen); Spectrophotometer UV-visible $A_{260}/A_{280}$ quantification or PicoGreen dsDNA Quantification Kit (Invitrogen/Molecular Probes); Cell-Free Expression System: Expressway™ Maxi Cell-Free E. coli Expression System (Invitrogen) or RTS 500 ProteoMaster E. coli HY Kit (Roche); Thermomixer, EPPENDORF® THERMOMIXER® R (for Roche lysates) or Incubator shaker for example New Brunswick C24 (for Invitrogen lysates); Disposable fritted columns 3 mL capacity (Bio-Rad); Ni-NTA Superflow resin (Qiagen); Ni-NTA buffers (modified Qiagen recipes) Binding buffer: 50 mM $NaH_2PO_4$, 300 mM NaCl; pH 8.0; Wash Buffer: 50 mM $NaH_2PO_4$; 300 mM NaCl; 10 mM Imidazole; pH 8.0; Elution Buffer: 50 mM $NaH_2PO_4$; 300 mM NaCl; 400 mM Imidazole; pH 8.0; Gel electrophoresis equipment; NuPAGE 4-12% Bis-Tris SDS-PAGE gel with 1×MES-SDS running buffer (Invitrogen), Protein Quantification Kit and standards, such as Bio-Rad Protein Assay (Bio-Rad) VIVAS-PIN® 6, ultrafiltration Devices, 10 k MWCO (Sartorius Biotech); Centrifuge such as EPPENDORF®-5804R (Needs to fit 15 mL Falcon tubes); Thrombin (Novagen); DMPC; 1,2-Dimyristoyl-sn-Glycero-3-Phosphocholine (Avanti Polar Lipids); Probe or bath sonicator; β-mercaptoethanol; TBS Buffer: 10 mM Tris-HCl; 0.15 M NaCl; 0.25 mM EDTA; 0.005% NaN$_3$ (sodium azide) adjust to pH 7.4; and FPLC Instrument (Shimadzu SCL-10A), size exclusion column (SUPERDEX™ 200 10/300 GL (GE Healthcare Life Sciences).

In particular, Lipophorin III DNA clones (*M. sexta* and *B. mori*) were obtained from the lab of Robert Ryan at Children's Hospital Oakland Research Institute (CHORI). Truncated Apolipoprotein E4 22 kDa N-terminal thioredoxin fusion plasmid was obtained from Karl Weisgraber at the University of California, San Francisco. The 193 amino acid protein sequence of the 22 kD Apolipoprotein E4 construct is as follows, with the two initial amino acids, Gly-Ser, are left over from the thrombin cleavage site in pET32a. Midi or Maxi prepped plasmid DNA was prepared according to the Qiagen protocol.

(SEQ ID NO: 5)
GSKVEQAVETEPEPELRQQTEWQSGQRWELALGRFWDYLRWVQTLSEQVQ

EELLSSQVTQELRALMDETMKELKAYKSELEEQLTPVAEETRARLSKELQ

AAQARLGADMEDVRGRLVQYRGEVQAMLGQSTEELRVRLASHLRKLRKRL

LRDADDLQKRLAVYQAGAREGAERGLSAIRERLGPLVEQGRVR

Figure 13:
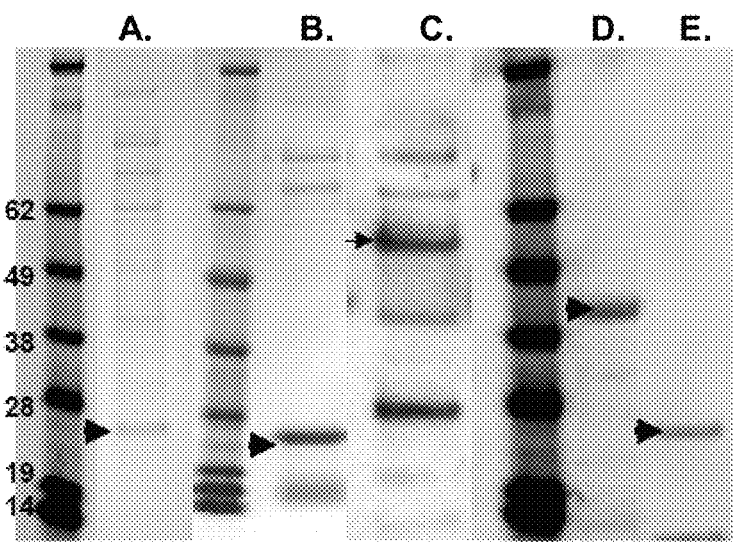
FIG. 13 shows lipoproteins expressed in cell-free extracts according to an embodiment herein described. Lipoprotein were purified using Ni-NTA affinity chromatography and run on a SDS-PAGE gel, stained with Coomassie Brilliant Blue (A-B and D-E) or detected by fluorescent scanning of labeled lysine residues (C). Arrows indicate apolipoprotein of interest. Proteins A-D and F-G are shown with SeeBlue MW marker (Invitrogen) (A) Full-length apolipoprotein A1 (B) MSP1 truncated form of ApoA1 (C) Full-length Apolipoprotein E4 (D) 22 kD truncated ApoE4-fusion protein (H) Thrombin cleaved truncated ApoE422k. Other Lipoproteins produced (not shown) include Apolipophorin III B. mori, Apolipophorin III, M. sexta.
Figure 14:
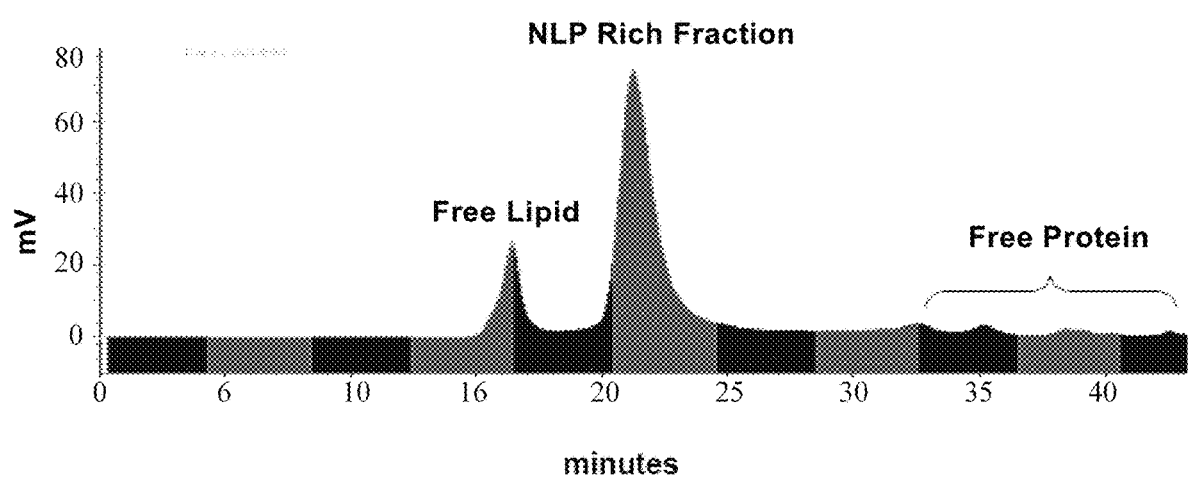
FIG. 14 shows a diagram illustrating the results of size exclusion chromatography separation of ApoE422k Nanolipoprotein particles (NLPs) according to an embodiment herein disclosed. Free lipid, and free protein denoted on graph are separated from the NLP rich fraction.

The cDNAs for apolipoprotein were selected and cloned into expression vector of interest such as pIVEX-2.4b (Roche Applied Science), GFP folder or pETBlue-2 (Novagen), pET32a (thioredoxin fusion vector). The plasmids were propagated by transforming into Top10 or DH5α ☐chemically competent cells (Invitrogen) and isolate DNA using HiSpeed Plasmid Maxi or Midi Kits (Qiagen). The N-terminal truncated apolipoprotein E4-22 kD (ApoE422k) thioredoxin (trx) fusion protein construct in pET32a (ApoE422k-trx) is illustrated here (FIG. 13). The Midi or Maxi prepped plasmid DNA concentrations were determined by PicoGreen dsDNA Quantification Kit (Molecular Probes) or by UV-visible spectroscopy $A_{260}/A_{280}$. The cell-Free protein production reactions were performed using either the Expressway™ Maxi Cell-Free *E. coli* Expression System (Invitrogen) or RTS 500 ProteoMaster *E. coli* HY Kit (Roche) using ~15 µg of midi or maxi prepped DNA in a 1 mL reaction size.

The reactions were incubated at 30° C. shaking at 990 rpm in a thermomixer (Roche RTS ProteoMaster or EPPENDORF® THERMOMIXER® R)—(Roche Lysates) or 37° C. shaking at 225 rpm in a shaker incubator (New Brunswick)—(Invitrogen Lysates). All reactions were run overnight (although 4 hours is sufficient). A 5-10 µl sample was collected for further analysis.

The His-tagged apolipoprotein (ApoE422k) was purified by using Ni-NTA native affinity chromatography, and 1 mL of the Ni-NTA slurry, equivalent to 500 µL column bed volume (Qiagen) was equilibrated with binding buffer and resuspend the resin to form a 50% slurry again. The equilibrated slurry was added to the cell-free post-reaction mixture and mix at 4° C. for 1-2 hours. The mixture was added to a 3-mL fritted plastic column and collected the flow through for SDS-PAGE analysis.

The column was washed with eight column volumes (500 µL) of native wash buffer. Fractions are collected for SDS-PAGE analysis.

The bound apolipoprotein was eluted with six column volumes of native elution buffer.

All collected fractions were analyzed by denatured gel electrophoresis using a NuPAGE 4-12% Bis-Tris SDS-PAGE gel with 1×MES-SDS running buffer for 38 minutes at 200V (Invitrogen). The load buffer is LDS Sample Buffer (Invitrogen). Volumes to load for SDS-Page gels were as follows: 14 of total reaction and non-bound flow through, 5 µL wash fractions 1-2, 20 µL of remaining washes and all elutions. Gels were stained with Coomassie brilliant blue.

Elution fraction of interest determined by gel electrophoresis were combined and concentrated and buffer exchanged into TBS using an ultrafiltration device VIVASPIN® 6. In particular, concentration from 6 mL to 100 µL was easily achieved in ~15 min at 5000 RCF in an EPPENDORF® 5804R centrifuge with a fixed angle rotor check each 3-5 min. Buffer exchange into TBS pH 7.4 required at least 3 dilutions and re-concentration steps. Alternatively eluted protein could were dialyzed (spectrapor 1 MWCO 3500) against TBS buffer overnight and concentrated by immersion of the dialysis membrane in PEG 8000 (polyethylene glycol).

The final protein concentration was determined by Bradford total protein concentration following the manufacturer's protocol.

Small unilamellar vesicles of DMPC were then prepared by probe sonicating 20 mg DMPC lipid into 1 mL TBS at 6 amps for approximately 15 minutes or until optical clarity is achieved. Typically fifteen minutes is sufficient to achieve optical clarity. An appropriate container choice was a thick walled 3 mL glass conical vial. In particular, lipid solution were vortexed lightly before sonication to help get to lipid into the buffer. Lipid should be stored at −20° C. when not in use, and protected from water absorption. When sonicating lipid overheating of the lipids was avoided by either sonicating in a beaker of ice or cooling the sample every few minutes. The solution was practically water clear at the end of the sonication. If the probe hits the side of the glass vessel metal will be sloughed off into the solution and the solution will become grayish. The metal can be removed by a short centrifugation at 13,700 RCF for two minutes after transferring to a 1.5 ml EPPENDORF® tube. Remove the supernatant and use. Any white pellet indicated DMPC that is not in vesicle form. Alternatively, sonicate in bath sonicator to optical clarity and skip the centrifugation step.

The sample was transferred to a 1.5 mL tube. Any contaminant metal was removed from the probe by centrifugation at 13700 RCF for 2 minutes in a 1.5 mL tube.

Thioredoxin fusion protein tags were removed by incubating 2-4 mg of the produced protein with 100 µg/mL of the sonicated DMPC overnight at 24° C. Thrombin was added at 1:500 w/w ratio (thrombin:apolipoprotein) and incubated at 37° C. for one hour. The reaction was halted by the addition of β-mercaptoethanol to a final concentration of 1%. 5 µg of the product were analyzed by SDS-PAGE as described above. The results are shown in FIG. 13.

Contaminant thioredoxin (trx), thrombin and β-mercaptoethanol were then removed from the apolipoprotein, ApoE422k by size exclusion chromatography using a FPLC Instrument (Akta, GE Healthcare and Life Sciences or Shimadzu SCL-10A), and size exclusion column (SUPERDEX™ 200 10/300 GL) with a TBS buffer at a flow rate of 0.5 mL/min. The fractions of interest were determined by gel electrophoresis combine and concentrate as above.

Example 8: Nanolipoprotein Particle (NLP) Formation and Purification

The methods described below outlines nanolipoprotein Particle (NLP) formation and purification. The following materials and equipments were used: DMPC: 1,2-Dimyristoyl-sn-Glycero-3-Phosphocholine (Avanti Polar Lipids); Purified apolipoprotein protein or truncation (ApoE422k construct); TBS Buffer: 10 mM Tris-HCl; 0.15 M NaCl; 0.25 mM EDTA; 0.005% NaN3 (sodium azide); adjust to pH 7.4. 30° C. and 20° C. water baths; Probe or bath sonicator; Spin filter, 0.45 µm; Concentrator 50 kD MWCO, VIVASPIN® 2 (Sartorius Inc.) (Other concentrator brands that are angled are also acceptable such as Agilent, because the nanolipoprotein particle produced will be larger than 200 kD, a 100 kD filter may be useful); FPLC Instrument (Shimadzu SCL-10A), size exclusion column (SUPERDEX™ 200 10/300 GL (GE Healthcare Life Sciences).

Nanolipoprotein particles (NLPs) form in a self assembly process in the correct mass ratio of apolipoprotein to lipid. This ratio needs to be optimized for each different apolipoprotein. The ratio described below is for ApoE422k (21). Other ratios can be found in the literature (7, 10, 11).

The water bath incubators were started with temperatures at 30° C. and 20° C. 34 mg of DMPC were probe sonicated into 1 mL of TBS at 6 amps for approximately 15 minutes or until optical clarity is achieved. DMPC solution was centrifuged at 13700 RCF for 2.5 min to remove residual metal from probe sonicator. The supernatant was transferred into a new tube. Apo E422K was combined with DMPC in a ratio of 1:4 by mass in TBS buffer in a 1.5 mL EPPENDORF® tube. Typically batches are of the 250 µL size.

Transition temperature procedure was performed as follows: the tube was immersed in water bath for 10 minutes each 30° C. (above DMPC transition temp.) followed by 20° C. (below DMPC transition temp.). The procedure was repeated three times then the tube was incubated at 23.8° C. overnight.

Filter preparation was performed through a 0.45 µm spin filter at 13700 RCF for 1 min. Purify NLPs using size exclusion chromatography. A Shimadzu SCL-10A FPLC was used that was equipped with a SUPERDEX™ 200 10/300 GL column with TBS buffer, a 200 µL sample injection volume, and a flow rate of 0.5 mL/min. Collect 0.5 mL fractions see FIG. 14.

Fractions were concentrated using a VIVASPIN® 2 ultrafiltration device with a 50 k MWCO as described in Example 7.

Example 9: Biotinylation of Membrane Protein

The methods described below outline the biotinylation of membrane bound proteins, and in particular of Bacteriorhodopsin (bR). The following materials and equipments were used: EZ-LINK® Sulfo-NHS-LC-Biotin (Pierce); Bacteriorhodopsin (Sigma); Bath sonicator; Ultracentrifuge (Beckman-Coulter Optima TLX, TLA-120.2 fixed angle rotor); 1×BupH PBS buffer (Pierce): 0.1 M $NaH_2PO_4$, 0.15 M NaCl; pH 7.0. Bacteriorhodopsin can also be produced in a cell-free manner and purified in the denatured state. A re-folding procedure is then employed to incorporate the retinal according to the methods of Rothschild et al (2, 12).

Biotinylation of the membrane protein (MP) provides a tool for investigating the incorporation of the MP with the NLP. Biotinylation using of bacteriorhodopsin supplied in membrane sheets from Sigma selectively labels only the solvent exposed lysine residues when using EZ-LINK® Sulfo-NHS-LC-Biotin (Pierce) which is impermeable to membranes. Bacteriorhodopsin in membrane sheets is easily separated from the aqueous phase by centrifugation. For other membrane proteins that may be solubilized in detergent micelles removal of excess biotin solution will need to be accomplished using a desalting column or other means. Membrane proteins including bR may be expressed in a cell free manner and biotinylated (2, 13-16).

In particular, bacteriorhodopsin (bR) purchased from Sigma and stored as a lyophilized powder at 4° C. was resuspended in BupH PBS buffer in the original bottle. Amine containing buffers such as TBS, were avoided due to the interaction with the biotinylation reagent. The sample was bath sonicated eight times for 1 min. each chilling the bottle on ice for one minute in between each burst. UV-visible spectra were recorded to confirm the concentration of bR in solution using the molar extinction coefficient at 568 nm of 63,000 M-1cm-1.

A freshly made 10 mM solution of EZ-LINK® Sulfo-NHS-LC-Biotin (Pierce) was prepared according to the manufactures recommendation in ddH2O.

The biotin solution was added to the bacteriorhodopsin solution in a 20-fold molar excess, and incubated on ice for two hours.

The excess biotin was removed by centrifugation of the solution in an ultracentrifuge at an RCF of 89,000 (although 50,000 should be sufficient) for 20 minutes at 4° C. The supernatant was removed and the bR pellet resuspended in TBS buffer. This process was repeated two times total. In particular, Bacteriorhodopsin in membrane sheets was extremely sticky, and did pellet well at the RCF listed. 85-90% recovery of bR was achieved with careful resuspension and washing of tips and tubes. Resuspension should be in the TBS buffer used for assembly (or other buffer of interest that will be used for assembly).

UV-visible spectra were collected as described above to calculate the concentration of the solution and the percent recovery typically around 85-90% with careful resuspension.

Example 10: Membrane Protein Incorporation into Nanolipoprotein Particles (MP-NLPs)

The methods described below outline incorporation of a membrane protein into nanolipoprotein particles (NLPs). The following materials and equipments were used: DMPC [1,2-Dimyristoyl-sn-Glycero-3-Phosphocholine] (Avanti Polar Lipids); Purified apolipoprotein or truncation (ApoE4 22 kD construct); TBS Buffer: 10 mM Tris-HCl; 0.15 M NaCl; 0.25 mM EDTA; 0.005% $NaN_3$ (sodium azide), adjusted to pH 7.4; Sodium Cholate (Sigma) 500 mM solution in TBS; Biotinylated Bacteriorhodopsin (bR) (Sigma) from Example 22; 30° C. and 20° C. and 23.8° C. water baths; Probe Sonicator; Dialysis cups 10,000 MWCO (Pierce) or D-Tube Dialyzers, mini (Novagen); Spin filter, 0.45 µm; FPLC Instrument (Shimadzu SCL-10A); size exclusion column (SUPERDEX™ 200 10/300 GL (GE Healthcare Life Sciences); Concentrator 50 kD MWCO, VIVASPIN® 2 (Sartorius Inc.).

The water bath incubators were started at temperatures at 30° C. and 20° C. 34 mg of DMPC were probe sonicated into 1 mL of TBS at 6 amps for approximately 15 minutes or until optical clarity was achieved. Alternatively, the DPMC can be sonicated in bath sonicator to optical clarity (see Example 7).

The solution was centrifuged at 13K for 2 minutes to remove residual metal sloughed off from probe sonicator. 250 µL were batched in a 1.5 mL EPPENDORF® tube. Combine Apo E422K with DMPC in a ratio of 1:4 by mass in TBS buffer. Sodium cholate solution was then added to a final concentration of 20 mM. The biotinylated bacteriorhodopsin membrane protein was then added in a 0.67 mass ratio to the Apo E422k apolipoprotein.

The transition temperature procedure was performed as follows: the tube was immersed in water bath for 10 minutes each 30° C. (above DMPC transition temp.) followed by 20° C. (below DMPC transition temp.). The procedure was repeated three times and the tube was then incubated at 23.8° C. overnight.

The cholate detergent was removed and MP-NLPs (bR-NLPs) were allowed to self-assembly; the sample was loaded into a pre-soaked D-Tube Dialyzers, mini (Novagen). The sample was then dialyzed against 3 changes each of 1 L TBS buffer over a 2-3 day period at room temperature. In particular, dialysis at 4° C. was used for unstable membrane proteins. Detergent use was compatible with the membrane protein of interest. Adsorbent beads (Bio beads, Bio-Rad) were also used to remove the detergent. If dialysis cups were used (Pierce) the sample was split into three pre-soaked dialysis cups. Care was taken not to create bubbles or droplets on the sides of the cups.

The sample was then concentrated using an ultrafiltration device, VIVASPIN® 2 (Sartorius) MWCO 50K to 200 µL.

The supernatant was transferred into new tube. Size exclusion chromatography was performed using a Shimadzu SCL-10A FPLC, equipped with a SUPERDEX™ 200 10/300 GL column (GE Healthcare Life Sciences). The buffer was TBS with a 200 µL sample injection volume, a 0.5 mL/min flow rate and 0.5 mL-1.0 mL fraction size.

The fractions of interest were concentrated using an ultrafiltration device, VIVASPIN® 2 (Sartorius) MWCO 50K for NLP peaks.

Example 11: Validating NLP Formation by Native Gel Electrophoresis and Confirmation of Membrane Protein Association and Functionality with NLPs by Microarray, UV Visible Spectroscopy, AFM and EM The methods described below outlines a procedure to validate protein association by microarray and UV visible spectroscopy. The following materials and equipments were used: 4-20% Tris-Glycine polyacrylamide gel, 1×Tris-Glycine native running buffer, 2× Native Sample buffer, Native Mark molecular weight marker (Invitrogen); SYPRO® Ruby Stain (Bio-Rad) light sensitive, Aqueous destain solution: 10% Methanol; 7% acetic acid; Fluoroimager with appropriate filter for SYPRO® Ruby stain; Biotinylated positive control protein such as biotinylated-bR; Bovine serum albumin 1 mg/ml solution; PBS-Tween buffer: 1.06 mM KH2PO4; 2.97 mM Na2HPO4; NaCl 1551.72 mM, 0.05% tween-20 (v/v) pH 7.4; 1×PBS buffer, (Gibco): 1.06 mM KH2PO4; 2.97 mM Na2HPO4; NaCl 1551.72 mM, pH 7.4; Cyanine-5-Strepavidin (Rockland) solution (5 µg/mL); Barcoded γ-Aminopropylsilane coated glass slides (GAPS-II; Corning); Robotic arrayer; Hybridization Chamber (Grace Bio-Labs); Blocking buffer: 1 mg/mL BSA in 1×PBS, Wash Buffer: 1×PBS; Laser-based confocal scanner (ScanArray 5000 XL; Perkin-Elmer); UV-visible plate reader (Bio-TEK Synergy HT); 96 well flat bottom UV plate (Corning Costar UV Plate).

Validation Through Native Polyacrylamide Gel Electrophoresis

Native polyacrylamide gel electrophoresis is used to validate the association of proteins of interest (apolipoprotein and/or membrane protein) with NLP fractions eluted from the size exclusion column. Protein identification is confirmed with mass spectrometry.

Native-PAGE gels, 4-20% Tris-glycine were run with 0.75 µg total loaded protein estimated by $A_{280}$ absorbance. 10 µL of molecular weight standards, Native mark (Invitrogen) diluted 20× in native sample buffer were loaded on the gels. The gels were run at 125V for approximately 2 hours.

The gels were stained with ~150 mL of SYPRO® Ruby protein stain (Bio-Rad) following the microwave staining method: 30 sec. microwave, 30 sec. mixing on shaker table, 30 sec microwave, 5 min. shake, 30 sec. microwave, finally 23 min. on shaker table at room temperature. The gels were destained for 1.5 hours on a shaker table at room temperature.

The gels were imaged using a Typhoon Imager with appropriate filters selected for the SYPRO® Ruby fluorescence.

Figure 15:
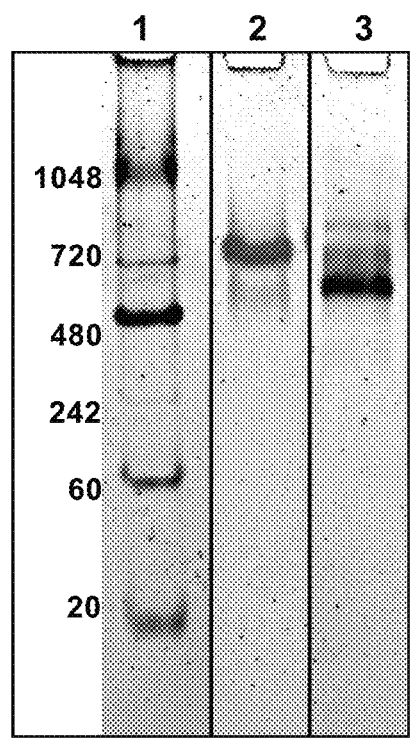
FIG. 15 shows native gel electrophoresis of NLPs according to an embodiment herein disclosed. 1) Native Mark molecular weight marker. 2) "Empty"-NLPs 3) Membrane protein (bacteriorhodopsin) bR-NLPs. 4-20% Tris-glycine gel, with Tris-glycine running buffer, stained with SYPRO® Ruby Stain (BioRad) Imaged with a Typhoon scanner.

The results are illustrated in FIG. 15.

Confirmation of Membrane Protein Association and Functionality with NLPs by Microarray Microarray spotting technology was used to attach NLPs to an amino-silane coated glass slide in an array format for streptavidin binding studies (17-19) Biotinylated bacteriorhodopsin (bR) was used to validate the incorporation of bR into nanolipoprotein particle fractions eluted from size exclusion chromatography. Cyanine-5-Strepavidin was used for fluorescence detection of biotinylated bacteriorhodopsin.

Microarray single print head was used to deposit approximately 1 nL of diluted protein solution on the slide. It was determined that robotic spotting is best when the humidity is greater than 30%. Proteins were spotted in 4×4 squares with 16 replicates of each sample, generating ~300 µm diameter spots with a spot-to-spot distance of ~350 µm.

Protein microarrays were spotted on GAPSII amino silane glass slides (Corning) with bacteriorhodopsin bR (non-biotinylated), biotinylated-bR, biotinylated-bR-NLPs, using a robotic arrayer. Non-biotinylated bR was used as a negative control, and biotinylated-bR was used as a positive control.

Bacteriorhodopsin (bR) concentrations of 10 mM, as determined by UV-visible spectroscopy as described above were used for all samples.

Proteins were cross-linked to the glass slides by exposure to UV light for five minutes. Unused slides were stored at 4° C. without UV cross-linking.

The hybridization chamber was applied with a volume capacity of 950 µL to the slide carefully as to not disrupt the array. Carefully add reagents below without injecting bubbles.

The slides were blocked with BSA (1 mg/mL) for 30 minutes. The slides were washed with 1×PBS for 15 minutes. Cyanine-5-streptavidin (5 µg/mL) was bound for 15 minutes. The slides were washed in 1×PBS then nanopure water each for 15 min. The slides were dried by centrifugation or air dry.

Protein microarrays of bR, biotinylated-bR and bR-NLPs were imaged with a laser-based confocal scanner (ScanArray 5000 XL; Perkin Elmer) using the VheNe 594 nm laser for detection of any bound Cyanine-5-streptavidin.

Images were collected and analyzed using the mean pixel intensities with Scan Array software (Perkin Elmer) (data analysis not shown).

Figure 16:
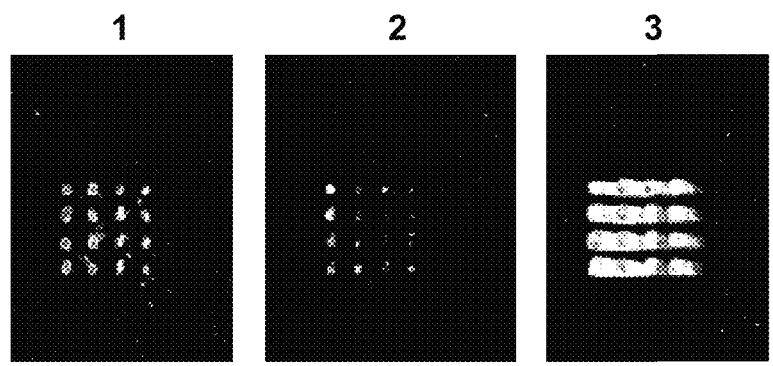
FIG. 16 shows a protein microarray of biotinylated bR-NLPs according to an embodiment herein disclosed. (1) biotinylated-bacteriorhodopsin (2) negative control, native bacteriorhodopsin (3) biotinylated-bacteriorhodopsin associated NLPs.

The results are illustrated in FIG. 16.

Confirmation of Membrane Protein Association and Functionality with NLPs by UV-Visible Spectroscopy, AFM and EM UV-visible spectroscopy of light and dark adapted bacteriorhodopsin can be used to determine the functionality of the protein and relates information regarding the conformation of the protein (4).

Figure 17:
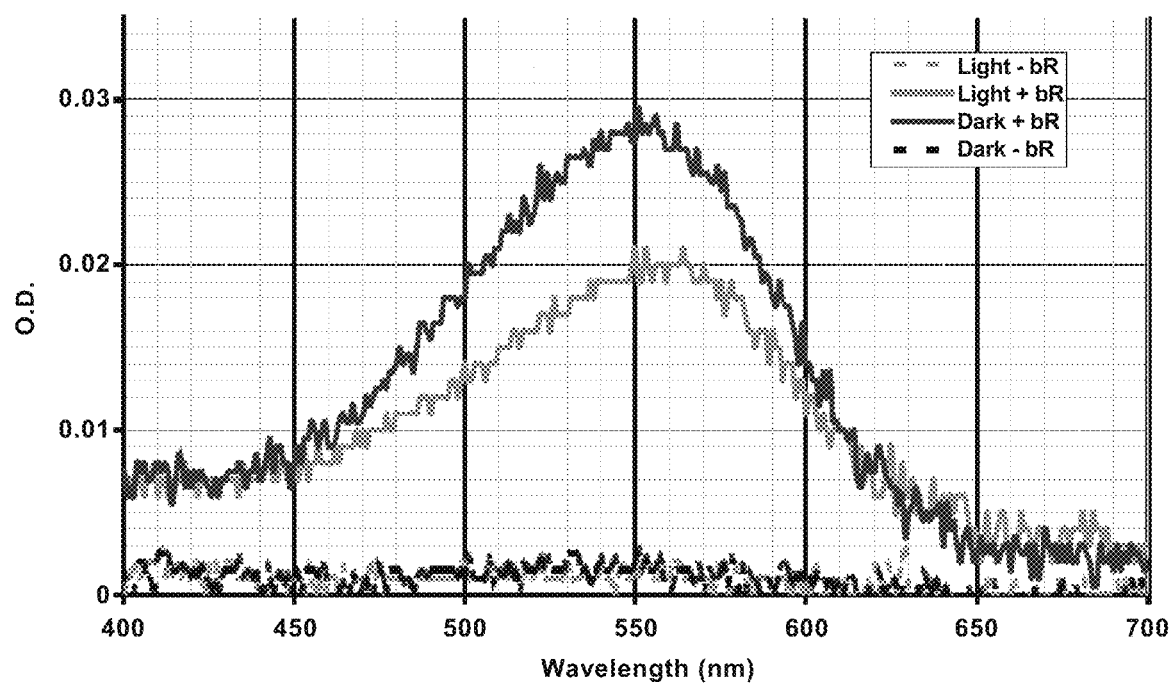
FIG. 17 shows a diagram illustrating the light and dark adapted visible spectra of bacteriorhodopsin associated NLPs, according to an embodiment herein disclosed. (Top traces) Light and dark adapted visible spectra of bacteriorhodopsin associated NLPs and (bottom traces) NLPs without membrane protein. Black) Dark adapted spectra (bR $\lambda_{max}$=550 nm). Grey) Light adapted spectra (bR $\lambda_{max}$=560 nm)
Figure 18:
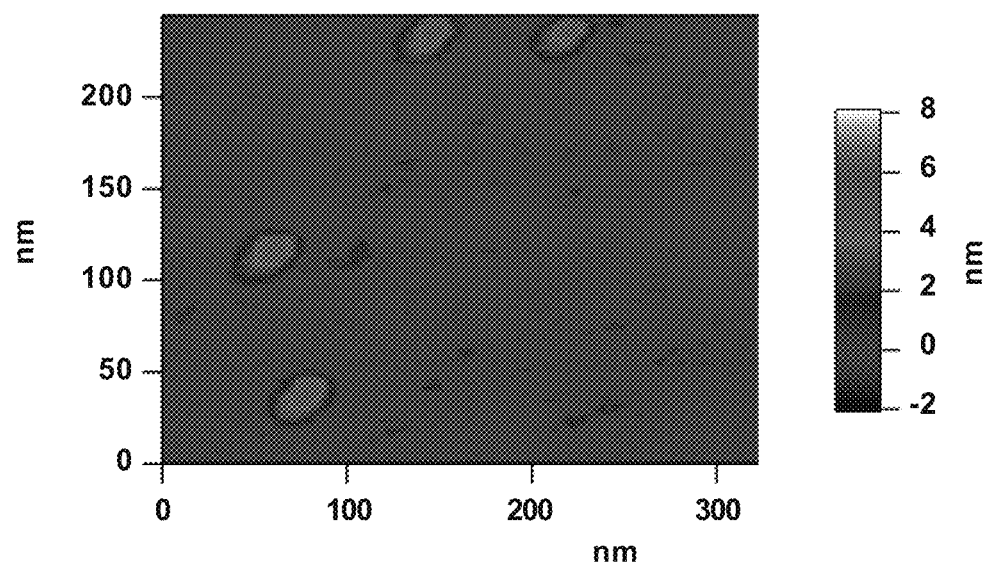
FIG. 18 shows a diagram illustrating the Atomic Force Microscopy of nanolipoprotein particles (NLPs) according to an embodiment herein disclosed. NLPs consisting of cell-free produced apoE4 22K lipoprotein and DMPC. Particle dimensions are as follows; Height: 4.94 nm, std dev: 0.369 nm Width of top: 9.72 nm, std dev: 1.50 nm, Full width at half max: 20.4 nm std dev: 3.5 nm
Figure 19:
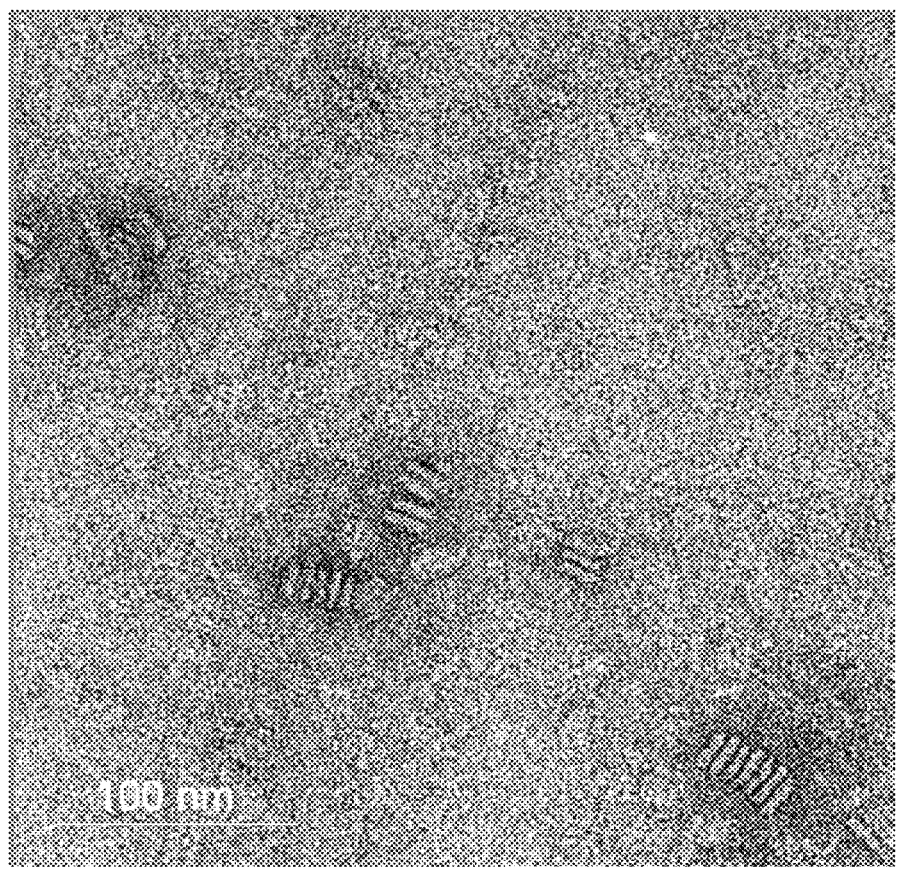
FIG. 19 shows the results of the electron microscopy of nanolipoprotein particles (NLPs) according to an embodiment herein disclosed wherein the NLPs show a discoidal shape. The magnification is 40K

UV-visible spectra were collected in 96-well plate reader using 100 μL of sample in a UV detectable flat bottom plate. Dark adapted spectra were collected after keeping the sample wrapped in foil overnight taking care not to expose the sample prior to spectral collection. Light adapted spectra were collected after exposure to a full spectrum bright lamp for 15 min. The results are illustrated in FIG. 17. A 5-10 nm visible shift between light and dark adapted spectra indicates a functional protein (4).

Further in-depth physical characterization of these particles was used to demonstrate functional protein insertion/association. Combined with the biochemical evidence methods such as Atomic force microscopy (AFM) and Electron microscopy (EM) addresses whether the end product of self-assembly/association was successful by determining physical parameters to identify insertion and localization of membrane proteins. Atomic force microscopy (AFM) (FIG. 18), and Electron microscopy (FIG. 19) although not fully described here, but are used to image the prepared discs and determine diameter and height measurements as well as sample heterogeneity.

Example 12: Membrane Protein Synthesis and Purification in a Single Step Using Cell-Free Synthesis in Conjunction with Pre-Formed Nanolipoprotein Particles (NLPs)

The methods described below membrane protein synthesis and determination of solubility in a single step using cell-free synthesis in conjunction with pre-formed nanolipoprotein particles (NLPs).

Cell-free expression of membrane proteins has usually employed either of two possible methods; one: expression and purification in a denatured state followed by refolding in the presence detergents and/or lipids as well as any cofactors such as all trans-retinal for bacteriorhodopsin or two: expression in the presence of detergents or lipids (2, 13-15). Solubilization of the membrane protein with detergent is generally followed by a dialysis step to return the membrane protein to a lipid bilayer vesicle. The method described here utilizes preformed NLPs as an additive to increase the membrane protein production, solubility and stabilization by incorporation into a NLP lipid bilayer (Co-translation). The procedure uses commercially available cell-free extracts with the addition of membrane protein plasmid DNA (pEXP4 expression vector (Invitrogen)), and pre-formed NLPs to synthesize folded functional membrane protein in one step.

Cloned membrane protein cDNAs of interest were into the expression plasmid pEXP4 (Invitrogen) and were propagated by transforming into Top10 or DH5α □chemically competent cells (Invitrogen). Isolate plasmid DNA using a HiSpeed Plasmid Maxi or Midi Kits (Qiagen).

Cell-Free expression reactions were carried out using the Expressway™ Maxi Cell-Free *E. coli* Expression System (Invitrogen) protocols with the addition of ~15 μg of membrane protein DNA, for a 1 mL reaction, 300 μg of purified NLPs (ApoE4 22 k assembled with DMPC see above section). For scintillation counting the manufacturer protocol for the incorporation of 35S-Methionine was followed. Reactions were scalable to other volumes following the same ratios. Control experiments were carried out without the addition of NLPs using the same lysate batch.

The reactions were incubated at 37° C. shaking at 225 rpm in a shaker incubator (New Brunswick). The reactions were continued for 1.5-2 hours.

A 5 μL aliquot of the total (T) reaction was retained for SDS-PAGE and autoradiograms (not shown), the reaction was then centrifuged for 5 min. at 4° C., and 18000 RCF. The supernatant was collected and a 5 μL aliquot of the soluble (S) fraction placed into a 12×75 mm glass tube.

100 μl of 1N NaOH was added and the resulting mixture was incubated at room temperature for 5 minutes. 2 ml of cold 10% TCA (trichloroacetic acid) were further added to the 12×75 mm tube. Place at 4° C. for 10 minutes.

The precipitate was collected via vacuum filtration through a Whatman GF/C glass fiber filter (or equivalent). The filter was pre-wetted with a small amount of 10% TCA prior to adding the sample.

The tube was rinsed twice with 1 ml of 10% TCA and then rinsed once with 3-5 ml of 95% ethanol. Each of the rinses was passed through the GF/C filter.

The filter was placed in a scintillation vial, aqueous scintillation cocktail was added, and counted in a scintillation counter. The cpm did reflect the amount of radiolabel that was incorporated.

Figure 20:
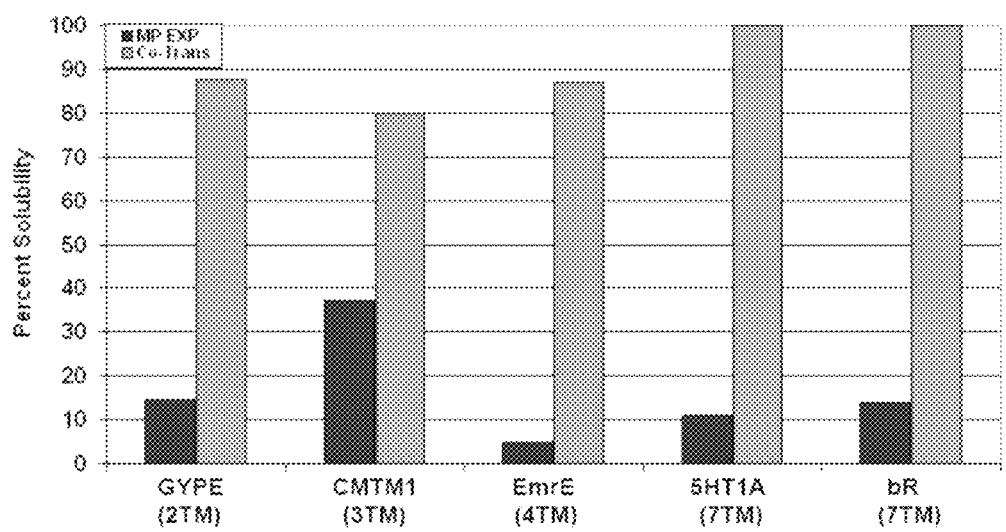
FIG. 20 shows a diagram illustrating cell-free expression of membrane proteins in the presence of NLPs (Co-translation) according to an embodiment herein disclosed. The membrane protein expressed alone is indicated with black bars; the membrane protein expressed in the presence of pre-formed ApoE4 22 k NLPs (Co-Translation) is indicated with grey bars. Membrane proteins with the number of trans membrane domain in parentheses are (GYPE) glycophorin B (MNS blood group) (2TM), (CMTM1) CKLF-like MARVEL transmembrane domain (3TM), (EmrE) *E. coli* SMR efflux transporter (4TM) (5HT1A) 5-hydroxytryptamine (serotonin) receptor (7 TM), (bR) bacteriorhodopsin (7TM).

FIG. 20 shows protein yield for the soluble (S) fraction based on scintillation counting of incorporated 35S-Methionine in the presence and absence of added NLPs.

In particular, in FIG. 20, a comparison was made between the membrane protein expressed alone (Black bars) or in presence of pre-formed ApoE4 22 k NLPs (Co-Translation) (Grey bars).

In all cases the expression in the presence of NLPs increased membrane protein solubility. Solubility is determined by removing a 5 ul of the reaction supernatant after a 10 minute centrifugation at 14000 rpm and determining yield by TCA precipitation and scintillation counting as described in section 3.6.

A survey of several membrane proteins with various numbers of transmembrane (TM) segments are expressed using this method. Solubility of the membrane protein is clearly increased in the presence of pre-formed NLPs indicating association with the NLP.

Example 13: Cell-Free Production of NLPs

In a further series of experiments performed following the approach outlined in Example 1 and illustrated in FIG. 1, preparative reactions were carried out using the Invitrogen's Expressway Maxi kit and/or for comparison the RTS High Yield Kits as outlined below.

Basically, lyophilized reaction components (Lysate, Reaction Mix, Amino Acid Mix, Methionine) were dissolved in Reconstitution Buffer and combined as specified by the manufacturer. Then, 1-5 μg of each plasmid DNA were added and the reactions are incubated at 30 DC-37 DC for 14-24 h. Small-scale reactions, can make use of PCR products. This is especially convenient for conducting screening experiments in volumes as low as 2 μL. PCR products are quantified using a fluorescence-based IpicoGreen assay Then 0.1 μg of linear template DNA is added to initiate the reaction, which is incubated at 30 DC for 4 h.

For expression screening, reactions were performed in 12-25 μL volumes and the resulting products were analyzed by immunoblotting or using a 96-sample format dot blot or array using previously described techniques adapted to NLP-GPCRs.

The DNA constructs to produce the scaffold proteins E422K, E22K, and apoLp-III from *B. mori* were provided.

The ApoAI and MSPI (truncated form of ApoAI) were also cloned (see Table 3 of Example 16 below).

In general, the bacterial overexpression of these scaffold proteins was started by transferring 20 ml of a bacterial overnight culture into I LM9 minimal medium supplemented with 50 µg/l ampicillin. The expression was induced with 2 M isopropyl-thio-galactopyranoside (IPTG) at an OD600 nm of 0.55. Four hours later the bacteria were centrifuged (10 min, 4500 rpm, Beckman JA 10), the supernatant filtrated (0.8 urn) and subsequently concentrated to a volume of 2 ml by ultrafiltration through a 10 kDa membrane (Amicon). The concentrate was heated for 5 min at 100° C., centrifuged (15 min, 13,000 rpm, EPPENDORF® 5415 C), and the supernatant was exchanged against 20 mM BisTris (pH 6.5) by 3-kDa ultrafiltration (Centriprep, Amicon). The prepared sample as applied onto a DEAE-Sepharose CL-6B anion exchange column (bed volume 20 ml, Sigma) connected with a Gradifrac-system (Pharmacia). Flow rate was I ml/min, and I.-ml fractions were collected. The late fractions of the flow-through containing apoLp-III were pooled, exchanged against physiological saline (172 mM KCl, 68 M NaCl, 5 mM $NaHCO_3$, pH 6.1) and applied in a volume of 2 ml onto a gel filtration column (HiLoad 16/60, SUPERDEX™ 75, Pharmacia) operated with an FPLC system (Pharmacia). Protein purity was checked by sodium dodecylsulfate-polyacrylamide gel electrophoresis (SDS-PAGE).

Lipid (20 mg) was weighed out and combined in a glass, round bottom tube. Chloroform (200 µl) was added to dissolve lipid. Chloroform is evaporated in a stream of nitrogen gas, rotating rapidly to distribute the lipid evenly. Samples are placed under vacuum for 30 min. to assure removal of solvent. The individual components are placed into an assembly solution with the appropriate ratios of lipid (800 µg), scaffold protein (200 µg), detergent (21 mM), creating a mass ratio of 4:I for lipid to protein and maintaining the cholate above the critical micellar concentration. The self-assembly process is started with 3 repeated sets of transition temperature incubations, bracketing the transition temperature of DMPC (23.80 C), by incubating at 30° C. for 10 minutes, then at 20° C. for 10 minutes with light hand mixing between incubations.

Following these transitions, the samples are incubated at 23.8° C. overnight. Following assembly, samples with cholate are dialyzed against 1000× volume of TBS buffer using 3 changes in 24 hrs. The NLPs are purified from 'free protein' and 'free lipid' by a VP HPLC (Shimadzu) with a SUPERDEX™ 200 HR 10/30 column (GE healthcare), using TBS at a flow rate of 0.5 ml/min. The column was calibrated with four protein standards of known molecular weight and stokes diameter that span the separation range of the column and the NLP samples.

The void volume was established with blue dextran. The NLP fraction is concentrated about 10-fold to ~approximately 0.1 mg/ml using molecular weight sieve filters (Vivascience) having molecular weight cutoffs of 50 kDa. Protein concentration was determined using the ADVOI protein concentration kit (Cytoskeleton), which is based on Coomassie dye binding.

To performed Native PAGE validation, equal amounts of NLP samples (0.5-2 µg) were diluted with 2× native gel sample buffer (Invitrogen) and loaded onto 4-20% gradient pre-made Tris-glycine HCl gels (Invitrogen). Samples were electrophoresed for 250 V/hrs at a constant 125 V. After electrophoresis, gels are incubated with SYPRO® Ruby for 2 hours and then de-stained using 10% MeOH, 7% Acetic acid. Following a brief wash with ddH20, gels are imaged using the green laser (532 nm) of a Typhoon 9410 (GE-Healthcare) with a 610 nm bandpass 30 filter.

Molecular weights were determined by comparing migration vs. log molecular weight of standard proteins found in the NativeMark standard (Invitrogen). The Stokes diameter of the NLPs is calculated from the known Stokes diameter of the same proteins in the standard sample.

Example 14: Characterization of NLPs Produced by Cell-Free Systems: Solubilization of the bR-NLP Complex The experimental approach described in Example 13 was applied to obtain cell free expression for single step production and refolding of the membrane protein bacteriorhodopsin (bR) from *Halobacterium alinarium*, which serves as model protein for G-protein coupled receptors (GPCRs), an important membrane protein family.

Figure 21:
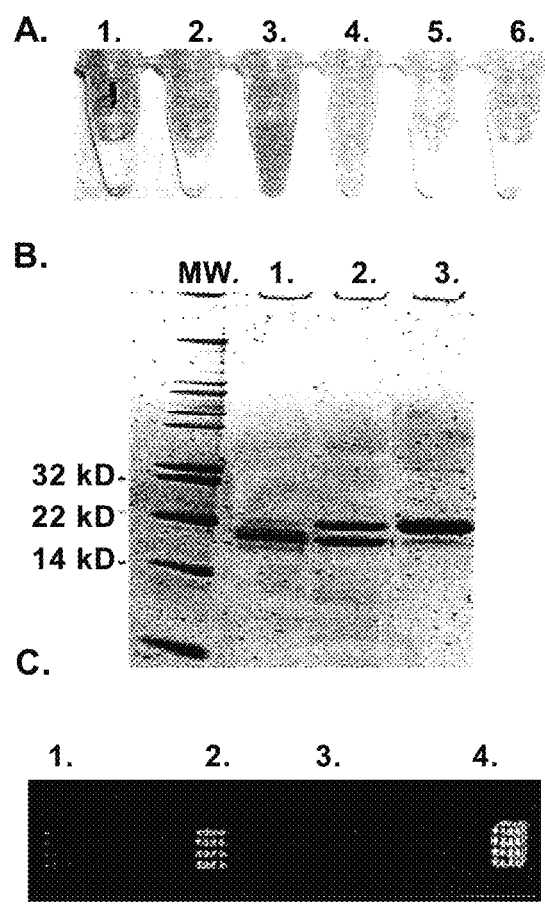
FIG. 21 shows the results of experiments related to cell free production of a membrane protein in the presence of NLP scaffold according to an embodiment herein disclosed. Panel A shows the cell free production of bR with a cell free extract, Lane 1. bOp+retinal, Lane 2. bOp alone Lane 3. bOp+Lipid+retinal, Lane 4. Apolipoprotein+bOp+Lipid+ Retinal 5. Apolipoprotein+bOp+Lipid, 6. Apolipoprotein alone, 7. Apolipoprotein+bOp+Retinal. Panel B shows the results of PAGE analysis of size exclusion purified proteins or NLP associated with bR. Lane 1. bR, Lane 2. bR+NLP, Lane 3. NLP. Panel C shows microarray analysis of purified bR associated with NLPs using an anti-biotin antibody. Lane 1. bR only, Lane 2. Size exclusion purified biotinylated bR-NLPs. Lane 3. NLPs only. Lane 4. Biotinylated IgG.
Figure 22:
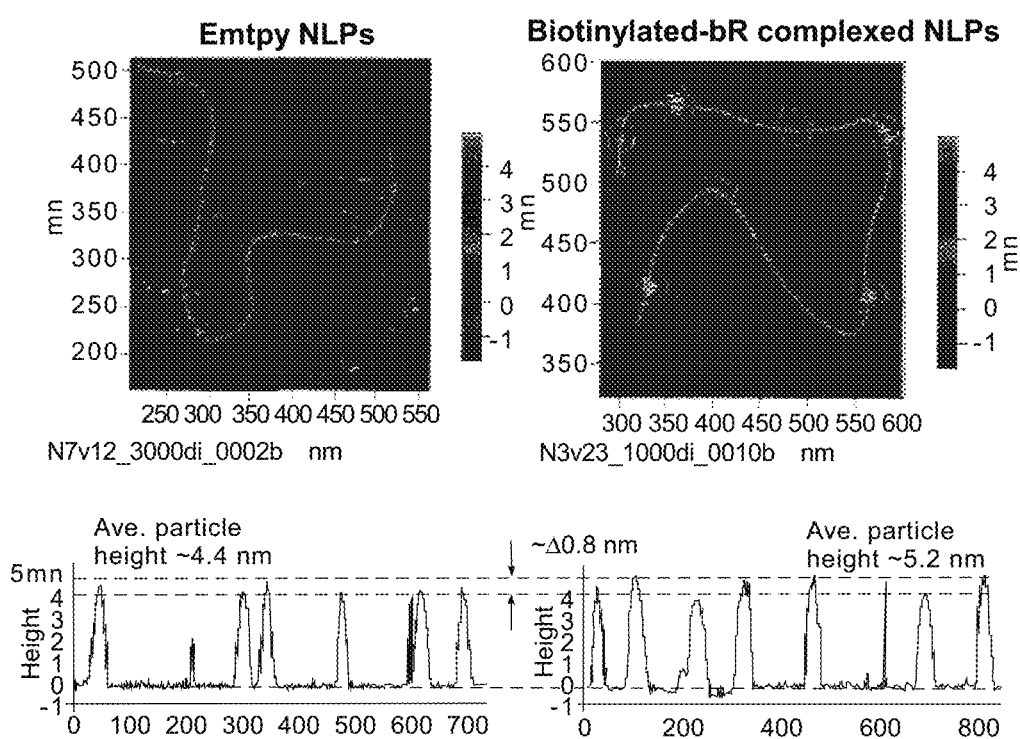
FIG. 22. shows the results of experiments related to the cell free production of NLPs according to an embodiment herein disclosed illustrated by Atomic force microscopy (AFM). The AFM can resolve membrane surface features at a lateral resolution of 0.6-1 nm and a vertical resolution of 0.1 nm, under physiological conditions without the need of a crystalline system. AFM of NLPs with and without biotinylated bR are shown. Note, homogeneous globular structures about 5 nm in height and 20-60 nm in diameter.
Figure 23:
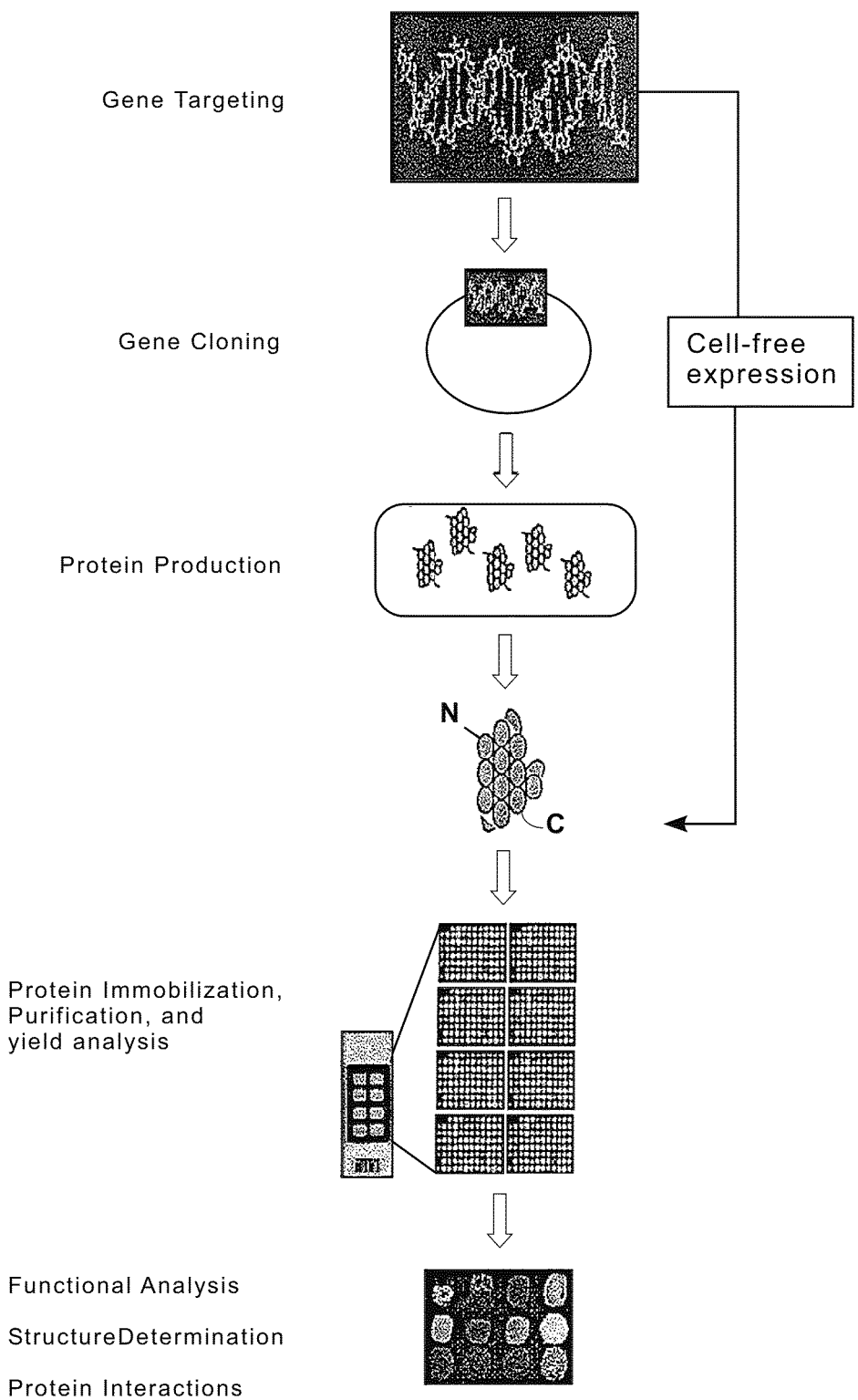
FIG. 23 shows a schematic illustration of proteomics carried out using cell-free expression linked to protein microarrays that are applicable to certain embodiments herein disclosed.
Figure 24:
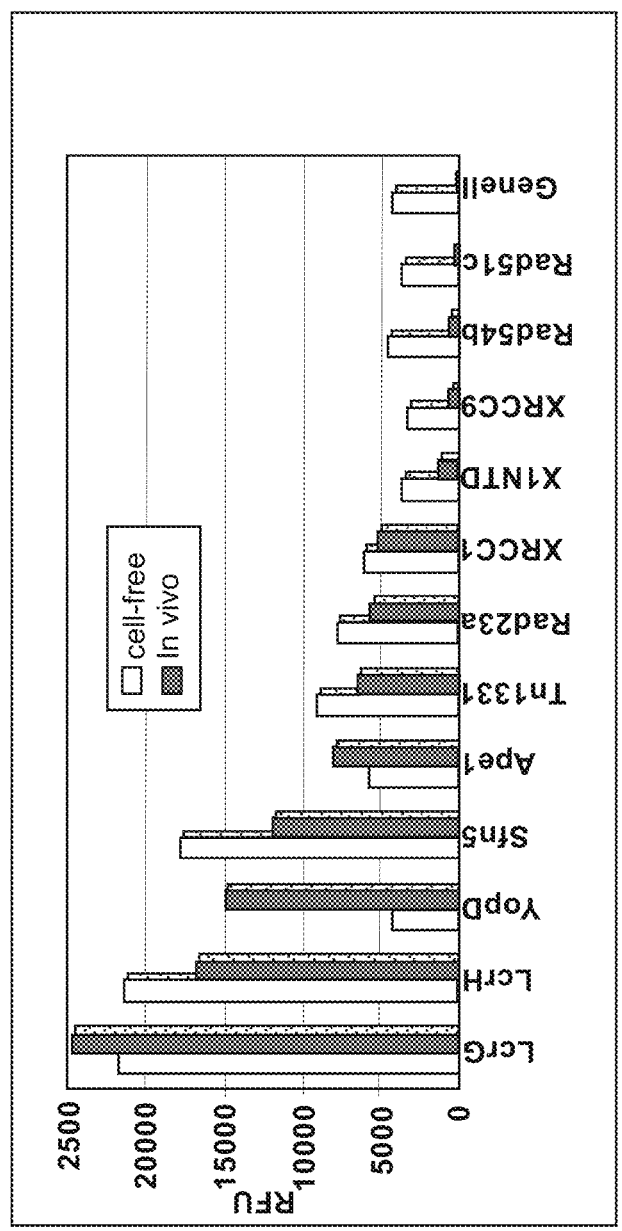
FIG. 24 shows a diagram illustrating the correlation of *E. coli*-based in vivo and cell-free protein expression levels. Proteins were expressed cell-free using *E. coli* extracts or in *E. coli* cultures. Proteins were expressed as GFP fusions, lysed and the soluble fraction was transferred to a 96 well plate and the fluorescence quantified. The correlation coefficient (cc) was 0.89 for the 9 most highly expressed proteins and the overall cc was 0.69.

Cell-free expression of bR in the presence of NLPs is shown in FIGS. 21 and 22. Preliminary results show that cell-free synthesis of bR in the presence of NLPs yields nanoparticles containing bR, i.e. NLP-bR.

Additionally, these NLP-bR constructs are funcIllJnal as assessed by UV/Vis spectrometry (data not shown). The bR protein is only purple when co-factors are present to allow proper protein folding The figure also demonstrates that the bR protein is incorporated within the NLP following size exclusion chromatography to purify and isolate the complex (FIG. 21, Panel B). The bR containing NLPs were also assayed using a Western microarray format as preliminary development of rapid fluorescent screening techniques (FIG. 21, Panel C) and by Atomic Force Microscopy, which showed an increase in particle height (FIG. 22). Interestingly, co-expression in RTS or Expressway) cell-free reactions of an apolipoprotein (scaffold protein) with two other membrane protein targets showed significantly enhanced soluble expression levels (FIG. 22). These results, suggesting similar incorporation of membrane protein into NLPs, support the claim of a single step reaction process yielding soluble NLP/membrane protein constructs. These results therefore establish cell-free co-protein expression as a viable expression strategy for membrane proteins in general, which comprise a significant fraction of any genome and are notoriously difficult to isolate and characterize.

Example 15: Cell-Free Protein Expression Screening and Protein Immobilization Using Protein Microarrays Combining array-based technologies with cell-free expression is a recent development for highly parallel strategies to analyze protein functions (see FIG. 23). According to the approach shown in FIG. 23 the proteomics is broken down into five major components, as shown on the left of the scheme, with the net outcome being sufficient yield of soluble protein for subsequent characterization studies. Methodologies using cell-free transcription and translation may enhance the throughput of such projects by circumventing the time consuming steps of cloning, protein production, immobilization and functional characterization. This approach has been used to provide both proteins for spotting as well as means to produce self assembled arrays by transcribing and translating protein directly from spotted DNA or PCR products. A disadvantage of these techniques to date, is the lack of selective immobilization and stabilization of the arrayed proteins.

To validate the use of cell-free protein expression screening for compatibility with bacterial expression, the correlation of cell free and bacterially-expressed proteins was first examined using C-terminal OFP fusion proteins 40-42

Cloning and Bacterial Expression

For the construction of C-terminal GFP fusion proteins 69, a set of microbial genes and human cDNAs were amplified with primers containing restriction site adapters for NdeI and BamHI and a high-fidelity polymerase, Fwo DNA polymerase (Roche Diagnostics). The PCR products were digested with NdeI and BamHI restriction enzymes and subcloned into the pET28-derived plasmid for GFP-fusion 69 using the same restriction sites. Genes were expressed as Cterminal GFP fusion proteins in 2 mL *Escherichia coli* cultures, grown in LB media at 37° C. with vigorous shaking until mid-exponential phase (00600=0.6) was reached, and expression was induced with 1 mM IPTG. Cultures were grown for an additional 2 h and harvested by centrifugation. Fluorescence of GFP was determined from the soluble fraction of bacterially or IVT-expressed proteins. Detection and quantification of GFP fluorescence was carried out in a 96-well Genios fluorescence plate reader (Tecan).

Template Preparation and Cell Free Reactions

Expression screening—Sequential PCR and IVT reactions were performed in 25 µL volumes in 96-well plates. DNA amplification was performed using primers specific to the T7 promotor (5'-GCGCGCGAGATCTC-GATCCCGCGAAATTAATACGAC-3') (SEQ ID NO: 6) and terminator (5'GCGCGCGTATCCGGA-TATAGTTCCTCCTTTCAG) (SEQ ID NO: 7) sequences and Taq DNA polymerase (Roche Diagnostics). PCR conditions consisted of 5 cycles with a 50° C. annealing temperature followed by 20 cycles with a 60° C. annealing temperature, with 2 min extension times for all cycles. Subsequent IVT reactions contained 1 J1L of the PCR reaction product and 20 J1L of a master mix containing the RTS kit components and 0.13 J1L of a BODIPY-Lys-tRNALY' conjugate, FluoroTect GreenLy, (Promega). The reactions were incubated at 30° C. for 4 h and analyzed immediately or stored at −20° C. pMBP-IN—The gene fragment encoding DnaE-IN with 4 N-terminal extein residues (FAEY) was amplified by polymerase chain reaction (PCR) using a plasmid containing the DnaE genes from of *Synechocystis* sp. strain PCC6803 (Ssp) as templates.

The 5'-primer (5'-TG AAA TTC TTT GCG AAA TAT TGC CTC AGT TTT GG-3') (SEQ ID NO: 8) and the 3'-primer (5'-TTT GGA TCC TTA TTT AAT TGT CCC AGC GTC AAG TAA TGG AAA GGG-3') (SEQ ID NO: 9) introduced EcoRI and BamHI restriction sites, respectively. The PCR amplified DNA was purified, digested simultaneously with EcoRI and BamHI and then ligated into a EcoRI, BamHI-treated pMAL-C2X plasmid (New England Biolabs).

pTXBI-Ic—The gene fragment for the DnaE-Ic was prepared by PCR using a plasmid containing the DnaE genes from of *Synechocystis* sp. Strain PCC6803 (Ssp) as template59 The 5'-primer (5'-AAAA AGG CAT ATG GTT AAA GTT ATC GGT CGT CGT TCC CTC-3') (SEQ ID NO:10) and 3'-primer (5'-TAA AAT GGC TCT TCG GCA ATT GGC GGC GAT C-3') (SEQ ID NO: 11) introduced Nde I and Sap I restriction sites, respectively. The PCR product was purified, double-digested with Nde I and Sap I and ligated into an Nde I, Sap I-treated pTXB-I plasmid (New England Biolabs).

pIVEX-MBP-Itl—The DNA fragment encoding the protein MBP-IN was prepared by digesting pMBP-IN with Nde I and BamH I restriction enzymes. The DNA fragment was purified and inserted between the Nde I and BamH I restriction sites of the pIVEX2.3 plasmid (Roche Diagnostics).

Protein Microarray Spotting and Detection

To analyze GFP proteins in an array format, crude IVT-expressed proteins (~I nL) were spotted in triplicate on CMT-GAPS glass slides (Corning) with a robotic arrayer (Norgren Systems). Arrays contained up to 224 spots of ~200 µm diameter. Spotting controls included IVT lysate alone and Cy-labeled DNA fragments (Molecular Probes). The arrays were dried at 25° C. and stored at 4° C. until use. Fluorescence was quantified using a ScanArray 5000 (Packard Bioscience) and visualized with false color. Functionalization of glass substrates—Glass slides coated with gaminopropyl-silane (GAPS WM; Corning) were treated with 200 µL of a solution of MPS (3-maleimidopropionic acid N-hydroxysuccinimide ester, 2 mM) in O. I M TrisoHCl buffer at pH 7.5 for 40 min at room temperature using a hybridization chamber (Schleicher & Schuell, Keene, N.H.). The glass slides were washed with deionized H20, MeOH, and dried under a N2 stream. The modified glass slides were immediately treated with 200 µL of a solution of thiol linkers 1 (0.05 mM) and 2 (1.5 mM) in freshly degassed 0.5 mM EDTA, 1 mM TCEP, 50 mM sodium phosphate, 150 mM NaCl buffer at pH 7.0 for 16 hours at room temperature. After the glass slides were washed and dried as described above, the S-tBu protecting group on the C-terminal Cys residue was deprotected by treating the glass slides with 50% ~-mercaptoethanol in DMF for 2 h at room temperature.

The glass slides were washed with deionized HzO, MeOH, dried under a N2 stream and used immediately. Generation of protein microarrays for protein immobilization—Protein solutions (0.1 mM-40 mM) in spotting buffer (0.5 mM EDTA, 1 mM TCEP, 50 mM sodium phosphate, 150 mM NaCl buffer at pH 7.0 containing 10% glycerol) were arrayed in functionalized glass slides using a robotic arrayer (Norgren Systems). Proteins were spotted with a center-to-center spot distance of 250 µm with an average spot size of 100 µm in diameter. After spotting, the array was kept in a humidified chamber at 37° C. for 16 h. The glass substrate was thoroughly washed with PBST (50 mM sodium phosphate, 500 mM NaCl buffer at pH 7.2 containing 0.2% Triton X-100). Immobilized EGFP was imaged using a ScanArray 5000 at 488 nm without further modification. Immobilized MBP was detected by immunofluorescence at 543 nm using a primary murine anti-MBP antibody and then a secondary goat anti-mouse antibody conjugated to TRITe (tetramethylrhodamine isothiocyanate). The amount of fluorescence was quantified using the QuantArray software package (Packard Bioscience, Billerica, Mass., USA).

Fluorescence-Based Protein Microarray Expression Screens

The clones of interest encoded both human and bacterial proteins. The expression data could be grouped into two subsets (FIG. 24), the more highly expressed clones for which the correlation was good (cc=0.89) and the more poorly (in vivo) expressed clones for which the correlation was weaker (overall cc=0.69). For the latter clones, the cell-free expression levels were consistently higher than those in vivo. Therefore, those data support the conclusion that this set comprises proteins that are either cytotoxic or proteolytically sensitive, which underscores the benefits of cell-free expression for certain classes of proteins that are expressed at low levels in cell-based systems. Notably four of the five proteins were produced at significantly higher quantities using the cell free system. These proteins are DNA repair proteins, which can be difficult to express, suggesting that cell-free expression may be particularly useful for production of difficult classes of proteins.

Figure 25:
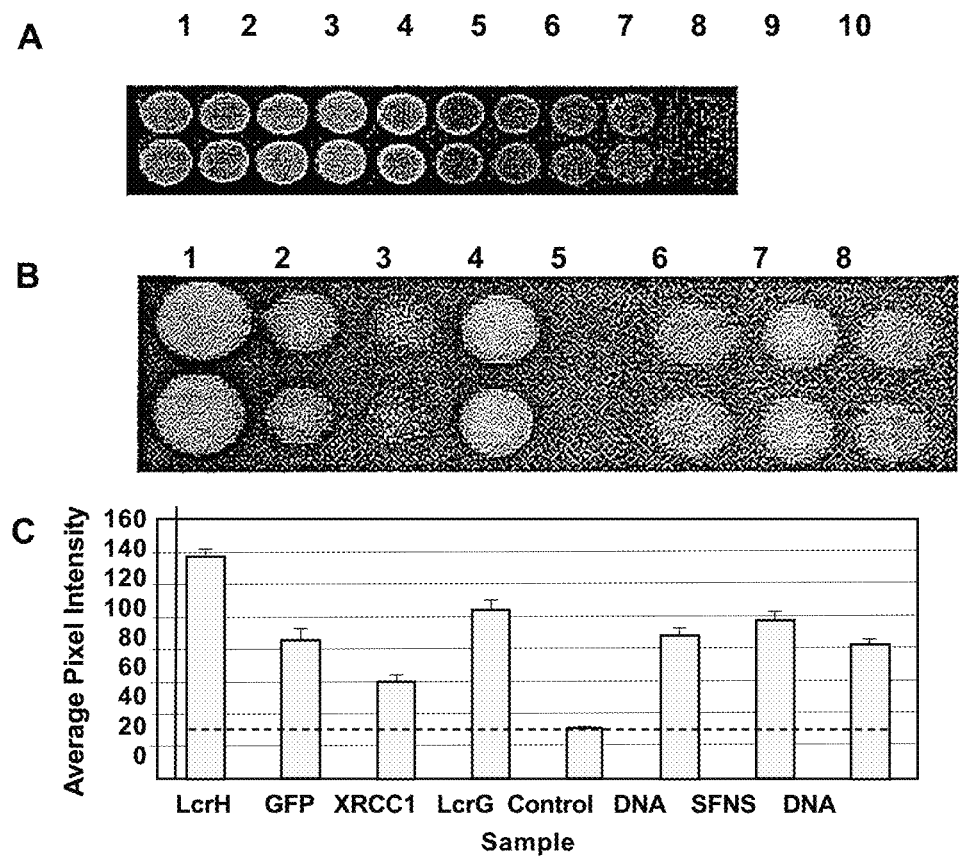
FIG. 25 shows the results of a microarray-based expression screening according to an embodiment herein disclosed. Panel A shows known amounts of GFP diluted for array quantification and falsely colored red. Panel B shows in green, GFP fluorescence; red, Cy3 labeled DNA. Column I, LcrH; 2, GFP; 3, XRCCI; 4, LcrG; 5, Lysate control; 6, DNA; 7, SFN5; 8, DNA. Panel C shows a diagram illustrating how the spot intensity is reproducible and correlates with expression levels observed as detected with a plate reader or by spotting onto a nylon membrane. The error bars indicate the standard deviation among four replicates and the dashed line illustrates background fluorescence.
Figure 26:
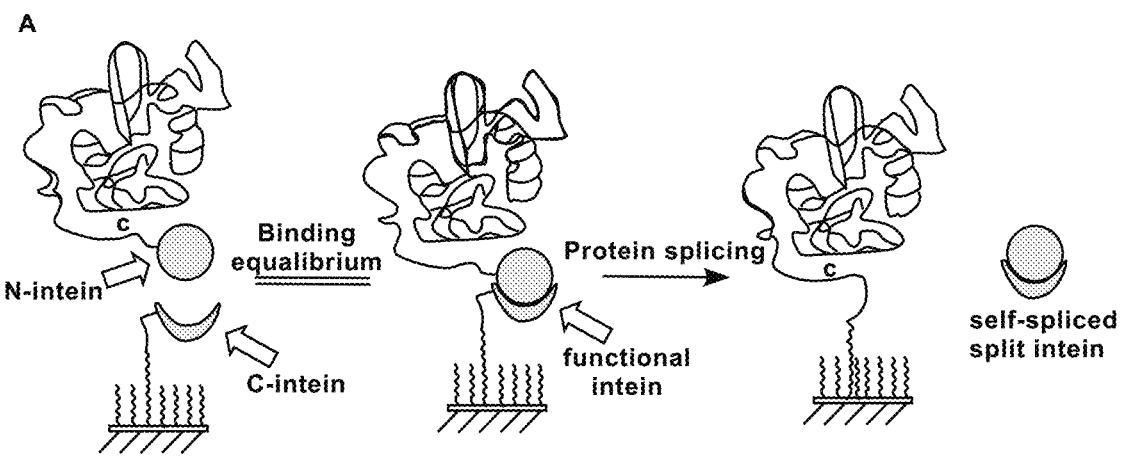
FIG. 26 shows a general scheme for the site-specific and traceless immobilization of proteins through protein transsplicing applicable to certain embodiments herein disclosed. Panel A
Figure 26:
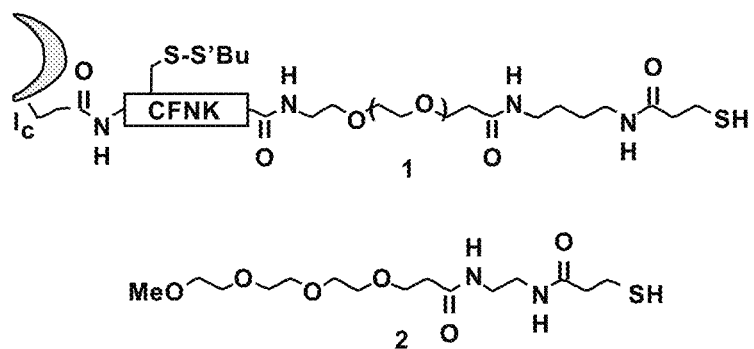

Cell-free expressed proteins were then spotted on microarray format for multiple applications. First, as a tool for rapid expression screening, in which the arrayed proteins were compared for relative expression levels. In particular, cell-free expressed GFP and GFP fusion proteins were spotted in quadruplicate on a glass slide (See FIG. 25 where only duplicates are shown) for analysis of yields. One nL of the reaction was spotted in a spot of approximately 100 µm in diameter. Control experiments with known amounts of GFP were conducted to bracket the limit of detection for GFP fluorescence on a glass slide (FIG. 25, Panel A). Next, GFP fusion proteins were in vitro expressed and arrayed directly to demonstrate that spotting was reproducible and therefore useful to quickly identify relative differences in expression levels (FIG. 25, Panels B and C). Such arrays are also useful for protein-specific detection, as performed by array-based immunoassays to detect GFP fusion proteins (data not shown). These sorts of experiments can also be easily adapted for automated protein expression profiling studies. Once sufficient expression is established based on fluorescence detection strategies, these approaches can be used to obtain native or tagged versions of the desired proteins.

Overall, in vitro expression and detection methods are relatively rapid since they require no electrophoresis or transfer to membranes. In addition, the detection method were flexible, and could use either fluorescent fusion proteins or covalently incorporated labels 43,44 Cell-free expression in conjunction with Cterminal tags such as His6 may also have an advantage for detecting exclusively full-length translation products. Since BODIPY molecules may affect the conformation of the protein, immunological detection of unlabeled proteins may be preferable if the resulting protein will be used for functional assays. BODIPY labeling would be preferable if no tag or a variety of tags is present on different expression clones. Alternatively, immunological detection may be employed using antibodies against affinity tags, or native proteins may be visualized with 35S-Met. These flexible approaches for cell-free protein expression enable automated production of many proteins and their subsequent purification. Coupled with label-free array-based technologies such approaches will become very powerful in the future 45

Array-Based Site-Specific and Traceless Immobilization of Cell-Free Expressed Proteins A key element for the rapid and efficient production of protein microarrays using cell-free expression systems is the method of protein immobilization. In order to be successful it has to be able to selectively immobilize the protein of interest from a complex mixture and under diluted conditions, typically around lower than µM concentrations. During the last few years several enzymatic capture approaches have been developed for the covalent and site-specific immobilization of enzyme-fusion proteins from complex mixtures without the need for purification and reconcentration steps. Most of them rely in the expression of the protein of interest fused to an enzyme (typically an esterase or transferase) that is selectively immobilized onto an appropriate ligand coated surface. One of the main limitations of these ligand-capture techniques for site-specific immobilization is that the enzyme remains attached to the surface after the immobilization step has taken place. In some cases, the presence of such a large linker could give rise to problems, especially in those applications where the immobilized proteins will be involved in studying protein-protein interactions within complex protein mixtures.

Figure 27:
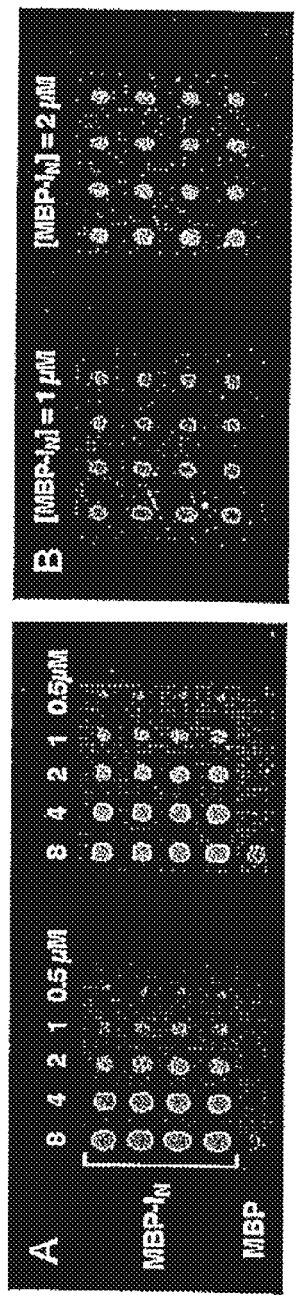
FIG. 27 shows a schematic illustration of a selective immobilization of MBP-IN from complex mixtures using protein through protein trans-splicing according to an embodiment herein described; Panel A shows soluble cellular fraction of *E. coli* cells over expressing MBP-IN. Penal B shows MBP-IN expressed in vitro using a cell-free system. Protein concentrations in the cell lysate and IVT crude reaction were estimated by Western Blotting. In both cases, MBP was detected by immunofluorescence on the slide after several washing steps.

To address this problem, a new traceless capture ligand approach was developed for the selective immobilization of proteins to surfaces based on protein trans-splicing process (FIG. 26A). This process is similar to protein splicing with the only difference being the intein self-processing domain is split in two fragments (called N-intein and C-intein, respectively) In our approach, the C-intein fragment is covalently immobilized onto a glass surface through a PEGylated-peptide linker while the N-intein fragment is fused to the C-terminus of the protein to be attached to the surface (FIG. 26B). When both intein fragments interact, they form an active intein domain, which ligates the protein of interest to the surface at the same time the split intein is spliced out into solution (FIG. 27). The trans-splicing reaction mediated by the split intein results in the direct covalent attachment of the protein through its C-terminus onto a PEGylated surface. A direct covalent attachment between the protein and the surface using poly-ethylene glycol (PEG) linkers eliminates the need for enzymatic and other protein mediators. These PEG-based linkers are also very well know to prevent non-specific interactions and act as hydrophilic spacers minimizing any detrimental interaction between the attached protein and the solid surface.

Figure 28:
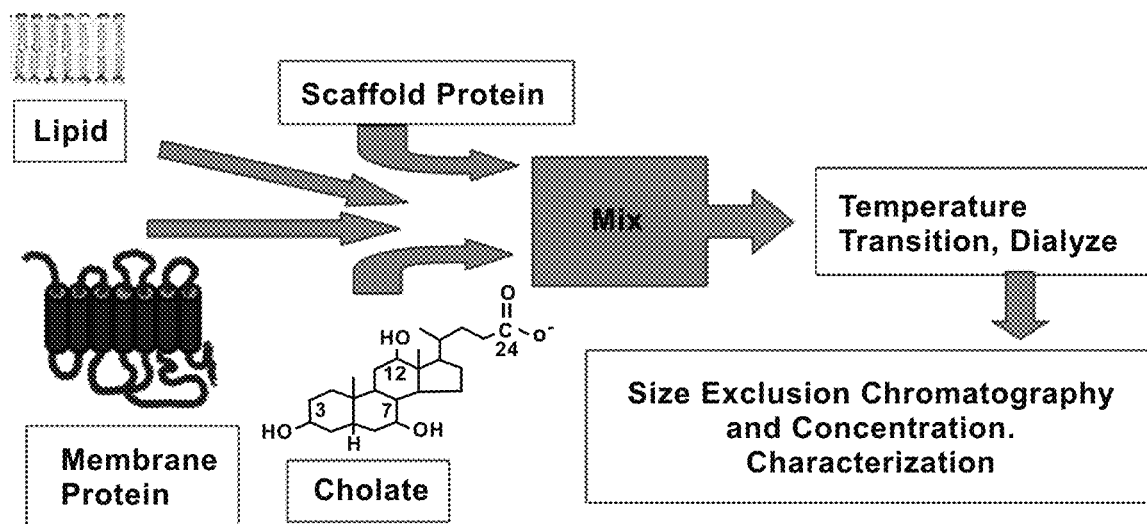
FIG. 28 shows the schematic of NLP assembly according to an embodiment herein disclosed.

Key to this approach is the use of the naturally split DnaE intein from *Synechocystis* sp. PCC6803 59 The C- and N-intein fragments of the DnaE intein are able to self-assemble spontaneously (Kd=0.1-0.2 µM), not requiring any refolding step 30,60 The DnaE intein-mediated trans-splicing reaction is also very efficient under physiological-like conditions (LI2''' 4 h and trans-splicing yields ranging from 85% to almost quantitative) [30]. Using this strategy, several proteins were successfully specifically immobilized to chemically modify $SiO_2$-based substrates from complex mixtures, including cell-free expression reactions as well as soluble cell lysates (FIG. 28).

Site-specific immobilization of proteins using protein trans-splicing is highly specific and efficient. It allows the use of protein mixtures and eliminates the need for the purification and/or reconcentration of the proteins prior to the immobilization step. The required minimum protein concentration for efficient immobilization was estimated to be sub-micromolar 30 More importantly, once the protein is immobilized to the surface, both intein fragments are spliced out into solution and easily removed by washing, providing a completely traceless method of attachment. All these features allow this methodology to be easily interfaced with cell-free protein expression systems with rapid access to the high throughput production of protein chips and other types of biosensing platforms.

Example 16: apoE422K and apoLp-III Protein Production

Apolipoproteins apo E422K and apoLp-III where selected from the ones illustrated in Table 3 below.

TABLE 3

| Apolipoprotein | Mol. Wt. | Lipid | Cholate | Key REFs |
|---|---|---|---|---|
| ApoAI | 28.1 kDa | DMPC | No | Jonas et al., 1980[8] |
| MSP1T2 (Δ1-55 ApoAI) | 24.8 kDa | DMPC | No | Sligar et al., 2005[9]; Denisov et al., 2005[10] |

TABLE 3-continued

| Apolipoprotein | Mol. Wt. | Lipid | Cholate | Key REFs |
|---|---|---|---|---|
| ApoE422K | 22.3 kDa | DMPC | No | Lu et al, 2000[11] |
| ApoLp-III | 18 kDa | DMPC | No | Weintzek, M. et al. 1994[12]; Weers and Ryan, 2003[13] |
| ApoAI | 28.1 kDa | DMPC | Yes | Jonas et al., 1980[8] |
| MSP1T2 (Δ1-55 ApoAI) | 24.8 kDa | DMPC | Yes | Shaw et al., 2004[14], Bayburt et al., 2006[15] |
| ApoE422K | 22.3 kDa | DMPC | Yes | This work |
| ApoLp-III | 18 kDa | DMPC | Yes | Garda HA et al., 2002[16] |
| Cy3-apoE422K | 22.3 kDa | DMPC | Yes & No | This work |
| Cy3-apoE422K | 22.3 kDa | DMPC + 1% NBD-DMPC | Yes & No | This work |

The expression clone to produce apoE422K, the N-terminal 22 kDa fragment of apolipoprotein E4 (apoE4), as a 6His and thyrodoxin tagged construct was kindly provided by Dr. Karl Weisgraber. ApoE422K was over-expressed and in *E. coli* as previously reported. Pelletted *E. coli* cells expressing apoE422K were re-suspended in lysis buffer (50 mM sodium phosphate, 300 mM sodium chloride, 10 mM imidazole, pH 8.0) and lysed with an Emulsiflex-05 homogenizer (Avestin Inc., Ottawa, Canada) at 4° C. Following centrifugation, the clarified supernatant was first partially purified by nickel affinity chromatography using a 5 ml His Trap FF crude nickel column (GE Healthcare) on an Akta FPLC (GE Healthcare) then further purified with a 320 ml SUPERDEX™ 75 HiLoad 26/60 column (GE Healthcare) using TBS running buffer (10 mM Tris, pH 7.4, 0.15 M sodium chloride, 0.25 mM EDTA, 0.005% sodium azide) giving one predominant peak.

The collected material was cleaved with bovine α-Thrombin (Haematologic Technologies) 1/500 enzyme/protein for 1 hour at 37° C. Resulting products were separated by SEC on a 320 ml SUPERDEX™ 75 HiLoad 26/60 FPLC column with one column volume of TBS. Protein fractions were analyzed by SDS-PAGE gels stained with SYPRO® Ruby (BioRad), gels were imaged with a Typhoon 9410 (GE Healthcare). Relative purity of the proteins was determined to be greater than 95% by densitometry and overall yields are on the order of 6 mg/L bacterial culture.

The *B. mori* apoLp-III expression clone was a kind gift from Dr. Rob Ryan. ApoLp-III was over-expressed in *E. coli* as described. The protein was expressed with a PEL leader sequence, targeting the protein to the periplasm, where the leader sequence is cleaved and protein secreted in to the media. Expression was induced for four hours, bacteria were pelleted and the supernatant was collected, filtered (0.8 µm), and subsequently concentrated to a volume of ~20 ml using a Vivaflow 200 (Sartorius) with a 5-kDa MW cutoff PES membrane. The concentrated protein was exchanged against 20 mM Tris pH 8.0 over a HiPrep 26/10 desalting column on an Akta FPLC (GE Healthcare). The protein was then purified to homogeneity by HPLC (Shimadzu) using a ProPac WAX-10 column (Dionex) and eluted as follows: 0-100% gradient between 20 mM Tris pH 8.0 and 20 mM Tris pH 8.0 with 0.5M NaCl. Fractions showing highest protein content by $A_{280}$ were pooled.

Protein purity was checked by sodium dodecylsulfate-polyacrylamide gel electrophoresis (SDS-PAGE) and mass spectroscopy analysis. The protein was >90% pure by gel electrophoresis, MS analysis gave expected molecular ion peaks; overall yield was 40%.

Fluorescently labeled apoE422K was obtained by using a Cy3 labeling kit and following the manufacturer's instructions (GE Healthcare). Dye:protein ratio was determined by comparing the absorbance of the protein at 280 nm and the absorbance of the CyDye at 532 nm. The ratio provided a 1:1 correlation suggesting that a single Cy3 molecule is present on each apoE422K protein.

Example 17: Nanolipoprotein Particle (NLP) Formation Through Self-Assembly of Lipids and Apolipoproteins In order to better understand the self-assembly process and the range of attributes of NLPs extensive comparison of particles from a number of self-assembly conditions was performed, using four different apoliporoteins, and a battery of characterization techniques, was applied. In particular NLPs from each of the four apolipoproteins apoA-I, Δ-apoA-I fragment, apoE4 fragment, and apolipophorin III (apoLp-III), assembled and characterized in combination with DMPC, with and without cholate, with and without fluorescent labels on the apolipoprotein and DMPC molecules.

Phospholipids (DMPC and NBD-DMPC) were purchased from Avanti Polar Lipids. Inc (Alabaster, Ala.). Full-length apoA-I was purchased from Fitzgerald, Inc. (Concord, Mass.), apoA-I, Δ1-55 (MSP1T2) and Nanodisc™ particles were purchased from Nanodisc, Inc., (Urbana, Ill.). The latter particles were made from DMPC and apoA-I, Δ1-55 protein fragment (MSP1T2); this fragment has a modified $NH_2$-terminus containing a His tag and a tobacco etch virus (TEV) cleavage site.

FIG. 28 schematically shows the assembly process while Table 4 (see Example 23 below) details the NLP preparations undertaken in this example. Individual reactants are combined, mixed and subjected to a series of temperature transitions before overnight incubation. NLPs are separated from the reaction mixture by chromatography, concentrated and characterized.

DMPC (20 mg) is weighed out, added to a glass, round bottom tube followed by chloroform (200 µl) to dissolve lipid. Chloroform is evaporated in a stream of nitrogen with constant rotation to distribute the lipid evenly along the tube wall and placed under vacuum overnight. DMPC is either re-suspended in TBS with probe sonication or with TBS/cholate and gentle vortexing; the final concentration of cholate (20 mM) is above its critical micellar concentration (CMC). Apolipoproteins (200-250 µg) are added to the TBS/DMPC solution+/−cholate at a mass ratio of 4:1 for apoE422K and 3:1 of apoLp-III. The particle formation process is started with 3 repeated sets of transition temperature incubations, above and below the transition temperature of DMPC (23.8° C.), i.e. 10 minutes at 30° C., then 10 minutes at 20° C., with light hand mixing between incubations. After 3 heating and cooling transitions, the samples are incubated at 23.8° C. overnight.

Following assembly, samples containing cholate are dialyzed against 1000× volume of TBS buffer using 3 changes in 24 hrs. The NLPs are purified from 'free protein' and 'free lipid' by size-exclusion chromatography (VP HPLC, Shimadzu) using a SUPERDEX™ 200 HR 10/30 column (GE Healthcare), in TBS at a flow rate of 0.5 ml/min. The column was calibrated with four protein standards of known molecular weight and Stokes diameter that span the separation range of the column and the NLP samples. The void volume was established with Blue dextran. The NLP fractions are concentrated to approximately 0.1 mg/ml using molecular weight sieve filters (Vivascience) with molecular weight cutoffs of 50 kDa. Protein concentration was determined using the ADV01 protein concentration kit (Cytoskeleton, Inc.).

Figure 29:
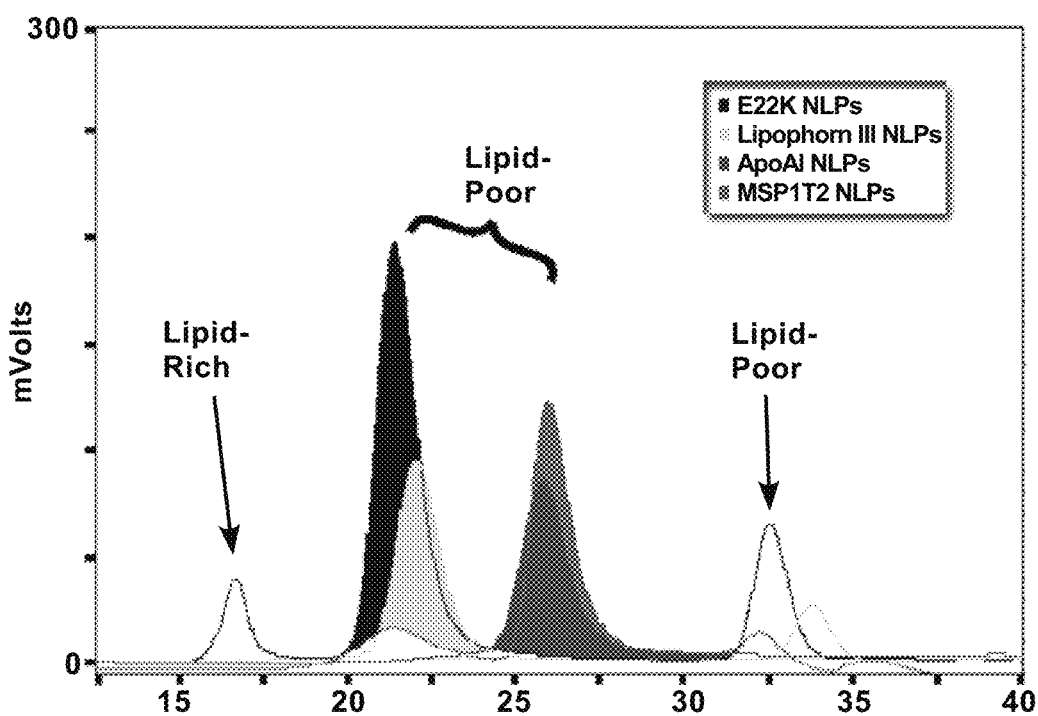
FIG. 29 is a diagram illustrating size exclusion chromatography of a NLPs assembly reaction mixture, according to an embodiment herein disclosed.

Example 18: NLPs Purification from Free Lipid and Free Protein Starting Reactants Comparison of Size Exclusion Chromatography (SEC) traces from NLP assemblies illustrated in FIG. 29 provides insight on particle molecular size and homogeneity. In particular the chromatogram of the ApoE422K-, Lipophorin III-, ApoAI-, and MSP1T2-derived NLPs shows one to three peaks at A280 nm. The NLP peak eluted as the predominant peak in the chromatogram, well separated from lipid-rich and lipid-poor fractions and was isolated for further analysis. The larger E422K and apoLpIII peaks are eluted at about 21 min, while the smaller ApoAI derived NLPs elute at about 26 min. Molecular size information from SEC is shown in Table 4 below.

ApoE422K and apoLp-III derived NLPs eluted a few minutes after the void volume, whereas the two apoA1-based NLPs eluted 3-4 minutes after the others. These data suggest larger particles are formed from apoE422K and lipophorin apolipoproteins versus particles derived from apoA-I proteins. The SEC profiles of apoE422K and lipophorin-NLPs were quite similar eluting in nearly the same position showing a diameter of ~14-15 nm. Each had a small 'free lipid' peak and a larger 'free protein' peak surrounding the single predominant NLP peak; this elution pattern for E422K is similar to previous results (20). Interestingly, altering the lipid:protein ratio for apoLp-III assembled NLPs enhanced the NLP peak, while diminishing the free component peaks consistent with previous, work (21). When cholate was used to solubilize lipid films deposited by chloroform evaporation, the 'free lipid' peak is diminished or completely disappears suggesting that altering lipid:protein ratio affects apparent yield of lipophorin-based NLPs (data not shown).

Example 19: NLPs' Size and Heterogeneities Associated with Individual Apolipoproteins Equal amounts of NLP samples (0.5-2 µg) are diluted with 2× native gel sample buffer (Invitrogen) and loaded onto 4-20% gradient pre-made Tris-HCl gels (Invitrogen). Samples are electrophoresed for 250 Vhrs at a constant 125V. After electrophoresis, gels are incubated with SYPRO® Ruby for 2 hours and then destained using 10% MeOH, 7% Acetic acid. Following a brief wash with ddH$_2$O, gels are imaged using a Typhoon 9410 (GE Healthcare) at 532 nm (green laser) with a 610 nm bandpass 30 filter. Molecular weights are determined by comparing migration vs. log molecular weight of standard proteins found in the NativeMark standard (Invitrogen). The Stokes diameter of the NLPs is calculated from the known Stokes diameter of the same proteins in the standard sample.

Figures 30, 31:
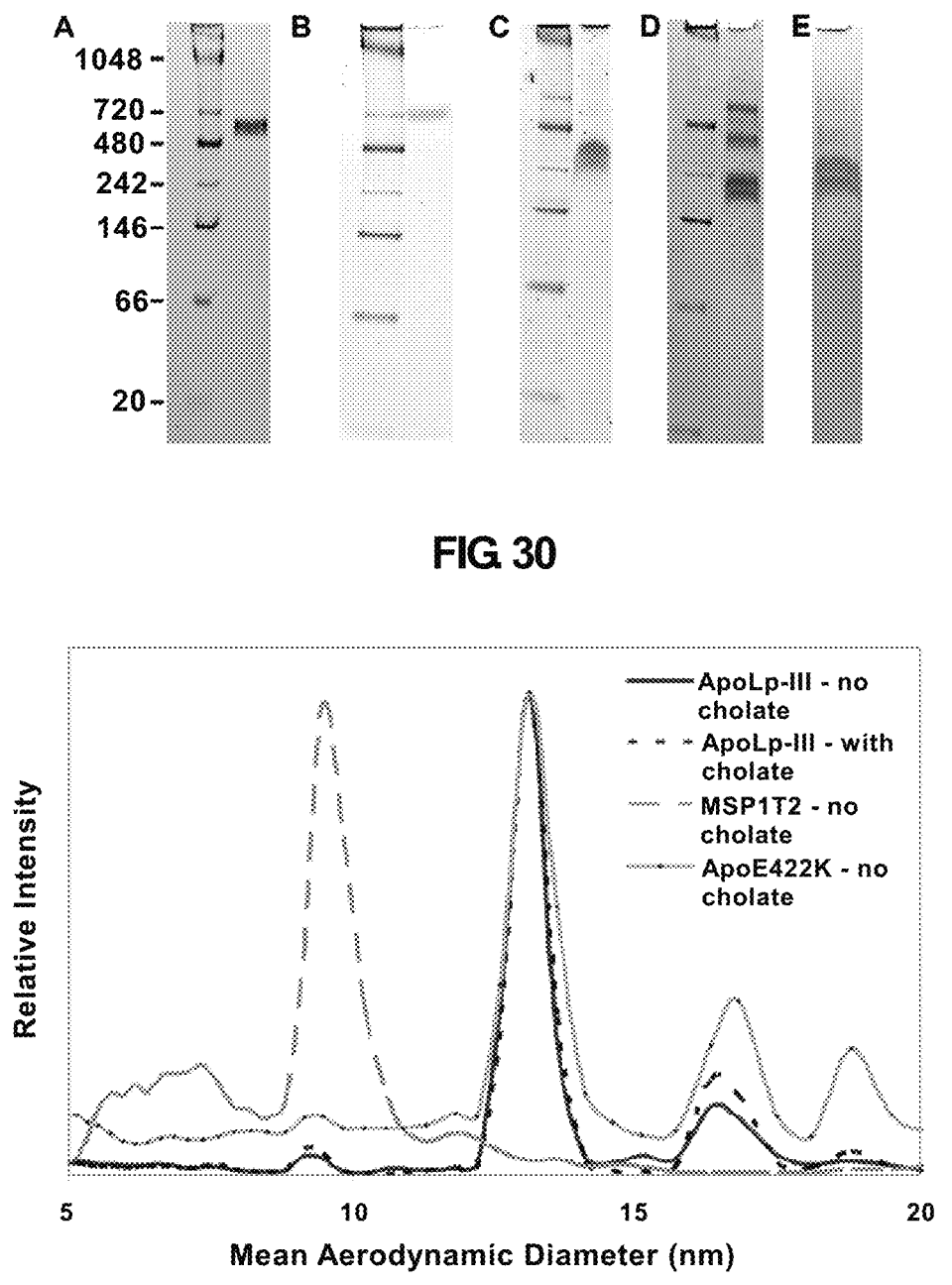

The results illustrated in FIG. 30 show predominant single bands <700 kDa for E422K-NLPs (A) and apoLp-III NLPs (B). The apoAI-derived (Fitzgerald, Inc.) NLPs show five major species when full-length ApoAI (C) or MSP1T2 (D) proteins (Nanodisc, Inc.) are used for making NLPs. Panel E shows the commercially available NLP sample from Nanodisc, Inc. Native gels of NLP fractions obtained from cholate containing preparations were qualitatively similar to those shown here. Each gel was stained with SYPRO® RUBY which has a wider dynamic range than Coomassie stain and is more sensitive; it is possible that, some protein species may not be detected.

Accordingly, native gel electrophoresis reveals (FIG. 30) that apoE422K and apoLp-III NLPs appear predominantly as single bands. On the contrary NLP preparations using apoAI and MSP1T2 (Δ1-55 apoAI) show multiple bands. Five bands on the gel corresponding to putative NLPs were observed using purchased MSP1T2; the three larger molecular weight bands constitute less than 10% of the total protein amount. Overloading apoE422K NLPs on native gels show minor larger molecular weight bands; AFM analysis of the latter show NLP species of larger diameter. These larger species likely do not affect size characterization shown in Table 4. Our MSP1T2-derived NLPs averaged 260 kDa, consistent with the molecular weight obtained from purchased MSP1T2-based 'nanodiscs', of 255 kDa. The Stokes diameter of all NLP assemblies was determined by migration comparison to protein standards with known Stokes diameters and shown in Table 4. The calculated Stokes diameter of the apoAI-derived NLPs was approximately 11 nm, while the apoE422K- and apoLp-III-derived NLPs showed around 13 nm diameters. The apoLpIII-NLPs were slightly larger by native PAGE when compared to apoE422K-NLPs; this observation is not consistent with the SEC data that suggested apoE422K-derived particles were larger. This discrepancy might be due to differences in protein shape, charge and/or bound DMPC molecules. Size of NLPs determined by SEC and native PAGE are based on calibration standards used for soluble proteins. As such, these standards may not be appropriate for calibrating lipid-containing NLPs by native PAGE.

Example 20: NLPs Characterization by Mass Spectrometry and Ion Mobility Spectrometry (IMS)

In addition to using previously reported analytical methods for examining NLP, ion mobility spectrometry (IMS) was also used, a very sensitive and precise technique for measuring particle size Mass determination was performed using Bruker APEX II 9.4 T FTICR mass spectrometer through a homebuilt nanospray interface on an Apollo (Bruker Daltonics, Billerica, Mass., USA) ESI source. Protein solution concentrations were 1-10 µM or 1 nM in 10 mM ammonium acetate, pH 7.5. Solutions were desalted and concentrated by centrifugal filtration using Microcon or Amicon Ultra-4 filters (Millipore, Bedford, Mass.).

The aerodynamic diameter of NLPs was determined with a Macroion Mobility Spectrometer (Model 3890, TSI Inc., Shoreview, Minn.). The details of the instrumentation and a method for measuring protein sizes have been described elsewhere (4,5). Interestingly, this method has been used to measure the size distribution for HDL, LDL and VLDL taken directly from serum (6). Briefly, the instrument consists of an electrospray ionization source with a charge-neutralizing chamber, a differential mobility analyzer (DMA) and a condensation particle counter (CPC). Multiply charged droplets generated by electrospray are charge-reduced by interaction with air ions formed by α-radiation ($^{210}$Po). NLP samples are exchanged via dialysis (3× buffer exchange) into a volatile buffer and then pumped into the electrospray source at 100 nL/min. These conditions were chosen so primary electrospray droplets contain, on average, less than one individual NLP in 25 mM ammonium acetate. The droplets ultimately evaporate, leaving individual NLPs in the gas phase carrying, predominantly, a single charge (7). Charged NLPs pass through a scanning differential mobility analyzer and are counted by a condensation particle counter. The size distribution of a population of NLPs is determined from the scanning parameters; mobility measurements are used to infer NLP mean aerodynamic diameter.

FIG. 31 shows differential ion mobility spectra for four representative NLP preparations. MSP1T2 scaffold without cholate, apoLp-III scaffold with cholate, apoLp-III scaffold without cholate, and apoE422K without cholate. The centroid and full width at half maximum (FWHM) of the highest abundance peak within a trace is used to represent the average mean aerodynamic diameter of the particles within a sample. The lower abundance peaks at ~17 and 19 nm in the apoLp-III and ApoE422K traces are respectively likely due to slightly larger particles of lower abundance that are not detected by native gel. The MSP1T2-NLPs appear significantly smaller than the apoLp-III and apoE422K-NLPs while the addition of cholate during formation of NLPs utilizing apoLp-III as the scaffold has no significant effect on the ion mobility trace and the average mean aerodynamic particle diameter. Ion mobility traces of mean aerodynamic diameter size distributions for the other NLP preparations shown in Table 4 were qualitatively and quantitatively similar to those shown here.

Together with the ion mobility data summarized in Table 4 below, the spectra illustrated in FIG. 31 indicate that IMS can resolve size differences in NLP arising from the use of differing apolipoproteins. Moreover, these spectra also illustrate that, for a given apolipoprotein, cholate addition and removal does not alter particle size. The full-width half maximum of the predominant peak in each spectrum is similar suggesting that, at least for the predominant IMS peak, NLP size heterogeneity may not be strongly dependent on choice of scaffold protein. Heterogeneity observed in the native gel electrophoresis data for apoA1 and MSP1T2 preparations is not reflected in the ion mobility FWHM data. This likely arises as different bands on a gel correspond to different peak diameters within an IMS spectrum and consequently, the IMS FWHM data are only assessing the heterogeneity within a single gel band.

Example 21: NLPs Characterization by Transmission Electron Microscopy (TMS) and Atomic Force Microscopy (AFM)

Samples were diluted using TBS to achieve a final concentration of 0.02 mg/ml. Three μl of each sample was pipetted onto a carbon coated 400 mesh copper EM grid (Ted Pella). After sitting for 1 minute, the sample was blotted with Whatman filter paper. Three μl of 2% Uranyl Acetate (Electron Microscopy Sciences) was applied for one minute and then blotted. Grids were dried for 30 minutes before use in the EM. Negative stain images were recorded using a Philips CM300 FEG transmission electron microscope operating at an accelerating voltage of 300 keV. Images were recorded as 8-bit and 16-bit tiff at varying magnifications onto a Gatan digital CCD and stored as jpegs and Gatan image format files. Images were then analyzed using Gatan Digital Micrograph software.

Figure 32:
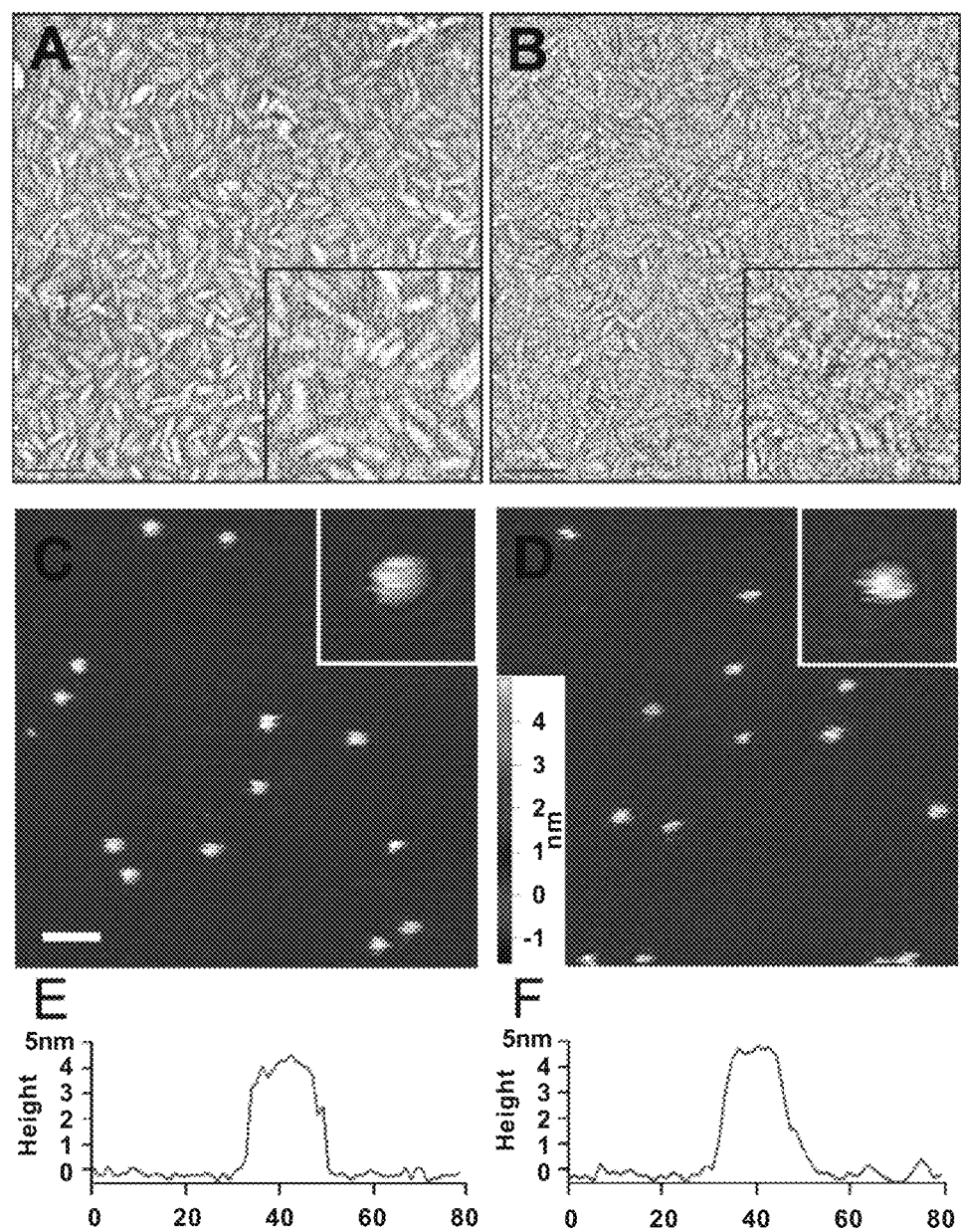
FIG. 32 shows a negative stain TEM and AFM of apoE422K-NLP preparations with (panel B, D and F) and without cholate (Panel A, C and E) according to an embodiment herein disclosed. The scale bar in each panel is 50 nm; insets are a higher magnification.

Micrographs in FIG. 32 show NLPs whose dimensions are consistent with previously described observations (see Table 4 below). In particular, the micrographs of FIG. 32 show a negative stain TEM and AFM of apoE422K-NLP preparations with and without cholate. For TEM, each sample was stained with a 2% solution of uranyl acetate, as described herein. Samples for AFM were measured in solution, using non-contact mode. Both electron micrographs were taken at 65,000× magnification, panel B shows sample prepared with cholate. Panels C and D show 400×400 nm topographical AFM images of apo4E22K-NLPs having similar shape and height; they were prepared without cholate (C) or with cholate (D). The scale bar represents 50 nm. A color bar scale identifies NLP height and insets show zoomed in regions (50×50 nm), showing single particles. A section line trace below each image show both the typical heights and diameters in the slow scan direction for the respective AFM images, Panel E (no cholate) and F (cholate). The average height for NLPs with cholate is 4.8 nm+/−0.2 nm and the heights of NLPs without cholate 4.8 nm+/−0.3 nm, which is consistent with the theoretical size of the lipid bilayer. The data suggest discoidal structures with a diameter of about 10-20 nm and height consistent with the thickness of a bilayer.

Two of these assemblies made from apoE422K and DMPC are shown, with (panel B) and without cholate (panel A). The lower right-hand corner of each panel shows a region at higher magnification to highlight the presence of discoidal structures. Cholate has no effect on the size and structure of apoE422K-derived NLPs. Like previous reports, images of stacked particles were observed—described as "rouleaux"—but not in all samples. Others have described these formations as artifacts of sample preparation and concentration (22).

Atomically flat Muscovite mica disks were glued to metal substrates to secure them to the scanner of a stand-alone MFP-3D AFM (Asylum Research, Santa Barbara, Calif.). 2 uL of solution was incubated for two minutes on the mica surface in imaging buffer (10 mM MgCl2, 10 mM Tris-HCL, and 0.1 M NaCl, adjusted to pH 8.0) and then lightly rinsed. The AFM has a closed loop in the x, y, and z axes. The topographical images were obtained with "Biolevers" (Olympus, Tokyo, Japan) with a spring constant of 0.03 N/m. Images were taken in alternate contact (AC) mode in liquid, with amplitudes below 20 nm and an amplitude setpoint at 50% tapping amplitude. Scan rates were below 1.5 Hz. Height, amplitude, and phase images were recorded. Heights of features in images were determined by histogram analysis of contiguous particles. Experiments were carried out in a temperature controlled room at 23+/−1° C.

All four apolipoprotein assemblies show a common discoidal bilayer structure. In particular, it was observed that NLPs made from different apolipoproteins examined by AFM showed discrete bracketed structures even at high concentration, indicative of individual particles. When DMPC without apolipoprotein is examined, planar fusible features, ~4-5 nm in thickness are observed consistent with the presence of a lipid bilayer (data not shown). Also, when apolipoprotein is examined alone, globular features on the order of 2-3 nm are seen. NLPs have diameters ranging from 10 to 20 nm and heights of approximately 5 nm; these observations are consistent with diameters measured by other techniques described above. Particle size and structure is unaffected by cholate as shown in FIG. 32 with apoE422K-derived NLPs. These AFM data indicate that the particles are just less than 5 nm high with diameters of ~20 nm. This diameter size is larger than was derived from TEM, but AFM is known to increase the size of x, y resolution due to tip convolution effects. Combined, AFM and TEM data suggests discoidal structures with height dimensions consistent with a phospholipid bilayer and a diameter of about 10-20 nm; cholate addition during assembly does not appreciably change the heights of the apoE422K and apoLp-III assemblies (see Table 4).

Example 22: Monitoring NLPs Assembly Process by Fluorescent Labeling

FIG. 29 shows analyses of a labeled NLP using a Cy3-labeled apoE422K mixed with 7-nitrobenz-2-oxa-1,3-diazol-4-yl labeled DMPC (DMPC-NBD).

lipoprotein used, show remarkable consistency in measuring overall NLP size and shape for any given apolipoprotein. Moreover, measured sizes and shapes did not differ appreciably when formed in the presence of cholate and when using fluorophore labeled reactants. The following sections summarize results from each of the specific characterization techniques.

TABLE 4

| Apolipoprotein | Lipid | Cholate | Native Gel Mol. Wt. (kDa) | Native Gel Stokes D (nm) | SEC Mol. Wt. (kDa) | SEC Stokes D (nm) | Ion Mobility AMAD ± FWHM | AFM (nm) Height | TEM (nm) Diameter |
|---|---|---|---|---|---|---|---|---|---|
| Nanodiscs (MSP1T2) | 100% DMPC | No | 290 ± 10 | 10.8 ± 0.1 | 190 ± 15 | 9.3 ± 0.3 | 10.6 ± 1.4 | 5.1 ± 0.2 | 10.2 ± 3.1 |
| apoAI | 100% DMPC | No | 360 ± 10 | 11.4 ± 0.1 | 270 ± 30 | 12.6 ± 0.4 | 10.5 ± 1.1 | 4.3 ± 0.5 | 13.0 ± 1.4 |
| MSP1T2 (ΔapoAI) | 100% DMPC | No | 260 ± 30 | 10.1 ± 0.8 | 300 ± 120 | 12.8 ± 1.4 | 9.5 ± 0.9 | 4.8 ± 0.2 | 12.7 ± 3.0 |
| apoE422K | 100% DMPC | No | 605 ± 60 | 12.6 ± 0.3 | 560 ± 15 | 15.1 ± 0.1 | 13.2 ± 0.9 | 4.9 ± 0.2 | 17.6 ± 2.7 |
| apoLp-III | 100% DMPC | No | 620 ± 60 | 12.8 ± 0.4 | 480 ± 25 | 14.5 ± 0.2 | 13.1 ± 0.7 | 4.4 ± 0.3 | 17.6 ± 2.6 |
| apoE422K | 100% DMPC | Yes | 660 ± 40 | 13.2 ± 0.1 | 600 ± 15 | 15.3 ± 0.1 | 13.6 ± 1.0 | 4.9 ± 0.3 | 16.2 ± 2.4 |
| apoLp-III | 100% DMPC | Yes | 530 ± 10 | 12.6 ± 0.1 | 425 ± 12 | 14.1 ± 0.5 | 13.1 ± 0.7 | 4.0 ± 0.4 | 18.0 ± 2.6 |
| Cy3-apoE422K | 100% DMPC | Yes & No | 510 ± 40 | 12.4 ± 0.4 | 660 ± 10 | 15.1 ± 0.1 | 14.0 ± 1.5 | 4.6 ± 0.3 | 20.8 ± 2.9 |
| Cy3-apoE422K | 100% DMPC (1% NBD) | Yes & No | 630 ± 70 | 13.0 ± 0.2 | 670 ± 15 | 15.1 ± 0.1 | 14.1 ± 1.5 | 5.1 ± 0.3 | 17.4 ± 2.7 |

Figure 33:
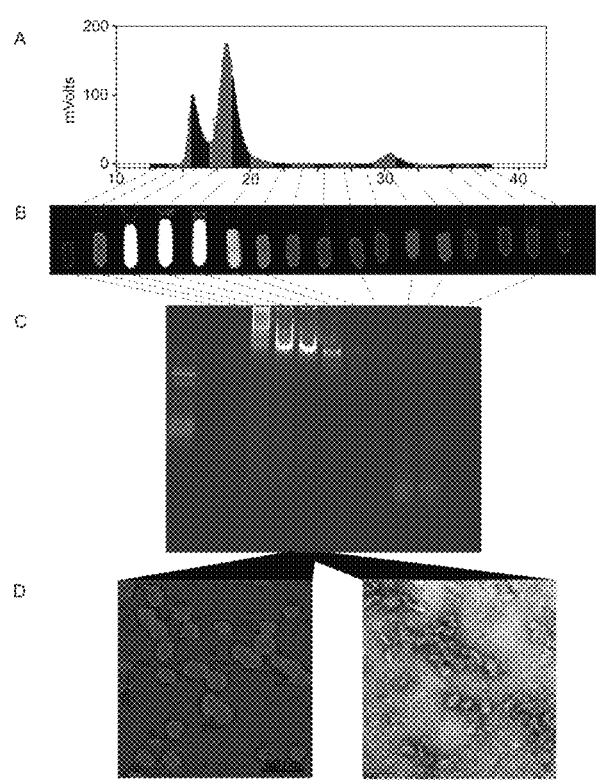
FIG. 33 illustrates characterization of fluorescently-labeled NLPs showing similar structure and in comparison with unlabeled NLPs, according to an embodiment herein disclosed. Cy3-labeled apoE422K (50%) and DMPC containing 1% NBD-DMPC were used to form labeled NLPs. Panel A shows the SEC fractionation of labeled NLPs. Early eluting peaks correspond to large DMPC vesicles and NLP fractions, later eluting peak contains unreacted apoE422K. Panel B shows a fluorescent scan of SEC fractions: that contain NBD-DMPC (green), Cy3-apoE422K (red), and fluorescent NLPs (yellow). Panel C shows the native PAGE of SEC fractions highlighting the migration and homogeneity of the NLP peak. Panel D shows a topographical AFM image (left) and TEM image (right) of the main NLP fraction vial, highlighting the homogeneity, size, and structure of the fluorescent NLPs

In the analysis illustrated in FIG. 33 fractions collected from SEC were characterized by native PAGE (panel C), AFM (panel D, right) and TEM (panel D, left). Importantly, it appears that labeled NLP reactants do not affect NLP formation. The SEC trace (panel A) shows similar lipid-rich, NLP, and lipid-poor peaks that co-elute with those species in non-fluorescent samples. The SEC fractions were analyzed for fluorescence (panel B) and the fluorescent lipid (green pseudo color), fluorescent protein (red pseudo color), and NLPs (yellow pseudo color) show up in the expected vials based on the SEC trace. The results illustrated in FIG. 33 indicate that fluorescently-labeled NLPs show similar structure and size compared to unlabeled NLPs.

Table 4 shows the size characteristics of NLPs made using fluorescently-labeled reactants do not appreciably change from the unlabeled reactants. Moreover, the size and shape are maintained as observed AFM and EM analyses show similar discoidal structures (panel D). These data suggest that fluorescent dye attachment to lipid and protein reagents can be used to track NLP assembly as well as provide means to detect individual reactants within the particle.

Example 23: NLPs Combined Characterization

Table 4 summarizes results from combined characterization approaches and highlights particle size parameters of NLPs assembled from each of four apolipoproteins in combination with a single phospholipid, dimyristoylphosphatidylcholine (DMPC). Reaction of each protein with DMPC yields NLPs with unique overall structural/shape characteristics. In general, particles produced were found to be discoidal in shape with diameters ranging from 10-20 nm dependent on the apolipoprotein or derivative used in assembly; a height of ~5 nm was determined for all NLP preparations, consistent with a membrane bilayer formed by DMPC (23).

The fundamental observations are that the apolipoprotein is the primary determinant of NLP size and that a discoidal shape was consistent among the four assemblies. These characterization results, irrespective of the method or apolipoprotein used, show remarkable consistency in measuring overall NLP size and shape for any given apolipoprotein. Moreover, measured sizes and shapes did not differ appreciably when formed in the presence of cholate and when using fluorophore labeled reactants. The following sections summarize results from each of the specific characterization techniques.

Table 4 illustrates the results of the physical characterization of NLPs by native gel electrophoresis, SEC, Ion mobility spectrometry, AFM and negative stain TEM performed according to Examples 1 to 7. Molecular weights and Stokes diameters of the NLPs from native gels and SEC were determined using known protein standards and are shown in kDa and nm, respectively. The average mean aerodynamic diameter (AMAD) corresponds to the centroid and full width at half maximum (FWHM) of the most abundance peak within an ion mobility trace. The centroid provides a robust measurement of the average mean aerodynamic diameter of the particles within a sample while the FWHM provides a comparative estimate of sample heterogeneity. AFM derived measurements of height and TEM derived measurements of diameter are reported as the mean+/−standard deviation of individual measurements from typically 100 NLPs within a sample. ApoAI and MSP1T2 assembled NLPs were noticeably smaller than E422K and apoLp-III assembled NLPs, ranging in size from 10-13 nm in diameter as compared to 12-20 nm in diameter for the E and apoLp-III assemblies. Cholate addition during assembly did not appear to appreciably change the size of any of the structures. The addition of fluorescently labeled assembly components also had little effect on the molecular size, but likely affects the homogeneity of the assembled structures since fluorescent components were unlikely to be uniformly distributed throughout the NLP population. Characterization data using purchased empty Nanodiscs™ are also shown for comparative purposes.

Example 24: NLPs Production and Characterization to Support NLPs Modeling and Molecular Dynamics NLPs were produced, purified and characterized as described in Examples 16 to 21. In particular, the NLPs did include Phospholipids 1,2-Dimyristoyl-sn-Glycero-3-Phosphocholine (DMPC) and 1,2-Dioleoyl-sn-Glycero-3-Phosphocholine (DOPC) and apolipoprotein apoE422k The DMPC and DOPC were purchased from Avanti Polar Lipids, Inc. (Alabaster, Ala.). Full-length apoA-I was purchased from Fitzgerald, Inc. (Concord, Mass.), Nanodisc™ particles were purchased from Nanodisc, Inc., (Urbana, Ill.). An expression clone to produce apoE422k, the N-terminal 22 kDa fragment of apolipoprotein E4 (apoE4), as a 6His and thyrodoxin tagged construct was also used.

ApoE422k was chosen based on its importance for biotechnology applications, specifically the solubilization of membrane proteins. It is easy to purify to homogeneity and is known to be more stable than full length apoE4 or apoE3. NLP formation with E422k is highly reproducible and NLPs are stable over extended time periods. Furthermore, it produces larger particles compared to A-I or MSP1 (14), which may be relevant when accommodating larger membrane proteins Briefly, dried DMPC was dissolved in 10 mM Tris pH 7.4, 0.15 M sodium chloride, 0.25 mM EDTA, 0.005% sodium azide (TBS) buffer at a concentration of 20 mg/ml followed by probe sonication to clarity. This resulting liposome suspension was spun at 13000 g for 2.5 minutes to remove any residual titanium from the probe sonicator and unsolubilized lipid. ApoE422k (200-250 µg) was added to the TBS/DMPC solution at a mass ratio of 4:1. The particle formation process was started with 3 repeated sets of transition temperature incubations, above (10 minutes at 30° C.) and below the transition temperature of DMPC (23.8° C.) followed by incubation at 23.8° C. overnight. The NLPs were purified by size-exclusion chromatography using a SUPERDEX™ 200 HR 10/300 column (GE Healthcare), in TBS at a flow rate of 0.5 ml/min.

The NLP fractions were concentrated to approximately 0.1 mg/ml using molecular weight sieve filters (Vivascience) with molecular weight cutoffs of 50 kDa. Protein concentration was determined using the ADV01 protein concentration kit (Cytoskeleton, Inc.).

The samples were analyzed by Atomic Force Microscopy. In particular, Atomically flat Muscovite mica disks were glued to metal substrates to secure them to the scanner of a stand-alone MFP-3D AFM (Asylum Research, Santa Barbara, Calif.). Two µL of solution at 1.0 µg/mL concentration was incubated for two minutes on the mica surface in imaging buffer (10 mM $MgCl_2$, 10 mM Tris-HCl, and 0.1 M NaCl, adjusted to pH 8.0) then lightly rinsed. The AFM has a closed loop in the x, y, and z axes. Topographical images were obtained with silicon nitride cantilever probes (MSCT, Veeco, Santa Barbara, Calif.) with a spring constant of 0.05 N/m.

Images were taken in alternate contact (AC) mode in liquid, with amplitudes below 20 nm and an amplitude setpoint at 50% tapping amplitude. Scan rates were below 1.5 Hz. Height, amplitude, and phase images were recorded. Diameters of particles in images were determined by the full width half maximum (FWHM) analysis of contiguous particles in the slow scan direction, using IgorPro Wavemetrics software routines. Heights of particles were determined from histogram analysis. Experiments were carried out in a temperature controlled room at 23+/−1° C.

Alternate contact mode or tapping mode was used in AFM imaging to ensure minimal structural perturbation from tip-sample contact force. It is widely known that imaging nano-scale particles with AFM results in laterally broadening particle size due to tip convolution effects, but there exists a second broadening effect due to the finite response of imaging feedback in the fast scan direction. This latter effect can result in the NLPs shape appearing elongated in the fast scan direction. To limit tip convolution effects, only tips revealing sharp imaging were used for analysis. To limit the broadening from slow imaging response, FWHM from a cross-section perpendicular to the fast scan direction was used to determine particle diameter. To determine the reproducibility of the procedure for measuring NLP diameters, randomly selected particles were repeatedly imaged to verify consistent diameter measurements.

The NLPs were then subjected to Ion Mobility Spectrometry. IMS determines the mean aerodynamic diameter of particles based on the terms in equation (1):

$$Dp = nqE/3\pi Nv \qquad \text{Eq (1)}$$

where Dp=particle diameter, n=number of elementary electrical charges, q=unit charge in Coulombs, E=electrical field strength, N=viscosity of suspending gas and v=particle velocity. This is a first principles measurement and it does not require calibration for measuring particle diameter. The development of an electrospray interface provides a way to analyze particles suspended in a liquid.

An electrospray interface was used (Model 3480, TSI, Inc. Shoreview, Minn. and a Macroion Mobility Spectrometer Model 3890, TSI Inc., Shoreview, Minn.) to measure the size distribution of NLP particles after they were exchanged via dialysis into a 25 mM ammonium acetate buffer (14, 26, 27). The methodology used to prepare the samples and measure the NLP size distributions were similar to a method developed by Benner for analyzing human lipoprotein particles and NLPs.

NLP aerodynamic diameters were subsequently converted to aerodynamic spherical volumes. Assuming volume equivalency of the aerodynamic spherical volumes and NLP discoidal volumes and using an appropriate correction factor, IMS derived mean aerodynamic diameters were converted to NLP discoidal diameters through; where $d_{NLP}$ is the NLP discoidal diameter, h is the NLP discoidal height determined $$d_{NLP} = 2\sqrt{\frac{4(K R_{ma})^3}{3 h}} \qquad \text{Eq (2)}$$

through AFM analysis, $R_{ma}$ is the mean spherical radius determined from IMS and K is an appropriate correction factor. It is appropriate to convert aerodynamic spherical diameter to discoidal diameters with this factor because the net velocity of the particles during analysis is slow (~5 cm/s) compared to their diffusional velocity (440 cm/s) and thus their shape will be slightly distorted during differential mobility analysis.

Transmission Electron Microscopy (TEM) was also performed. In particular, NLP samples were diluted using TBS, mounted onto carbon coated 400 mesh copper EM grids, stained with 2% Uranyl Acetate and imaged using a Philips CM300 FEG transmission electron microscope operating at an accelerating voltage of 300 keV as previously described (14).

The samples were also analyzed by native PAGE. In particular, equal amounts of NLP samples (0.5-2 µg) were diluted with 2× native gel sample buffer (Invitrogen) and loaded onto 4-20% gradient pre-made Tris-glycine gels (Invitrogen). Samples were electrophoresed for 250 Vhrs (BioRad) at a constant 125V. After electrophoresis, gels were incubated with SYPRO® Ruby for 2 hours and then destained using 10% MeOH, 7% aqueous acetic acid. Following a brief wash with dd$H_2O$, gels were imaged using a Typhoon 9410 (GE Healthcare) at 532 nm (green laser) with a 610 nm bandpass 30 filter. Molecular weights were determined by comparing migration vs. log molecular weight of standard proteins found in the NativeMark standard (Invitrogen).

Example 25: NLPs Modeling and Molecular Dynamics

Figure 34:
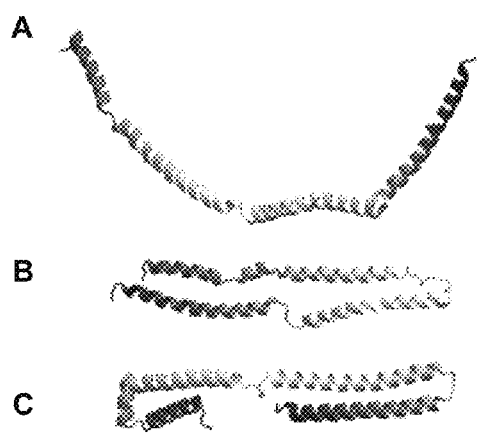
FIG. 34 shows a schematic illustration of refolded apoE422K proteins generated in three different forms according to an embodiment herein disclosed. Panel A. shows a fully extended form. Panel B shows a doubled-back/"hairpin". and Panel C shows semi-extended/"double-hairpin" folds.

NLP Modeling and Molecular Dynamics was then performed on NLPs characterized as described in Example 24: An idealized 35 nm$_2$ bilayer slab of DMPC lipids (a 740,000 atom system) was created and equilibrated to give a lipid cross-sectional area of 52 Å$_2$ per lipid. Circular discs were cut out of this slab at 0.5 nm diameter increments, in a range of 11 to 30 nm. The apoE422k crystal structure, PDB:1GS9 was used as the basis for the protein modeling. Refolded E422k proteins were modeled and tested in three different forms: fully extended, doubled-back/"hairpin", and semi-extended/"double-hairpin" folds (FIG. 34).

Initial modeling of the NLPs was based on a fully extended E422k (FIG. 34A) assuming E422k NLPs would be similar to the "double belt" model reported for A-I NLPs (29-32) and previously suggested for E322K NLPs. This gave rise to a fold for E422k, with full hydrophobic association for the lipid, that is fully extended—as previously suggested for this portion of E4(10). However, at least two other folds are possible for E422k consistent with water exclusion of the hydrophobic acyl chains. The soluble folded-E422k contains three hairpin turns linking four helices. Forming a hairpin in the extended fold so that the E4 doubles back on itself creates a model with a self-contained double-belt (FIG. 34B). This so-called "hairpin" model for lipoproteins has been previously suggested. For this fold to form, the loop between helices 2 and 3 of folded E422k would have to undergo a 180° rotation. A more energetically favorable rearrangement of E422k would involve only the opening of the 2-3 loop to produce a semi-extended "double-hairpin" model—that is, one containing two of the bends from the folded-E422k and involving a simple opening of the hydrophobic core of the folded-E422k to pack against the hydrophobic face of the lipid (FIG. 34C).

Proteins were aligned along the equator of the lipid disc and packed against the lipid discs of different sizes with the aim of fully enclosing the hydrophobic face of the lipids but not allowing the proteins to overlap each other. A 1 nanosecond (ns) equilibration molecular dynamics (MD) run was then used to optimize the packing of the lipid against the protein. NLPs without gaps between lipid and protein, were then entered into a 40 ns MD simulation to determine the stability of the model. All MD simulations were run using the CHARMM forcefield in NAMD with many of the settings and set-up details taken from previous simulations. Simulations were conducted on 1024 processors of Thunder, a 23 teraflop, 4096 Intel Itanium2 processor machine at the Livermore Computing Center. System set-up, analysis and image preparation was done using, Gromacs (40), Pymol and VMD with additional "in house" tcl/tk, perl and C++ scripts.

Figure 35:
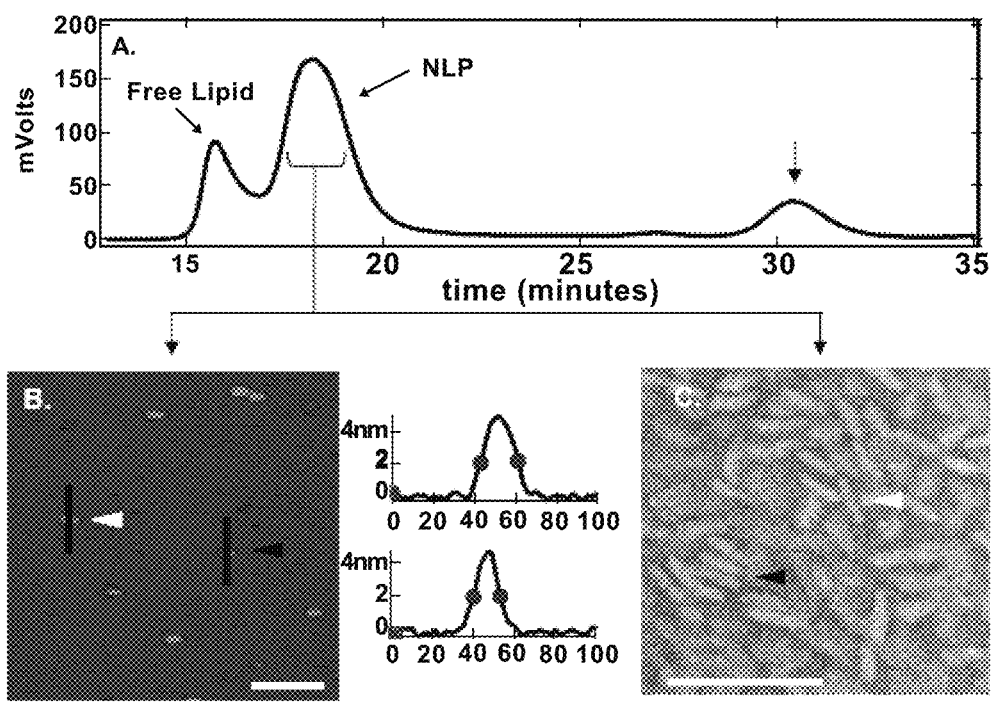
FIG. 35 shows a method of purification and characterization of self-assembled NLPs according to an embodiment herein disclosed. Panel A shows the size exclusion chromatography (SEC) trace of apoE422K/DMPC NLPs. Panels B and C show AFM (Panel B) and TEM (Panel C) images of apoE422K/DMPC NLPs after formation and purification. Cross-sectional analysis of AFM images (black and blue line in image corresponds to black and blue cross-sectional traces shown to the left, respectively) was used to measure NLP height and diameter. The red circles in the traces correspond to the FWHM points used to determine particle diameter. Arrow heads in the AFM and TEM images (C and D) point to NLPs of differing diameter indicating size heterogeneity (black arrow head points to smaller NLPs and white arrow head larger NLPs). AFM scale bar 100 nm, TEM scale bar 50 nm.

Example 26: Verification of NLPs Modeling and Molecular Dynamics Through Individual Particle Characterization E422k/DMPC NLPs were formed using DMPC as the lipid component and E422k as the lipoprotein component as herein described. A typical SEC trace of an E422k/DMPC NLP assembly contains three dominant peaks, the free lipid rich peak, an NLP rich peak, and apolipoprotein rich peak (FIG. 35). NLP rich fractions collected from SEC were pooled and then used for further characterization by atomic force microscopy (AFM) and transmission electron microscopy (TEM) (FIGS. 35B and 35C).

Both single particle characterization techniques showed the production of 12-30 nm sized NLPs (FIGS. 35B and 35C). The AFM image in FIG. 35B illustrates the broadening effect in the fast scan direction, described in the methods section, which can be observed due to the finite response of imaging feedback in this direction. From the TEM images and AFM cross-sectional analysis shown in FIGS. 35B and 35C it is quite apparent that E422k/DMPC NLPs exhibit particle size heterogeneity (FIGS. 35B and 35C).

Figure 36:
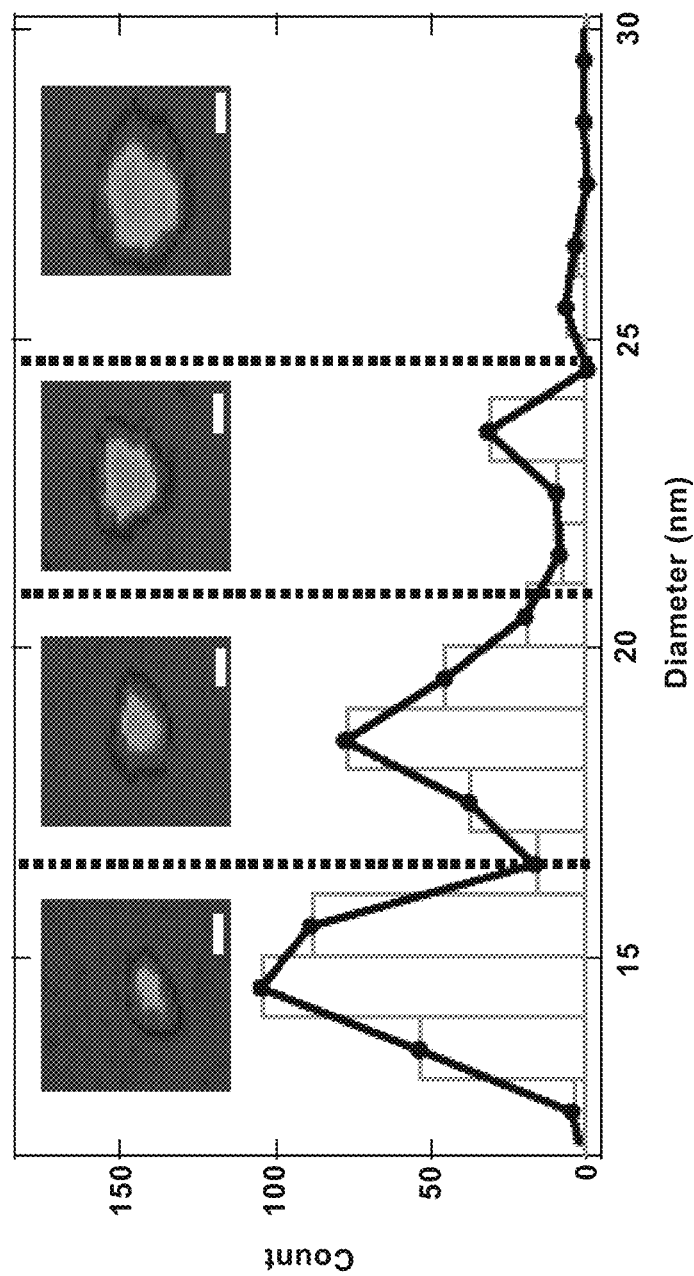
FIG. 36 shows the NLP diameter distribution for 1000 NLPs with a bin width of 1.0 nm according to an embodiment herein disclosed. The inset shows the AFM image of the four different sized NLPs. The scale bar is 10 nm.

Heterogeneous E422k/DMPC NLP diameter distributions display discrete sizes as determined through AFM, TEM and IMS. AFM cross-sectional analysis of several hundred single NLPs was used to quantify both height and diameter heterogeneity. The height distribution of the particles revealed a relatively homogeneous population displaying a Gaussian distribution with a mean height of 4.9+/−0.2 nm, consistent with the height of a lipid bilayer. However, histograms of the diameters revealed that the NLP sizes displayed discrete diameters (FIG. 36). In particular, the results illustrated in FIG. 8 indicate NLPs contain at least 4 distinct populations with diameter sizes of 14.7, 18.8, 23.3 and 28.7 nm (see Table 4 for mean, standard deviation and percentage of each size).

The discrete diameters were centered at 14.7, 18.8, 23.3 and 28.7 nm and the fraction of each NLP type decreased with increasing NLP diameters shown in Table 5, where the diameter mean and SD and percentage of the four NLP populations is reported.

TABLE 5

|  | NLP type 1 | NLP type 2 | NLP type 3 | NLP type 4 |
|---|---|---|---|---|
| diameter (nm) | 14.7 +/− 0.9 | 18.8 +/− 1.0 | 23.3 +/− 1.1 | 28.7 +/− 1.5 |
| Fraction | 0.56 | 0.33 | 0.10 | 0.02 |

Figure 37:
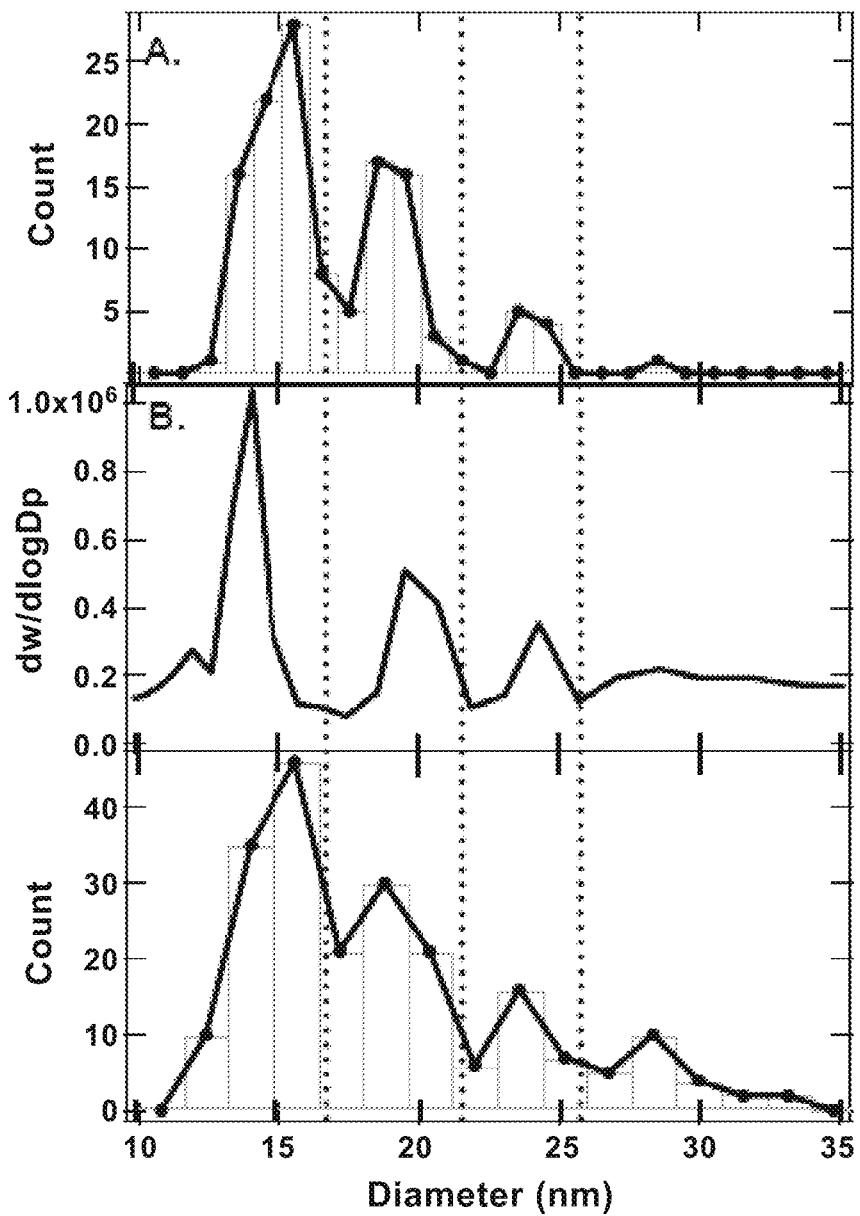
FIG. 37 shows a diagram illustrating the comparison of diameter distributions according to an embodiment herein disclosed, wherein the diameter is measured by AFM, IMS and TEM. A. NLP diameters determined through AFM binned at 1 nm. B. NLP diameters determined through IMS. C. NLP diameters determined through TEM binned at 1.6 nm

To verify that the observed discrete diameters were not an effect of AFM tip resolution or mica surface-particle interactions E422k/DMPC NLPs were also analyzed by ion mobility spectrometry (IMS) and TEM (FIG. 37).

IMS is a technique that determines the mean aerodynamic diameter of particles based upon the differential migration of gas phase ions through a homogeneous electric field and is well established in the field of aerosol science for particle analysis and measurement. The history of the development of IMS was recently extensively reviewed (42). In fact, IMS has been used to determine size distributions for HDLs, LDLs and VLDLs (26, 27) and more recently for NLPs assembled from a wide range of lipoproteins (14). The IMS traces confirm the discrete NLP diameters seen with AFM; in fact the diameter peaks in both the AFM (14.9, 18.7, 23.3, 28.7 nm) and IMS (14.1, 19.5, 24.3, 28.6 nm) are almost identical.

Figure 38:
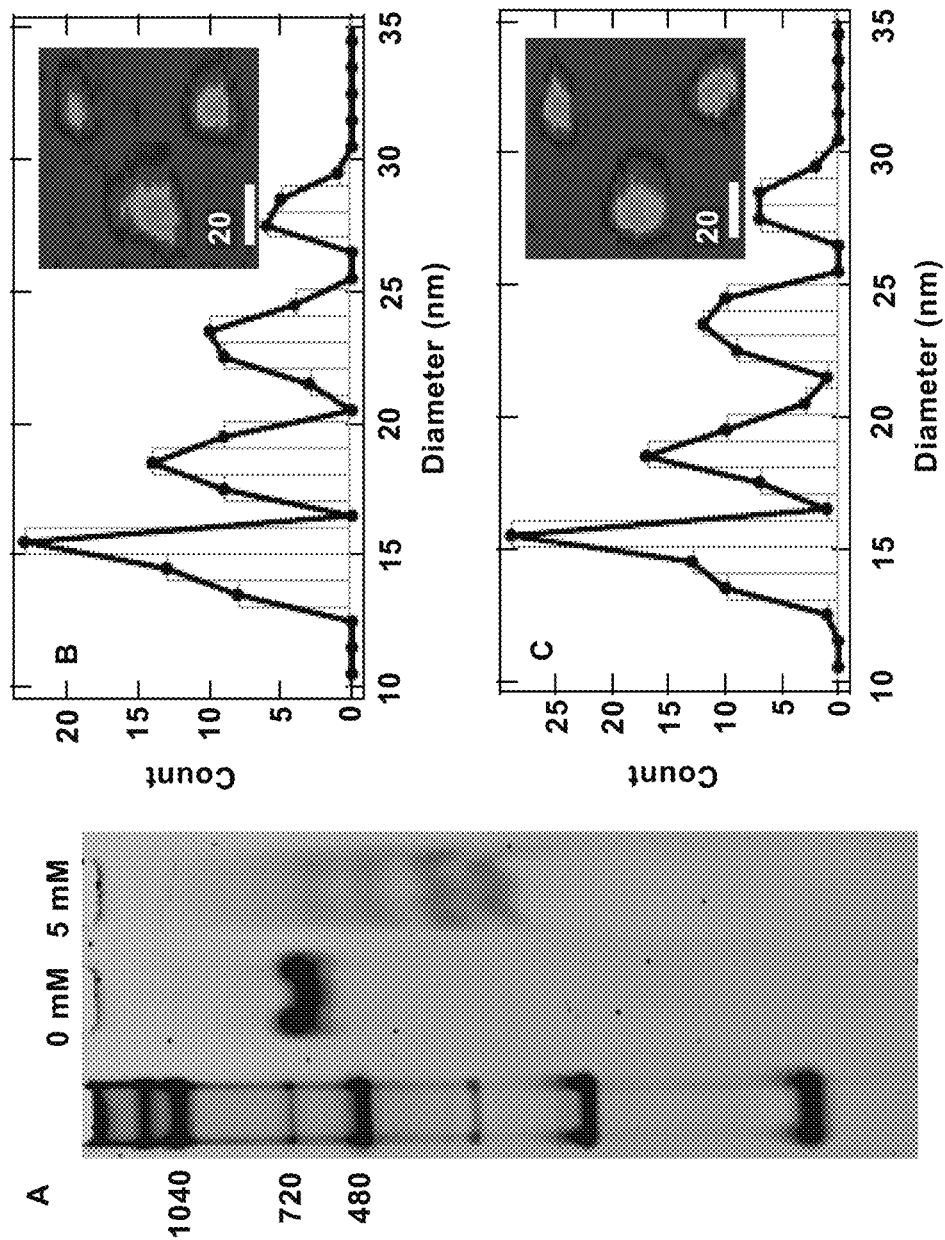
FIG. 38 shows the effect of cholate on NLP separation by native gel electrophoresis according to an embodiment herein disclosed. Panel A shows a native gel electrophoresis of NLPs after SEC purification in the presence of 0 mM cholate (lane 2) displayed a single band but in the presence of 5 mM cholate (lane 3) four dominant bands were observed. Panel B shows the diameter distributions of NLPs in A. at 0 mM cholate. Panel C shows the diameter distributions of NLPs in A. at 5 mM cholate. All histograms were binned at 1.0 nm and AFM images were stitched together to show the predominant NLP sizes.

TEM also confirmed the existence of the same four discrete sizes that were observed by AFM and IMS (14.9 nm, 18.9 nm, 23.3 nm, 29.0 nm) (FIG. 38C). The heterogeneous 10 discrete diameters observed in IMS, AFM and TEM indicate that these sizes are not due to an AFM tip convolution affect but rather represent the real diameter distribution. Interestingly each peak is separated by rather larger set sizes of ~4-5 nm in diameter, which suggests at least three possibilities; a change in tertiary structure of the surrounding lipoprotein E422k, variation in the number of E422k lipoproteins per particle or a combination of these two effects.

E422k/DMPC NLPs were subjected to native gel electrophoresis to further assess particle heterogeneity. 0 mM and 5 mM cholate (below critical micelle concentration of ~15 mM) was added to the NLP solution after assembly and run on native gel (FIG. 5A). The addition of no cholate resulted in a single band at ~603 kDa despite observing multiple sizes by AFM, IMS and TEM (FIG. 38A). In the presence of 5 mM cholate native gel analysis revealed four bands at 234 kDa, 312 kDa, 458 kDa and 615 kDa. To determine if the addition of cholate resulted in the disassembly of NLPs or altered NLP size distribution the sample was imaged by AFM both before (FIG. 38B) and after (FIG. 38C) cholate addition and no significant changes were observed in both NLP height and diameter distributions.

All three techniques (AFM TEM and IMS) independently identified the existence of four distinct particle sizes of E422k/DMPC NLPs with diameters centered at ~14.5, 19, 23.5 and 28 nm.

Figure 39:
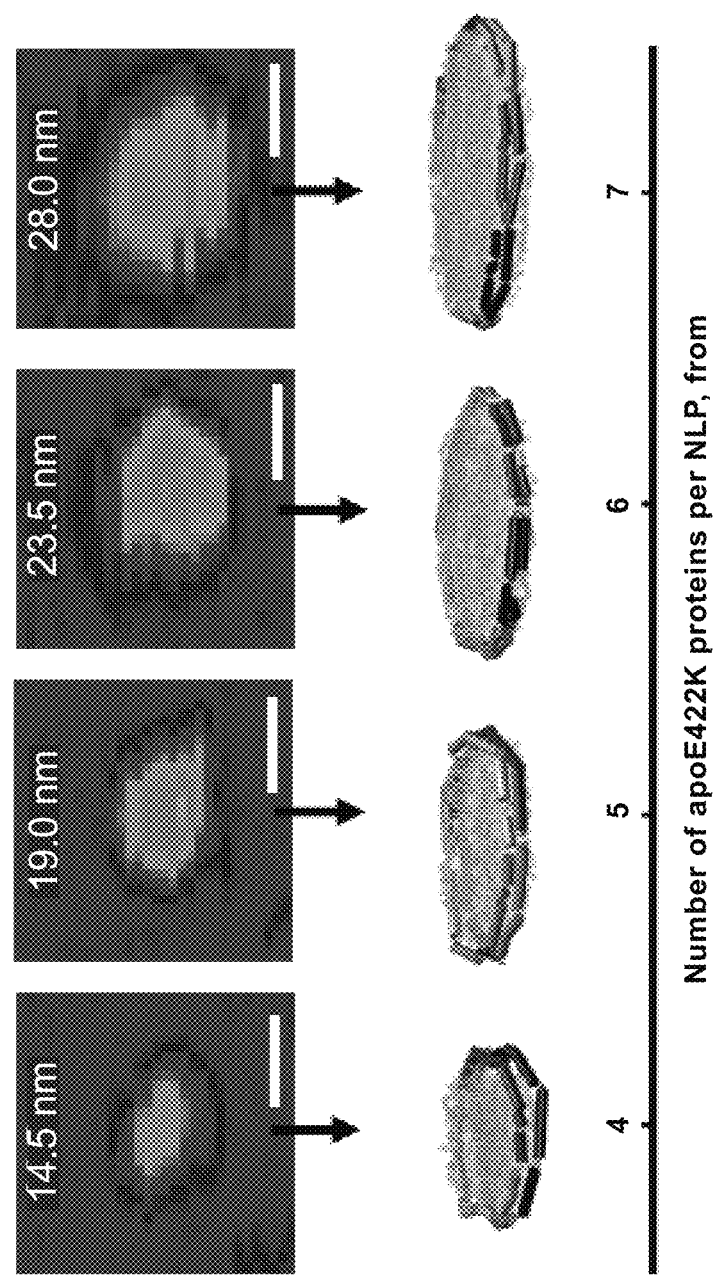
FIG. 39 shows modeling and MD simulations of E422k/DMPC NLPs sized according to an embodiment herein disclosed, the NLPs observed through AFM, IMS and TEM. E422K motifs in the simulated image are as follows; 14.5 nm; all extended, 19 nm; 2 extended, 1 hairpin, 23.5 nm: all double-hairpin, and 28 nm: all hairpin. Scale bar in AFM images—10 nm.

Example 27: Verification of NLPs Modeling and Molecular Dynamics Through Simulations of E422k/DMPC NLPs To determine if the discrete NLP diameters observed by AFM, TEM and IMS could be related to the number of E422k proteins in an NLP, NLP assembly was computationally modeled using MD simulations. As illustrated in FIG. 39, computer modeling of E422k/DMPC NLPs revealed that the multiple sizes were stable, where all the hydrophobic face of the lipid disc were matched by the protein numbers, sizes and stoichiometry. A double-belt model was assumed, but this criterion was satisfied by three protein folds; extended, hairpin, or double-hairpin. NLPs containing an odd number of E422k, the 19 nm (5 scaffold) and 28 nm (7 scaffold) NLPs, were only stable if at least one E422k adopted either the hairpin or double-hairpin motif.

Modeling of NLPs using fully extended double-belted E422k proteins (FIG. 34A) could produce NLPs of diameter 14.5 and 23.5 nm respectively containing 4 and 6 copies of the E422k protein (FIG. 39). The extended conformation of the E4 protein implies that the protein must be added in pairs to produce a double-belt and fully satisfy the hydrophobic matching required to stabilize the disc of lipid. Modeling could therefore not reproduce NLPs with diameters of 19 nm and 28 nm using fully extended double-belted E422k proteins.

Interestingly, MD simulations revealed that stable NLPs with diameters of 14.5, 19, 23.5 and 28 nm could all be formed using the hairpin (FIG. 34B) and double-hairpin (FIG. 34C) models of E422k (FIG. 39). Furthermore, simulations revealed that the 19 nm and 28 nm NLPs respectively contain 5 and 7 E422k proteins with at least one of the proteins, if not more, forming a hairpin or double-hairpin. In addition, MD simulations revealed NLPs formed from either hairpin, double-hairpin and extended models of E422k have similar stability, with full hydrophobic matching at satisfactory lipid:protein ratios as the most important factor for stability. This suggests the possibility that any one NLP can contain E422k proteins in any one or more of the three different folded forms (FIG. 34). The only constraint is that the 19 nm and 28 nm NLP are unlikely to be formed from E422k apolipoprotein that is only in the extended conformation. FIG. 34 summarizes the modeling of particle sizes and reveals that the simulations were able to verify the experimental size data yielding the following size:protein number:lipid number ratios: 14.5 nm:4:433, 19 nm:5:783, 23.5 nm:6:1270, and 28 nm:7:1780.

Figure 12:
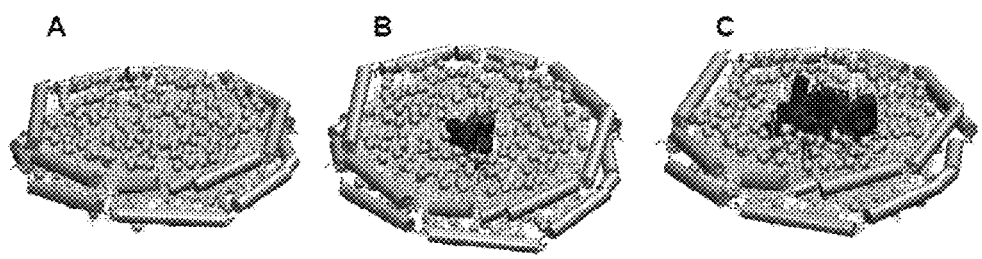
FIG. 12 shows a schematic illustration of some models of NLPs with (Panels B and C) and without (Panel A) bacteriorhodopsin according to an embodiment herein described.

Additional models are illustrated in FIG. 12. In particular in panel A, a model of a Nanolipoprotein particle (NLP) is shown with a lipid bilayer in the middle and apolipoproteins encircling the hydrophobic portion of the lipids. In panel B, an NLP modeled with a bacteriorhodopsin monomer inserted in the hydrophobic lipid core is shown. In panel C, an NLP modeled with a bacteriorhodopsin trimer inserted in the hydrophobic lipid core is shown.

The computer modeling and molecular dynamics (MD) simulations indicate that these NLPs sizes can be related to a quantized number of the E422k lipoproteins surrounding the NLPs. Discrete sizes were also observed in NLPs self-assembled from E422k/1,2-Dioleoyl-sn-Glycero-3-Phosphocholine (DOPC), A-I/DMPC, and commercially obtained NLPs purchased from Nanodisc, Inc. indicating this is likely a general and physically relevant phenomenon.

Example 28: Verification of NLPs Modeling and Molecular Dynamics in Commercial NLPs Discrete NLP diameters were also observed in A-I/DMPC NLPs, E422k/DOPC and NLPs purchased from Nanodisc, Inc. To determine if the formation of discrete NLP diameters was a general phenomenon for self-assembling NLPs, size distributions were analyzed by AFM for A-I/DMPC NLPs and NLPs (16) purchased from Nanodiscs Inc., (Urbana, Ill.). A-I/DMPC NLPs were formed with the same procedure used for E422k/DMPC NLPs with the exception that cholate was added during assembly as described in Examples 1 to 7. The purchased NLPs were formed from MSP1 a truncated version of apoA-I (apoA-I Δ1-22) and DMPC.

Figure 40:
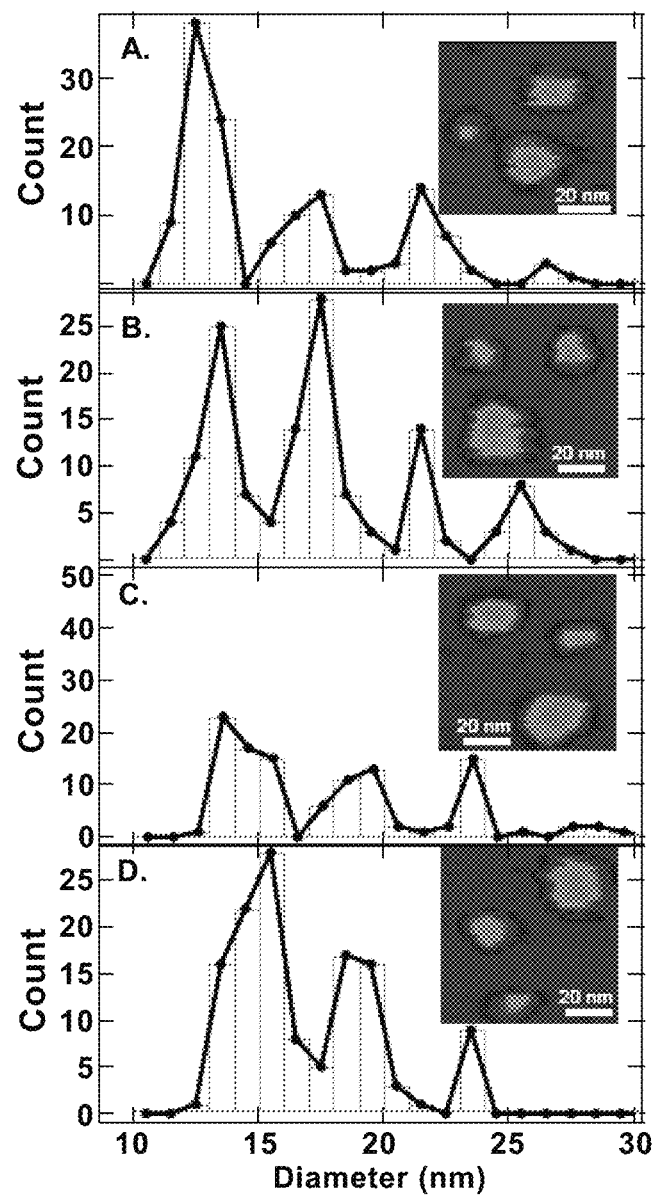
FIG. 40 shows a comparison of diameter distributions showing size heterogeneity of NLPs formed with different apolipoproteins according to an embodiment herein disclosed. Panel A shows the diameter distributions of NLPs purchased from Nanodisc Inc (constituents MSP1/DMPC). NLPs displayed quantized diameters of sizes 12.8+/−0.7, 17.2+/−1.1, 21.9+/−0.7 and 26.6+/−0.1 nm. Panel B shows the diameter distributions of A-1/DMPC NLPs. NLPs displayed quantized diameters of sizes 13.4+/−0.8, 17.4+/−0.8, 21.6+/−0.4 and 25.5+/−0.7 nm. Panel C shows the diameter distributions of E422k/DOPC NLPs. NLPs displayed quantized diameters of sizes 14.6+/−0.9, 19.0+/−0.8 23.5+/−0.7, 28.3+/−0.7 nm. Panel D shows the diameter distributions of E422k/DMPC NLPs. All histograms were binned at 1.0 nm and AFM images were stitched together to show the predominant NLP sizes.

The diameter histogram for the two different samples clearly show discrete peaks similar to those observed in E422k/DMPC NLPs except with a shift to slightly smaller particle diameters (FIG. 40A and FIG. 40B). The diameter peaks for the purchased NLPs and A-I/DMPC NLPs were 12.8, 17.2, 21.9 and 26.6 nm and 13.4, 17.4, 21.6 and 25.5 nm, respectively. The shift to smaller diameters is expected since both A-I and its recombinant derivatives have been shown to form smaller sized particles (14).

To ascertain the effect of the lipid on the discrete sized distributions observed for E422k, NLPs were assembled with DOPC instead of DMPC (FIG. 40C). Under these conditions not only were the discrete NLP diameter sizes the same as observed for E422k/DMPC NLPs, but the relative amount of each size were similar. Our results indicate that the formation of discrete sizes for lipoprotein/lipid self-assembly into NLPs may be a general phenomenon.

Example 29: Production of NLPs with an Amphipatic Peptide as Scaffold Protein

In the process of characterizing certain NLPs and evaluating their therapeutic potential in treatment of systemic fungal infections or leishmaniasis in humans, it was recognized that the apolipoprotein component of the NLP particle represents a limiting factor. In particular, those observations were made in connection with NLPs such as AMB-ND, a lipid formulation of the water insoluble antibiotic amphotericin B (AMB), termed nanodisks (ND), comprised of a nanometer scale disk shaped phospholipid bilayer stabilized by recombinant human apolipoprotein (apo) A-I. Whereas apolipoproteins serve key functions in facilitating ND formation and as a structural component of the product particles, the inventors hypothesized that peptides represent a potential alternative to recombinant apolipoprotein.

The requirement of such a peptide would be a reasonably short sequence together with the ability to induce formation of AMB-ND with retention of the stability and biological properties demonstrated for apolipoprotein containing ND. Human apoA-I mimetic peptides have been described that are capable of solubilizing phospholipid vesicles. One such peptide, termed 18A, has been extensively studied. Derivatives of this have been made by substituting Phe for Leu residues on the nonpolar face of the amphipathic alpha helix.

Figure 41:
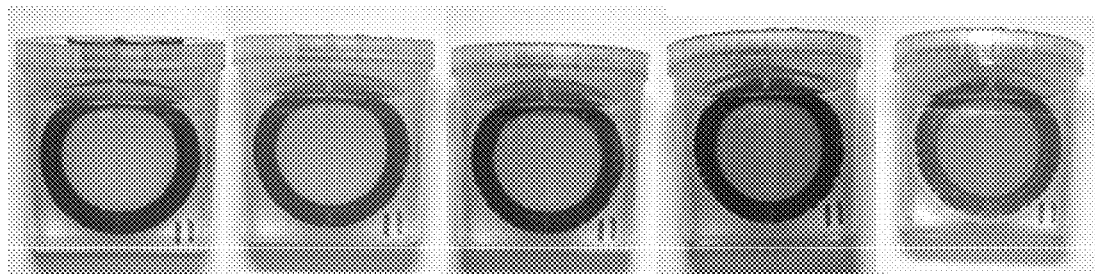
FIG. 41, shows the time course of a one-pot co-expression reaction of bR and delta 1-49 ApoA1 in the presence of DMPC vesicles. The expression of bR in the presence of DMPC alone (purple color) is shown in the figure with various shades of grey.

A helical wheel depiction of the resulting peptide, termed 4F, is shown in FIG. 41 The peptide displays characteristic features of a Class A amphipathic alpha helix including localization of positively charged lysine residues at the polar-nonpolar interface and clustering of negatively charged residues at the apex of the polar face. Here, the ability of 4F to fulfill the role of apoA-I as a component of AMB-ND was examined. The results obtained indicate that 4F efficiently induces formation AMB-ND from AMB enriched phospholipid bilayer vesicles, producing a discrete population of the particles that retain biological activity.

A series of experiments is herein illustrated related to NLPs formation starting from an 18-residue synthetic amphipathic ex-helical peptide, termed 4F (Ac-D-W-F-K-A-F-Y-D-K-V-A-E-K-F-K-E-A-F-NH (SEQ ID NO: 12), solubilized vesicles comprised of egg phosphatidylcholine (egg PC), dipentadecanoyl PC or dimyristoylphosphatidylcholine (DMPC) at rates greater than or equal to solubilization rates observed with human apolipoprotein A-I (apoA-I; 243 amino acids).

AMB (USP grade) was obtained from Research Organics Inc. Dimyristoyl-phosphatidylcholine (DMPC) and dipentadecanoyl phosphatidylcholine (PC) were from Avanti Polar Lipids Inc. and egg PC was from Sigma. Recombinant apoA-I was produced as previously described. 4F peptide was a kind gift of Dr. G. M. Ananatharamaiah I•m).

ND particles were prepared essentially as previously described. Briefly, 10 mg DMPC was dissolved in chloroform:methanol (3:1 v/v) and dried under a stream of nitrogen gas, coating the vessel wall with the phospholipid. The tube was then lyophilized for a minimum of 2 h to remove residual organic solvent. Following this the lipids were dispersed in 1 ml phosphate buffered saline (PBS; 20 mM sodium phosphate, pH 7.0, 150 mM sodium chloride) by vortexing. To the dispersed lipid 2.5 mg AMB from a stock solution (30 mg/ml in dimethylsulfoxide; DMSO) was added. Subsequently, 4 mg 4F peptide or apoA-1 (in PBS) was added and the solution incubated at 24° C. Following bath sonication to induce sample clarification, the respective ND solutions were dialyzed overnight against PBS.

Protein concentrations were determined by the bicinchoninic acid assay with bovine serum albumin as standard. Peptide concentrations were determined spectrophotometrically. Absorbance spectroscopy was performed on a Perkin-Elmer Lambda AMB levels were determined using a 20 spectrophotometer with an extinction coefficient at 416 nm 1.214×105 M'" em•' in DMSO.

Bilayer vesicles of egg PC, dipentadecanoyl PC or DMPC were prepared in 20 mM sodium phosphate, pH 7.0 by extrusion through a 200 nm filter as described by Weers et al. Unless otherwise specified, 100 µg phospholipid was incubated at a given temperature in a thermostated cell holder in the absence or presence of 40 Jig 4F peptide or apoA-I (sample volume=400 µl). Sample right angle light scattering intensity was monitored as a function of time on a PerkinElmer LS SOB luminescence spectrometer, with the excitation and emission monochromators set at 600 nm (3.6 nm slit width).

Phospholipid Vesicle Solubilization Studies

A critical aspect of AMB-ND formation relates to the ability of apolipoproteins to disrupt AMB containing phospholipid vesicles, transforming them into disk-shaped bilayers. 4F and apoA-I were characterized with respect to their relative ability to induce a time-dependent decrease in the light scattering intensity of candidate phospholipid vesicle substrates (FIG. 42), including egg PC (upper panel) dipentadecanoyl PC (middle panel) and DMPC (lower panel). Incubation of phospholipid vesicles alone had no effect on the light scattering intensity of the sample. In the case of substrate vesicles prepared with egg PC, although apoA-1 was ineffective at solubilizing the vesicle substrate, 4F induced a rapid, albeit partial, decrease in vesicle light scattering at 40 µg peptide/100 µg phospholipid. Doubling the amount of peptide to 80 µg resulted in complete egg PC vesicle solubilization.

In the case of the synthetic saturated chain phospholipid, dipentadecanoyl PC, apoA-1 was unable to induce a significant decrease in vesicle light scattering intensity upon incubation at 33° C. On the other hand, 4F induced vesicle solubilization as a function of time. Consistent with the known properties of apoA-1 [11,13], it was able to disrupt DMPC vesicles upon incubation at the gel to liquid phase transition temperature of this lipid (23.9° C.). At the same time, however, 4F was equally effective, indicating that 4F and apoA-1 are equivalent in terms of their ability to solubilize DMPC vesicles. Based on relative vesicle solubilization activity of 4F with different phospholipids, subsequent studies were carried out with DMPC.

Fluorescence Studies

Fluorescence spectra were obtained on a Perkin-Elmer LS SOB luminescence spectrometer. For quenching studies samples were excited at 280 nm and emission was monitored from 300-500 nm. Quenching data were analyzed by the Stern-Volmer equation: $FolF=1+Ksv[Q]$ where Fo and F represent the emission maximum in the absence and presence of quencher, respectively. The collisional quenching constant was estimated from the slope of plots of FrJF versus [Q].

4F contains a single Trp residue that provides a potentially useful intrinsic fluorescent probe. Indeed, whereas 4F in buffer has a wavelength of maximum Trp fluorescence emission of 350 nm (excitation 280 nm), binding to DMPC induced a ~7 nm blue shift in emission wavelength maximum together with a near doubling of Trp fluorescence emission quantum yield (FIG. 43). When fluorescence spectra of 4F AMB-ND were evaluated, however, a very different result was obtained. Trp fluorescence emission was strongly reduced suggesting AMB quenching of 4F Trp fluorescence emission.

To characterize the ability of AMB to quench 4F Trp fluorescence, 4F ND lacking AMB were prepared. Subsequently, aliquots of AMB were added to the ND solution and the effect on 4F Trp fluorescence emission intensity determined. A concentration dependent decrease in Trp fluorescence emission intensity was observed that was maximal at 8 flg AMB per 40 flg 4F ND. A Stern-Volmer plot of the quenching data revealed a $Ksv=7.7\times10^4$ Electron Microscopy Samples were diluted to a concentration of 0.02 mglml in TBS buffer. Carbon-coated 400 mesh grids (Ted Pella) were glow-discharged. 3 µl of ND samples were applied to the grid and blotted dry with Whatman filter paper. Negative staining was conducted using 3 µl of a 2% solution of uranyl acetate, and again blotted with Whatman paper. Grids were transferred to the a lEOL 1230 electron microscope, operating at 120 keV acceleration.

To characterize the structure and morphology of ND particles prepared with 4F, negative stain electron microscopy was performed. 4F-AMB ND were similar in morphology to ApoA-I-AMB-ND reported earlier [9], displaying a population of particles with an average diameter in the range of 12.5 nm (FIG. 44). Heterogeneity among ND particle size was observed.

Biological Activity of 4F AMB-ND

Cultures of the yeast, *Saccharomyces cerevisiae*, were grown in yeast extract peptone glucose broth media (YEPD; Teknova, Hollister, CAL Twenty µl of a saturated overnight culture was used to inoculate 5 ml YEPD media in the absence or presence of indicated amounts of a given AMB-ND formulation. Cultures were grown for 16 h at 30° C. with rotation and the extent of culture growth monitored by measuring sample turbidity at 600 nm.

Microtiter broth growth inhibition assays were conducted with three species of pathogenic fungi, *Candida albicans* (ATCC #: 90028), *Aspergillus fumigatus* (ATCC #: 16424) and *Cryptococcus neoformans* (isolate H99, ATCC #: 208821). Fungi were cultured in RPMI 1640 medium buffered with MOPS to pH 7.0. The final inoculum was 1×106 cells/ml. Experiments were performed in triplicate at 37° C. for 48 h according to established protocols [10, 15]. All samples tested were soluble in the standard RPMI medium used and no precipitation or interference was seen in any of the samples tested against either fungal species. Inhibitory activity was determined from cultures grown with varying amounts of a given AMB-ND formulation ranging from 0.01-16 µg/ml.

To evaluate if substitution of 4F for apoA-1 in AMB-ND affects its biological activity, growth inhibition assays were performed with the yeast, *S. cerevisiae*. As shown in FIG. 44, 4F AMBND and apoA-1 AMB-ND were generally equivalent in terms of their ability to inhibit *S. cerevisiae* growth. Fifty % growth inhibition was achieved with at 0.09 µg/ml and 0.12 µg/ml for 4F AMB-ND and apoA-1 AMB-ND, respectively. As shown in Table 6, both 4F AMB-ND and apoA-I AMB-ND were effective inhibitors of *C. albicans*, *A. fumigatus* and *C. neoformans* growth, Control ND lacking AMB did not inhibit fungal growth.

TABLE 6

Effect of AMB formulation on pathogenic fungal growth

| Fungal Species[3] | MIC (µg/ml)[1] | | |
|---|---|---|---|
| | 4F AMB ND | ApoA1 AMB ND | ApoA1 (empty) ND |
| A. fumigatus | 0.06 | 0.10 | NI[2] |
| C. albicans | 0.02 | 0.02 | NI |
| C. neoformans | 0.02 | 0.02 | NI |

MIC = minimum inhibitory concentration. Assays were performed in triplicate and the average of the assays is reported.
2NI = non-inhibitory.
'Fungi were cultured in RPMI medium buffered with MOPS to pH 7.0. The final innoeulum was 1 × 10' cells/ml (*A. fumigatus*), 1 × 104 cells/ml (*c. albicans*), and 5 × 10' cells/ml (*c. neoformans*). All experiments were performed at 35° C. for 48 h (except *C. albicans* experiments which were carried out at 35° C. for only 24 h).

Characterization studies revealed that interaction with DMPC induced a near doubling of 4F tryptophan fluorescence emission quantum yield (excitation 280 nm) and a ~7 nm blue shift in emission wavelength maximum. Inclusion of AMB in the vesicle substrate resulted in formation of 4F-AMB-ND. Spectra of AMB containing particles revealed the antibiotic is a highly effective quencher of 4F tryptophan fluorescence emission, giving rise to a Ksv'" 7.7×104 Negative stain electron microscopy revealed that AMB-ND prepared with 4F possessed a disk shaped morphology similar to ND prepared without AMB or prepared with apoA-I. In yeast and pathogenic fungi growth inhibition assays, 4F AMB-ND was as effective as apoA-I AMB-ND. The data indicate that AMB-ND generated using an amphipathic peptide in lieu of apoA-I form a discrete population of particles that possess potent biological activity. Given their intrinsic versatility, peptides may be preferred for scale up and clinical application of AMB-ND.

These results indicate that 4F and apoA-I form ND particles of similar size and efficiently solubilize significant amounts of the water insoluble polyene antibiotic, AMB. Indeed, in terms of phospholipid vesicle solubilization activity, 4F appears to be superior to apoA-I. Similar to results reported earlier, 4F but not apoA-I, can solubilize egg PC. In experiments directed to analyze 4F fluorescence properties upon association with DMPC and AMB, that AMB proved to be a highly effective quencher of Trp fluorescence emission, suggesting AMB has associated with the ND particles, These findings were verified and extended by electron microscopy. Micrographs of AMB ND prepared using 4F or apoA-I had a similar morphology, comprised of a discoidal shape with a diameter in the range of 12.5 nm. Since the biological activity of AMB-ND prepared with 4F were equivalent to that of AMB-ND prepared with apoA-I, these results suggest that 4F may offer a suitable substitute for apoA-I for formulation of AMB-ND.

The advantages of 4F versus apoA-I as a component of ND structure include the much smaller size of the peptide (18 amino acids versus 243 in the case of apoA-I). Given this large difference in molecular size and the fact that the product ND are of similar diameter, it is evident that multiple copies of peptide must align around the perimeter of the ND particle. Previous characterization studies revealed that apoA-I ND possess two copies of apoA-I, with the protein aligned in a belt-like manner around the periphery of the disk particle. Considering that 4F ND have a similar diameter, it is reasonable to speculate that 4F ND contain 20 or more peptide molecules per disc, presumably aligned perpendicular to the fatty acyl chains of ND phospholipids oriented with the hydrophobic face of the alpha helix directed toward the particle surface.

Whereas 4F ND displayed equivalent biological activity to apoA-I ND with respect to yeast and pathogenic fungi growth inhibition properties, it remains to be determined if these results can be extended to an in vivo setting. At the same time, it is worth noting that 4F and related peptides are known to function as anti-atherosclerotic agents in vivo. Thus, it is likely that 4F itself will not manifest in vivo toxicity when presented as a component of ND. Another key advantage of peptides versus protein as a component of ND particle structure relates to versatility. Given the utility of solid phase peptide synthesis versus bacterial expression of recombinant apolipoprotein using GMP methods, the cost of producing AMB-ND may be significantly reduced. Furthermore, this approach eliminates the possibility that bacterial toxins such as lipopolysaccharide may contaminate a given ND preparation. The ease of amino acid substitution also simplifies optimization studies since large numbers of amino acid substitution can be introduced and rapidly evaluated. Given the results presented in this study and the intrinsic advantages of peptides versus recombinant protein, further development of AMB-ND as a potential lipid based formulation for treatment of systemic fungal infections using 4F as the scaffold protein should be pursued.

Example 30: Production of NLPs with a Controlled Size

A nanolipoprotein particle of a predefined size was produced according to the methods and systems exemplified below. An apolipoprotein and a membrane forming lipid were mixed in TBS buffer contained in a glass reaction vessel for a defined period of time. Typically, DMPC (20 mg) is weighed out, added to a glass, round bottom tube followed by chloroform (200 ul) to dissolve lipid. Chloroform is evaporated in a stream of nitrogen with constant rotation to distribute the lipid evenly along the tube wall and placed under vacuum overnight. DMPC is either re-suspended in TBS with probe sonication or with TBS/cholate and gentle vortexing; the final concentration of cholate (20 mM) is above its critical micellar concentration (CMC). Apolipoproteins (200-250 µg) are added to the TBS/DMPC solution+/−cholate at a mass ratio of 4:1 for apoE422K and 3:1 of apoLp-III. The particle formation process is started with 3 repeated sets of transition temperature incubations, above and below the transition temperature of DMPC (23.8° C.), i.e. 10 minutes at 30° C., then 10 minutes at 20° C., with light hand mixing between incubations.

After 3 heating and cooling transitions, the samples are incubated at 23.8° C. overnight. Following assembly, samples containing cholate are dialyzed against 1000× volume of TBS buffer using 3 changes in 24 hrs. The NLPs are purified from 'free protein' and 'free lipid' by size-exclusion chromatography (VP HPLC, Shimadzu) using a SUPERDEX™ 200 HR 10/30 column (GE Healthcare), in TBS at a flow rate of 0.5 ml/min.

Example 31: Dimensions NLPs Assembled Upon Co-Expression of Scaffold Protein and Target Protein Experiments were performed according to procedures exemplified in the preceding examples to provide NLPs via in vitro co-expression of an apolipoprotein and a membrane protein. The dimensions of the NLPs so obtained are reported in Table 6.

TABLE 6

Average NLP diameters assembled by co-expression with ApoA1 (delta 49) with )various membrane proteins in the presence of DMPC.

| Membrane protein | NLP diameter (nm) |
| --- | --- |
| Yop. B/D | 16.8 +/− 4.2 |
| CHRM1 | 13.3 +/− 2 |
| bR/DMPC | 25.3 +/− 6 |
| bR/Halo | 20.8 +/− 4.4 |

Co-expression leads to varying diameters for the scaffold with inserted membrane proteins. This parameter demonstrates that that lipid interface is directly modified by the inserted protein/lipid interaction and not correlated with apolipoprotein. This demonstrates the need to characterize diameter as an important feature that is more variable in co-expression of nanolipoparticles.

Example 32: Time Course of NPLs Assembly Via One-Pot Co-Expression of Scaffold Protein and Target Protein Experiments were performed according to procedures exemplified in the preceding examples to provide NLPs via in an vitro "one pot" system wherein co-expression of bR and a Δ1-49ApoA1 was performed in presence of DMPC vesicles.

The time course of the reaction was measures as illustrate in FIG. 41. The illustrations of FIG. 41 show the rapid formation of soluble bR-NLPs by the soluble development of color within three hours of adding all the reaction constituents using a Roche RTS expression system. Previously published reports required up to 3 days to prepare the scaffold for addition to the cell-free reactions. This demonstrates that scaffold and membrane protein form a disc like complex within hours.

The examples set forth above are provided to give those of ordinary skill in the art a complete disclosure and description of how to make and use the embodiments of the devices, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the Background, Summary, Detailed Description, and Examples is hereby incorporated herein by reference. Further, the computer readable form of the sequence listing of the ASCII text file IL-11841B-P197-USD-Sequence-listing-ST25 is incorporated herein by reference in its entirety.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains. Although any methods and materials similar or equivalent to those described herein can be used in the practice for testing of the specific examples of appropriate materials and methods are described herein.

A number of embodiments of the disclosure have been described. Nevertheless, it will be understood that various modifications may be made without departing from the spirit and scope of the present disclosure. Accordingly, other embodiments are within the scope of the following claims.

REFERENCES

1. Dunn, R. J., Hackett, N. R., McCoy, J. M., Chao, B. H., Kimura, K., and Khorana, H. G (1987) Structure-function studies on bacteriorhodopsin. I. Expression of the bacterio-opsin gene in *Escherichia coli*. *J Biol Chem* 262, Page.
2. Sonar, S., Patel, N., Fischer, W, and Rothschild, K. J. (1993) Cell-free synthesis, functional refolding, and spectroscopic characterization of bacteriorhodopsin, an integral membrane protein. *Biochemistry* 32, Page.

3. Kalmbach, R., Chizhov, I., Schumacher, M. C., Friedrich, T., Bamberg, E., and Engelhard, M. (2007) Functional cell-free synthesis of a seven helix membrane protein: in situ insertion of bacteriorhodopsin into liposomes. *J Mol Biol* 371, Page.
4. Wang, J., Link, S., Heyes, C. D., and El-Sayed, M. A. (2002) Comparison of the dynamics of the primary events of bacteriorhodopsin in its trimeric and monomeric states. *Biophys J* 83, Page.
5. Bayburt, T. H., Grinkova, Y. V., and Sligar, S. G. (2006) Assembly of single bacteriorhodopsin trimers in bilayer nanodiscs. *Arch Biochem Biophys* 450, Page.
6. Chromy, B. A., Arroyo, E., Blanchette, C. D., Bench, G, Benner, H., Cappuccio, J. A., Coleman, M. A., Henderson, P. T., Hinz, A. K., Kuhn, E. A., Pesavento, J. B., Segelke, B. W., Sulchek, T. A., Tarasow, T., Walsworth, V. L., and Hoeprich, P. D. (2007) Different Apolipoproteins Impact Nanolipoprotein Particle Formation. *J Am Chem Soc*, Page.
7. Bayburt, T. H., Carlson, J. W., and Sligar, S. G. (1998) Reconstitution and imaging of a membrane protein in a nanometer-size phospholipid bilayer. *J Struct Biol* 123, Page.
8. Forstner, M., Peters-Libeu, C., Contreras-Forrest, E., Newhouse, Y, Knapp, M., Rupp, B., and Weisgraber, K. H. (1999) Carboxyl-terminal domain of human apolipoprotein E: expression, purification, and crystallization. *Protein Expr Purif* 17, Page.
9. Morrow, J. A., Arnold, K. S., and Weisgraber, K. H. (1999) Functional characterization of apolipoprotein E isoforms overexpressed in *Escherichia coli*. *Protein Expr Purif* 16, Page.
10. Jayaraman, S., Gantz, D., and Gursky, O. (2005) Structural basis for thermal stability of human low-density lipoprotein. *Biochemistry* 44, Page.
11. Gursky, O., Ranjana, and Gantz, D. L. (2002) Complex of human apolipoprotein C-1 with phospholipid: thermodynamic or kinetic stability? *Biochemistry* 41, Page.
12. Coleman, M., Nilsson, A., Russell, T. S., Rath, P., Pandey, R., and Rothschild, K. J. (1995) Asp 46 can substitute Asp 96 as the Schiff base proton donor in bacteriorhodopsin. *Biochemistry* 34, Page.
13. Klammt, C., Lohr, F., Schafer, B., Haase, W, Dotsch, V, Ruterjans, H., Glaubitz, C., and Bernhard, F. (2004) High level cell-free expression and specific labeling of integral membrane proteins. *Eur J Biochem* 271, Page.
14. Klammt, C., Schwarz, D., Lohr, F., Schneider, B., Dotsch, V, and Bernhard, F. (2006) Cell-free expression as an emerging technique for the large scale production of integral membrane protein. *Febs J* 273, Page.
15. Sonar, S., Marti, T., Rath, P., Fischer, W., Coleman, M., Nilsson, A., Khorana, H. G, and Rothschild, K. J. (1994) A redirected proton pathway in the bacteriorhodopsin mutant Tyr-57→Asp. Evidence for proton translocation without Schiff base deprotonation. *J Biol Chem* 269, Page.
16. Klammt, C., Schwarz, D., Fendler, K., Haase, W., Dotsch, V., and Bernhard, F. (2005) Evaluation of detergents for the soluble expression of alpha-helical and beta-barrel-type integral membrane proteins by a preparative scale individual cell-free expression system. *Febs J* 272, Page.
17. Camarero, J. A., Kwon, Y, and Coleman, M. A. (2004) Chemoselective attachment of biologically active proteins to surfaces by expressed protein ligation and its application for "protein chip" fabrication. *J Am Chem Soc* 126, Page.
18. Rao, R. S., Visuri, S. R., McBride, M. T., Albala, J. S., Matthews, D. L., and Coleman, M. A. (2004) Comparison of multiplexed techniques for detection of bacterial and viral proteins. *J Proteome Res* 3, Page.
19. Segelke, B. W, Schafer, J., Coleman, M. A., Lekin, T. P., Toppani, D., Skowronek, K. J., Kantardjieff, K. A., and Rupp, B. (2004) Laboratory scale structural genomics. *J Struct Funct Genomics* 5, Page.
20. Lu, B., Morrow, J. A., and Weisgraber, K. H. (2000) Conformational reorganization of the four-helix bundle of human apolipoprotein E in binding to phospholipid. *J Biol Chem* 275, Page.
21. Wientzek, M., Kay, C. M., Oikawa, K., and Ryan, R. O. (1994) Binding of insect apolipophorin III to dimyristoylphosphatidylcholine vesicles. Evidence for a conformational change. *J Biol Chem* 269, Page.
22. Forte, T. M., Nichols, A. V., Gong, E. L., Levy, R. I., and Lux, S. (1971) Electron microscopic study on reassembly of plasma high density apoprotein with various lipids. *Biochim Biophys Acta* 248, Page.
23. Abdulreda, M. H., and Moy, V. T. (2007) Atomic force microscope studies of the fusion of floating lipid bilayers. *Biophys J* 92, Page.

What is claimed is:

1. A method for producing a nanolipoprotein particle, the method comprising:
   providing a first polynucleotide encoding for a scaffold protein;
   providing a second polynucleotide encoding for a target protein;
   providing a membrane forming lipid;
   mixing, in the absence of a detergent, the first polynucleotide, the second polynucleotide and the membrane forming lipid with an in vitro cell free translation system to provide a single reaction mixture; and
   translating, in absence of a detergent, the first polynucleotide and the second polynucleotide within the single reaction mixture via the in vitro cell free translation system,
   the mixing and the translating performed to allow self-assembly of the scaffold protein, the target protein and the membrane forming lipid into the nanolipoprotein particle,
   wherein the nanolipoprotein particle comprises the target protein within a discoidal membrane lipid bilayer formed by the membrane forming lipid and stabilized by the scaffold protein, the membrane lipid bilayer attaching the target protein through interaction of a hydrophobic region of the target protein with the membrane lipid bilayer.

2. The method of claim 1, wherein the target protein is a membrane protein and the membrane forming lipid is selected from the group consisting of phospholipids, sphingolipids, glycolipids, ether lipids, sterols and alkylphosphocholines.

3. The method of claim 1, wherein the target protein is selected from the group consisting of a G protein coupled receptor (GPCR), an ion channel protein (IC) and a small multidrug resistance transporter (SMR).

4. The method of claim 1, wherein at least one of the first and the second polynucleotide is an engineered polynucleotide encoding for a chimeric product.

5. The method of claim 1, wherein the target protein is selected from the group consisting of bacteriorhodopsin, vasopressin type 2 receptor (V2R), corticotropin releasing hormone receptor 1 (CRF), endothelin receptor type B (ETB), melanocortin 5 receptor (MC5R), neurotensin receptor 1 (NTR1), 5-hydroxytryptamine receptor 1 A (5HT1A), histamine H2 receptor (H2), muscarinic acetylcholine receptor M1 (M1), hERG channel protein (hERG), α1-adrenergic receptor (α1AR), β1-adrenergic receptor (β1AR), opioid receptor type 1 (OP1R), β2-adrenergic receptor (β2AR) and muscarinic acetylcholine receptor M1 (M1).

6. The method of claim 1, wherein the first polynucleotide and the second polynucleotide are DNA polynucleotides.

7. The method of claim 1, wherein the method is performed in a cell free system operating in a continuous mode.

8. The method of claim 1, wherein the method is performed in a cell free system operating in a batch mode.

9. The method of claim 1, wherein the method is performed in a high throughput cell free expression system.

10. A method for producing a nanolipoprotein particle, the method comprising:
    providing a polynucleotide encoding for a scaffold protein;
    providing a target protein;
    providing a membrane forming lipid;
    mixing, in the absence of a detergent, the polynucleotide, the target protein and the membrane forming lipid with an in vitro cell free translation system to provide a single reaction mixture; and
    translating, in absence of a detergent, the polynucleotide within the single reaction mixture via the in vitro cell free translation system,
    the mixing and the translating performed to allow self-assembly of the scaffold protein, the target protein and the membrane forming lipid into the nanolipoprotein particle,
    wherein the nanolipoprotein particle comprises the target protein within a discoidal membrane lipid bilayer formed by the membrane forming lipid and stabilized by the scaffold protein, the membrane lipid bilayer attaching the target protein through interaction of a hydrophobic region of the target protein with the membrane lipid bilayer.

11. The method of claim 10, wherein the target protein is a membrane protein and the membrane forming lipid is selected from the group consisting of lipids, phospholipids, sphingolipids, glycolipids, ether lipids, sterols and alkylphosphocholins.

12. The method of claim 10, wherein the target protein is selected from the group consisting of a protein coupled receptor (GPCR), an ion channel protein (IC) and a small multidrug resistance transporter (SMR).

13. The method of claim 10, wherein the target protein is selected from the group consisting of bacteriorhodopsin, vasopressin type 2 receptor (V2R), corticotropin releasing hormone receptor 1 (CRF), endothelin receptor type B (ETB), melanocortin 5 receptor (MC5R), neurotensin receptor 1 (NTR1), 5-hydroxytryptamine receptor 1 A (5HT1A), histamine H2 receptor (H2), muscarinic acetylcholine receptor M1 (M1), hERG channel protein (hERG), α1-adrenergic receptor (α1AR), β1-adrenergic receptor (β1AR), opioid receptor type 1 (OP1R), β2-adrenergic receptor (β2AR) and muscarinic acetylcholine receptor M1 (M1).

14. The method of claim 10, wherein the polynucleotide is engineered to provide a chimeric product.

15. The method of claim 10, wherein the target protein further comprises a labeled molecule providing a labeling signal.

16. The method of claim 15, wherein the labeled molecule is selected from the group consisting of radioactive isotopes, chemiluminescent dyes, fluorophores, chromophores, enzymes, enzymes substrates, enzyme cofactor, enzyme inhibitors, dyes, metal ions, nanoparticles, and ligands.

17. A method for producing a nanolipoprotein particle, the method comprising:
providing a scaffold protein;
providing a polynucleotide encoding for a target protein;
providing a membrane forming lipid;
mixing, in the absence of a detergent, the polynucleotide, the scaffold protein and the membrane forming lipid with an in vitro cell free translation system to provide a single reaction mixture; and
translating, in absence of a detergent, the first polynucleotide and the second polynucleotide within the single reaction mixture via the in vitro cell free translation system,
the mixing and the translating performed to allow self-assembly of the scaffold protein, the target protein and the membrane forming lipid into the nanolipoprotein particle,
wherein the nanolipoprotein particle comprises the target protein within a discoidal membrane lipid bilayer formed by the membrane forming lipid and stabilized by the scaffold protein, the membrane lipid bilayer attaching the target protein through interaction of a hydrophobic region of the target protein with the membrane lipid bilayer.

18. The method of claim 17, wherein the target protein is a membrane protein and the membrane forming lipid is selected from the group consisting of lipids phospholipids, sphingolipids, glycolipids, ether lipids, sterols and alkylphosphocholins.

19. The method of claim 17, wherein the target protein is selected from the group consisting of a protein coupled receptor (GPCR), an ion channel protein (IC) and a small multidrug resistance transporter (SMR).

20. The method of claim 17, wherein the target protein is selected from the group consisting of bacteriorhodopsin, vasopressin type 2 receptor (V2R), corticotropin releasing hormone receptor 1 (CRF), endothelin receptor type B (ETB), melanocortin 5 receptor (MC5R), neurotensin receptor 1 (NTR1), 5-hydroxytryptamine receptor 1 A (5HT1A), histamine H2 receptor (H2), muscarinic acetylcholine receptor M1 (M1), hERG channel protein (hERG), α1-adrenergic receptor (α1AR), β1-adrenergic receptor (β1AR), opioid receptor type 1 (OP1R), β2-adrenergic receptor (β2AR) and muscarinic acetylcholine receptor M1 (M1).

21. The method of claim 17, wherein the polynucleotide is engineered to provide a chimeric product.

22. The method of claim 17, wherein the target protein further comprises a labeled molecule providing a labeling signal.

23. The method of claim 22, wherein the labeled molecule is selected from the group consisting of radioactive isotopes, chemiluminescent dyes, fluorophores, chromophores, enzymes, enzymes substrates, enzyme cofactor, enzyme inhibitors, dyes, metal ions, nanoparticles, and ligands.

* * * * *

SEQUENCE LISTING

```
<160> NUMBER OF SEQ ID NOS: 14

<210> SEQ ID NO 1
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 1
atgctaaagc tccttgacaa ctgg                                              24

<210> SEQ ID NO 2
<211> LENGTH: 25
<212> TYPE: DNA
<213> ORGANISM: Artificial Sequence
<220> FEATURE:
<223> OTHER INFORMATION: Synthetic Oligonucleotide
```

<400> SEQUENCE: 2
ttactgggtg ttgagcttct tagtg                                    25

<210> SEQ ID NO 3
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 3
ggggcatatg caagctcaaa t                                        21

<210> SEQ ID NO 4
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 4
ggggatccaa aaaaaacggg cc                                       22

<210> SEQ ID NO 5
<211> LENGTH: 193
<212> TYPE: PRT
<213> ORGANISM: Artificial Sequence
<220> FEATURE:
<223> OTHER INFORMATION: 22 kD Apolipoprotein E4 construct

<400> SEQUENCE: 5

Gly Ser Lys Val Glu Gln Ala Val Glu Thr Glu Pro Glu Pro Glu Leu
1               5                   10                  15

Arg Gln Gln Thr Glu Trp Gln Ser Gly Gln Arg Trp Glu Leu Ala Leu
            20                  25                  30

Gly Arg Phe Trp Asp Tyr Leu Arg Trp Val Gln Thr Leu Ser Glu Gln
        35                  40                  45

Val Gln Glu Glu Leu Leu Ser Ser Gln Val Thr Gln Glu Leu Arg Ala
    50                  55                  60

Leu Met Asp Glu Thr Met Lys Glu Leu Lys Ala Tyr Lys Ser Glu Leu
65                  70                  75                  80

Glu Glu Gln Leu Thr Pro Val Ala Glu Glu Thr Arg Ala Arg Leu Ser
                85                  90                  95

Lys Glu Leu Gln Ala Ala Gln Ala Arg Leu Gly Ala Asp Met Glu Asp
            100                 105                 110

Val Arg Gly Arg Leu Val Gln Tyr Arg Gly Glu Val Gln Ala Met Leu
        115                 120                 125

Gly Gln Ser Thr Glu Glu Leu Arg Val Arg Leu Ala Ser His Leu Arg
    130                 135                 140

Lys Leu Arg Lys Arg Leu Leu Arg Asp Ala Asp Asp Leu Gln Lys Arg
145                 150                 155                 160

Leu Ala Val Tyr Gln Ala Gly Ala Arg Glu Gly Ala Glu Arg Gly Leu
                165                 170                 175

Ser Ala Ile Arg Glu Arg Leu Gly Pro Leu Val Glu Gln Gly Arg Val
            180                 185                 190

Arg

<210> SEQ ID NO 6
<211> LENGTH: 36

-continued

<210> SEQ ID NO 6
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 6
gcgcgcgaga tctcgatccc gcgaaattaa tacgac                               36

<210> SEQ ID NO 7
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 7
gcgcgcgtat ccggatatag ttcctccttt cag                                  33

<210> SEQ ID NO 8
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 8
tggaattctt tgcggaatat tgcctcagtt ttgg                                 34

<210> SEQ ID NO 9
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 9
tttggatcct tatttaattg tcccagcgtc aagtaatgga aaggg                     45

<210> SEQ ID NO 10
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 10
aaaaaggcat atggttaaag ttatcggtcg tcgttccctc                           40

<210> SEQ ID NO 11
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 11
taaaatggct cttcggcaat tggcggcgat c                                    31

<210> SEQ ID NO 12
<211> LENGTH: 18
<212> TYPE: PRT
<213> ORGANISM: Artificial Sequence
<220> FEATURE:
<223> OTHER INFORMATION: Synthetic Peptide 4F

<400> SEQUENCE: 12

-continued

```
Asp Trp Phe Lys Ala Phe Tyr Asp Lys Val Ala Glu Lys Phe Lys Glu
1               5                   10                  15

Ala Phe

<210> SEQ ID NO 13
<211> LENGTH: 12
<212> TYPE: DNA
<213> ORGANISM: Synechocystis PCC6803
<220> FEATURE:
<221> NAME/KEY: CDS
<222> LOCATION: (1)..(12)

<400> SEQUENCE: 13 tgt ttt aat aaa                                                          12
Cys Phe Asn Lys
1

<210> SEQ ID NO 14
<211> LENGTH: 4
<212> TYPE: PRT
<213> ORGANISM: Synechocystis PCC6803

<400> SEQUENCE: 14

Cys Phe Asn Lys
1
```